United States Patent
Cathomen et al.

(10) Patent No.: US 11,767,512 B2
(45) Date of Patent: Sep. 26, 2023

(54) SEQUENCE SPECIFIC REAGENTS TARGETING CCR5 IN PRIMARY HEMATOPOIETIC CELLS

(71) Applicants: CELLECTIS, Paris (FR); ALBERT-LUDWIGS-UNIVERSITAT FREIBURG, Freiburg (DE)

(72) Inventors: Toni Cathomen, Freiburg (DE); Tatjana Cornu, Freiburg (DE); Philippe Duchateau, Draveil (FR); Claudio Mussolino, Freiburg (DE); Marianna Romito, Freiburg (DE); Agnes Gouble, Bois-Colombes (FR)

(73) Assignees: CELLECTIS, Paris (FR); ALBERT-LUDWIGS-UNIVERSITAT FREIBURG, Freiburg (DE)

(*) Notice: Subject to any disclaimer, the term of this patent is extended or adjusted under 35 U.S.C. 154(b) by 905 days.

(21) Appl. No.: 16/604,072

(22) PCT Filed: Apr. 13, 2018

(86) PCT No.: PCT/EP2018/059498
§ 371 (c)(1),
(2) Date: Oct. 9, 2019

(87) PCT Pub. No.: WO2018/189360
PCT Pub. Date: Oct. 18, 2018

(65) Prior Publication Data
US 2020/0392459 A1 Dec. 17, 2020

(30) Foreign Application Priority Data
Apr. 13, 2018 (DK) .......................... PA 2017 70267

(51) Int. Cl.
| | |
|---|---|
| C12N 9/22 | (2006.01) |
| C12N 5/0789 | (2010.01) |
| A61P 31/18 | (2006.01) |
| A61K 35/17 | (2015.01) |
| C07K 14/715 | (2006.01) |
| C12N 15/90 | (2006.01) |
| C12N 15/85 | (2006.01) |
| C12N 15/67 | (2006.01) |
| C12N 5/0783 | (2010.01) |
| A61K 38/00 | (2006.01) |

(52) U.S. Cl.
CPC ............ *C12N 5/0647* (2013.01); *A61K 35/17* (2013.01); *A61P 31/18* (2018.01); *C07K 14/7158* (2013.01); *C12N 5/0636* (2013.01); *C12N 9/22* (2013.01); *C12N 15/67* (2013.01); *C12N 15/85* (2013.01); *C12N 15/907* (2013.01); *A61K 38/00* (2013.01)

(58) Field of Classification Search
None
See application file for complete search history.

(56) References Cited

U.S. PATENT DOCUMENTS

2017/0152496 A1 * 6/2017 Mock ..................... C12N 9/22

FOREIGN PATENT DOCUMENTS

| CN | 103724410 A | 4/2014 | |
|---|---|---|---|
| WO | 2014065596 A1 | 5/2014 | |
| WO | 2014165825 A2 | 10/2014 | |
| WO | WO-2017144630 A1 * | 8/2017 | ......... A61K 48/0041 |
| WO | WO-2019016360 A1 * | 1/2019 | ............ A61K 35/17 |
| WO | WO-2019076486 A1 * | 4/2019 | ............ A61K 35/17 |
| WO | WO-2019149743 A1 * | 8/2019 | ......... A61K 39/0011 |
| WO | WO-2021224416 A1 * | 11/2021 | ............ A61K 48/00 |

OTHER PUBLICATIONS

Mussolino et al. 2011; A novel TALE nuclease scaffold enables high genome editing activity in combination with low toxicity. Nucleic Acids Research. 39(21): 9283-9293.*
Sather et al. 2015; Efficient modification of CCR5 in primary human hematopoietic cells using a metaTAL nuclease and AAV donor template. Sci Transl Med. 7(307): 307ra156, pp. 1-29.*
Miller et al. 2011; A TALE nuclease architecture for efficient genome editing. Nature Biotechnology. 29(2): 143-148, plus 2 pages of online methods.*
Ru et al. 2013; Targeted genome engineering in human induced pluripotent stem cells by penetrating TALENs. Cell Regeneration. 2(5): pp. 1-8.*
Cornu et al. , "Editing CCR5: a novel approach to HIV gene therapy", Advances in Experimental Medicine and Biology, Jan. 1, 2015, vol. 848, pp. 117-130.
Golding et al., "CCR5 N-terminal region plays a critical role in HIV-1 inhibition by Toxoplasma gondii-derived cyclophilin-18", Journal of Biological Chemistry, Aug. 1, 2005, vol. 280, No. 33, pp. 29570-29577.
Melikyan et al., "The role of the N-terminal segment of CCR5 in HIV-1 Env-mediated membrane fusion and the mechanism of virus adaptation to CCR5 lacking this segment", Retrovirology, Aug. 8, 2007, vol. 4, No. 1, p. 55.
Perez et al., "Establishment of HIV-1 resistance in CD4+ T cells by genome editing using zinc-finger nucleases", Nature Biotechnology, Jul. 1, 2008, vol. 26, No. 7, pp. 808-816.
Griffin et al. , "Inhibition of HIV-1 infection of primary CD4+ T-cells by gene editing of CCR5 using adenovirus-delivered CRISPR/Cas9", Journal of General Virology, Apr. 9, 2015, vol. 96, No. 8, pp. 2381-2393.

(Continued)

*Primary Examiner* — Karen Cochrane Carlson
(74) *Attorney, Agent, or Firm* — Arrigo, Lee, Guttman & Mouta-Bellum LLP

(57) ABSTRACT

The invention pertains to the field of cell therapy and HIV treatments. It provides with highly specific reagents for reducing or inactivating expression of CCR5 in primate and human primary cells, especially under the form of TALE-nucleases. These reagents allow the production of safer primary hematopoietic cells made resistant to HIV, stem cells or differentiated cells, for their infusion into HIV patients.

Figure 1:
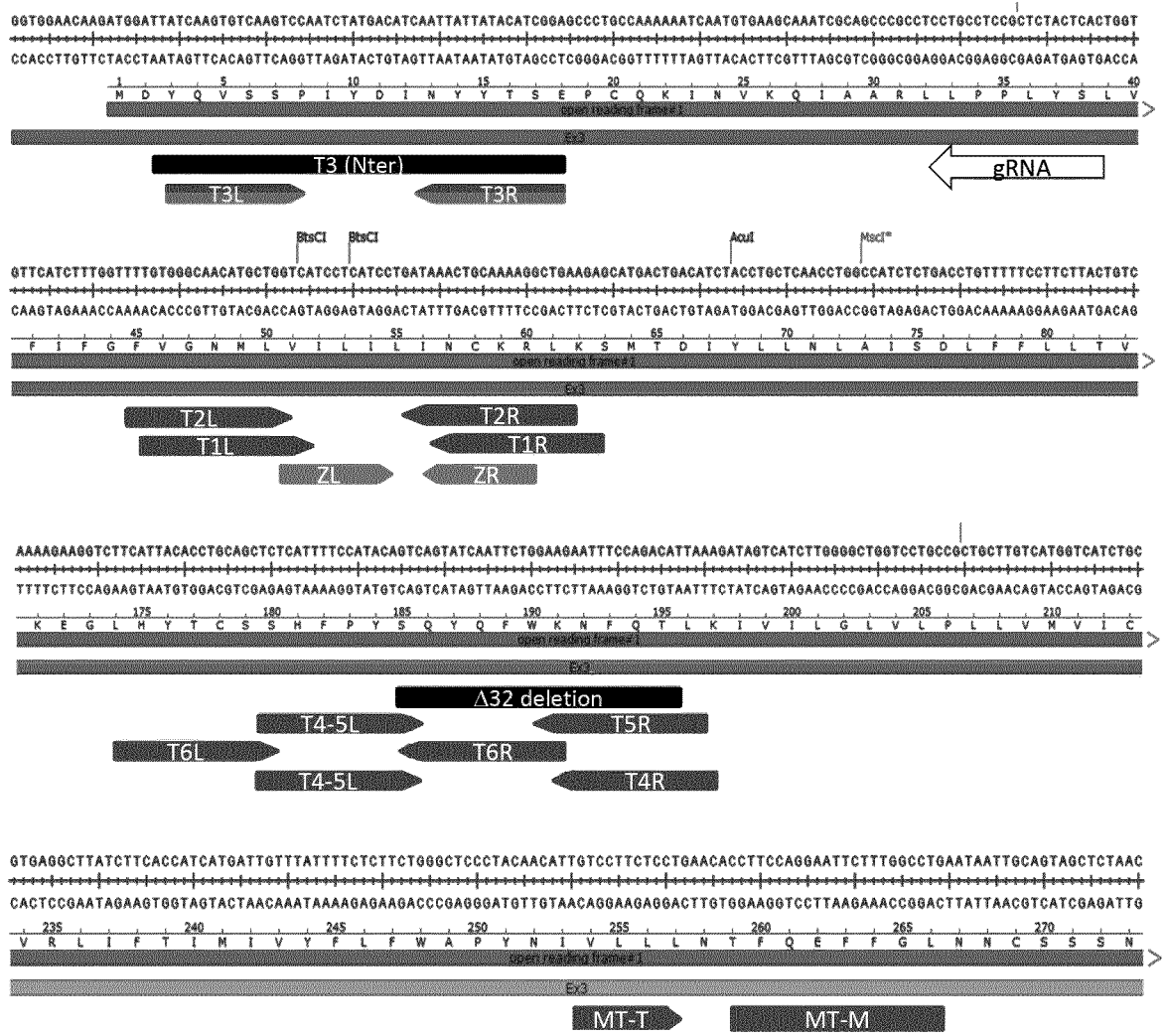

24 Claims, 12 Drawing Sheets
Specification includes a Sequence Listing.

(56) References Cited

OTHER PUBLICATIONS

Xu et al., "CRISPR/Cas9-Mediated CCR5 Ablation in Human Hematopoietic Stem/Progenitor Cells Confers HIV-1 Resistance In Vivo", Molecular Therapy, May 17, 2017, vol. 25, No. 8, pp. 1782-1789.
European Patent Office, Written Opinion for PCT Application No. PCT/EP2018/059498, dated Jun. 29, 2018.
European Patent Office, International Search Report for PCT Application No. PCT/EP2018/059498, dated Jun. 29, 2018.

* cited by examiner

SEQUENCE LISTING

<160> NUMBER OF SEQ ID NOS: 48

<210> SEQ ID NO 1
<211> LENGTH: 1056
<212> TYPE: DNA
<213> ORGANISM: homo sapiens
<220> FEATURE:
<221> NAME/KEY: CDS
<222> LOCATION: (1)..(1056)
<223> OTHER INFORMATION: CCR5 coding sequence

<400> SEQUENCE: 1

| | | | | | | | | | | | | | | | | |
|---|---|---|---|---|---|---|---|---|---|---|---|---|---|---|---|---|
| atg | gat | tat | caa | gtg | tca | agt | cca | atc | tat | gac | atc | aat | tat | tat | aca | 48 |
| Met | Asp | Tyr | Gln | Val | Ser | Ser | Pro | Ile | Tyr | Asp | Ile | Asn | Tyr | Tyr | Thr | |
| 1 | | | | 5 | | | | | 10 | | | | | 15 | | |
| tcg | gag | ccc | tgc | caa | aaa | atc | aat | gtg | aag | caa | atc | gca | gcc | cgc | ctc | 96 |
| Ser | Glu | Pro | Cys | Gln | Lys | Ile | Asn | Val | Lys | Gln | Ile | Ala | Ala | Arg | Leu | |
| | | | 20 | | | | | 25 | | | | | 30 | | | |
| ctg | cct | ccg | ctc | tac | tca | ctg | gtg | ttc | atc | ttt | ggt | ttt | gtg | ggc | aac | 144 |
| Leu | Pro | Pro | Leu | Tyr | Ser | Leu | Val | Phe | Ile | Phe | Gly | Phe | Val | Gly | Asn | |
| | | | | 35 | | | | | 40 | | | | | 45 | | |
| atg | ctg | gtc | atc | ctc | atc | ctg | ata | aac | tgc | aaa | agg | ctg | aag | agc | atg | 192 |
| Met | Leu | Val | Ile | Leu | Ile | Leu | Ile | Asn | Cys | Lys | Arg | Leu | Lys | Ser | Met | |
| 50 | | | | | 55 | | | | | 60 | | | | | | |
| act | gac | atc | tac | ctg | ctc | aac | ctg | gcc | atc | tct | gac | ctg | ttt | ttc | ctt | 240 |
| Thr | Asp | Ile | Tyr | Leu | Leu | Asn | Leu | Ala | Ile | Ser | Asp | Leu | Phe | Phe | Leu | |
| 65 | | | | 70 | | | | | 75 | | | | | 80 | | |
| ctt | act | gtc | ccc | ttc | tgg | gct | cac | tat | gct | gcc | gcc | cag | tgg | gac | ttt | 288 |
| Leu | Thr | Val | Pro | Phe | Trp | Ala | His | Tyr | Ala | Ala | Ala | Gln | Trp | Asp | Phe | |
| | | | | 85 | | | | | 90 | | | | | 95 | | |
| gga | aat | aca | atg | tgt | caa | ctc | ttg | aca | ggg | ctc | tat | ttt | ata | ggc | ttc | 336 |
| Gly | Asn | Thr | Met | Cys | Gln | Leu | Leu | Thr | Gly | Leu | Tyr | Phe | Ile | Gly | Phe | |
| | | | 100 | | | | | 105 | | | | | 110 | | | |
| ttc | tct | gga | atc | ttc | ttc | atc | atc | ctc | ctg | aca | atc | gat | agg | tac | ctg | 384 |
| Phe | Ser | Gly | Ile | Phe | Phe | Ile | Ile | Leu | Leu | Thr | Ile | Asp | Arg | Tyr | Leu | |
| | | | | 115 | | | | | 120 | | | | | 125 | | |
| gct | gtc | gtc | cat | gct | gtg | ttt | gct | tta | aaa | gcc | agg | acg | gtc | acc | ttt | 432 |
| Ala | Val | Val | His | Ala | Val | Phe | Ala | Leu | Lys | Ala | Arg | Thr | Val | Thr | Phe | |
| | 130 | | | | | 135 | | | | | 140 | | | | | |
| ggg | gtg | gtg | aca | agt | gtg | atc | act | tgg | gtg | gtg | gct | gtg | ttt | gcg | tct | 480 |
| Gly | Val | Val | Thr | Ser | Val | Ile | Thr | Trp | Val | Val | Ala | Val | Phe | Ala | Ser | |
| 145 | | | | | 150 | | | | | 155 | | | | | 160 | |
| ctc | cca | gga | atc | atc | ttt | acc | aga | tct | caa | aaa | gaa | ggt | ctt | cat | tac | 528 |
| Leu | Pro | Gly | Ile | Ile | Phe | Thr | Arg | Ser | Gln | Lys | Glu | Gly | Leu | His | Tyr | |
| | | | | 165 | | | | | 170 | | | | | 175 | | |
| acc | tgc | agc | tct | cat | ttt | cca | tac | agt | cag | tat | caa | ttc | tgg | aag | aat | 576 |
| Thr | Cys | Ser | Ser | His | Phe | Pro | Tyr | Ser | Gln | Tyr | Gln | Phe | Trp | Lys | Asn | |
| | | | 180 | | | | | 185 | | | | | 190 | | | |
| ttc | cag | aca | tta | aag | ata | gtc | atc | ttg | ggg | ctg | gtc | ctg | ccg | ctg | ctt | 624 |
| Phe | Gln | Thr | Leu | Lys | Ile | Val | Ile | Leu | Gly | Leu | Val | Leu | Pro | Leu | Leu | |
| | | | | 195 | | | | | 200 | | | | | 205 | | |
| gtc | atg | gtc | atc | tgc | tac | tcg | gga | atc | cta | aaa | act | ctg | ctt | cgg | tgt | 672 |
| Val | Met | Val | Ile | Cys | Tyr | Ser | Gly | Ile | Leu | Lys | Thr | Leu | Leu | Arg | Cys | |
| | 210 | | | | | 215 | | | | | 220 | | | | | |
| cga | aat | gag | aag | aag | agg | cac | agg | gct | gtg | agg | ctt | atc | ttc | acc | atc | 720 |
| Arg | Asn | Glu | Lys | Lys | Arg | His | Arg | Ala | Val | Arg | Leu | Ile | Phe | Thr | Ile | |
| 225 | | | | | 230 | | | | | 235 | | | | | 240 | |
| atg | att | gtt | tat | ttt | ctc | ttc | tgg | gct | ccc | tac | aac | att | gtc | ctt | ctc | 768 |
| Met | Ile | Val | Tyr | Phe | Leu | Phe | Trp | Ala | Pro | Tyr | Asn | Ile | Val | Leu | Leu | |
| | | | | 245 | | | | | 250 | | | | | 255 | | |

```
ctg aac acc ttc cag gaa ttc ttt ggc ctg aat aat tgc agt agc tct       816
Leu Asn Thr Phe Gln Glu Phe Phe Gly Leu Asn Asn Cys Ser Ser Ser
        260                 265                 270 aac agg ttg gac caa gct atg cag gtg aca gag act ctt ggg atg acg       864
Asn Arg Leu Asp Gln Ala Met Gln Val Thr Glu Thr Leu Gly Met Thr
            275                 280                 285 cac tgc tgc atc aac ccc atc atc tat gcc ttt gtc ggg gag aag ttc       912
His Cys Cys Ile Asn Pro Ile Ile Tyr Ala Phe Val Gly Glu Lys Phe
        290                 295                 300 aga aac tac ctc tta gtc ttc ttc caa aag cac att gcc aaa cgc ttc       960
Arg Asn Tyr Leu Leu Val Phe Phe Gln Lys His Ile Ala Lys Arg Phe
305                 310                 315                 320 tgc aaa tgc tgt tct att ttc cag caa gag gct ccc gag cga gca agc      1008
Cys Lys Cys Cys Ser Ile Phe Gln Gln Glu Ala Pro Glu Arg Ala Ser
                325                 330                 335 tca gtt tac acc cga tcc act ggg gag cag gaa ata tct gtg ggc ttg      1056
Ser Val Tyr Thr Arg Ser Thr Gly Glu Gln Glu Ile Ser Val Gly Leu
            340                 345                 350
```

<210> SEQ ID NO 2
<211> LENGTH: 352
<212> TYPE: PRT
<213> ORGANISM: homo sapiens

<400> SEQUENCE: 2

```
Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220

Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255
```

```
Leu Asn Thr Phe Gln Glu Phe Phe Gly Leu Asn Asn Cys Ser Ser Ser
            260                 265                 270

Asn Arg Leu Asp Gln Ala Met Gln Val Thr Glu Thr Leu Gly Met Thr
        275                 280                 285

His Cys Cys Ile Asn Pro Ile Ile Tyr Ala Phe Val Gly Glu Lys Phe
        290                 295                 300

Arg Asn Tyr Leu Leu Val Phe Phe Gln Lys His Ile Ala Lys Arg Phe
305                 310                 315                 320

Cys Lys Cys Cys Ser Ile Phe Gln Gln Glu Ala Pro Glu Arg Ala Ser
                325                 330                 335

Ser Val Tyr Thr Arg Ser Thr Gly Glu Gln Glu Ile Ser Val Gly Leu
            340                 345                 350

<210> SEQ ID NO 3
<211> LENGTH: 99
<212> TYPE: DNA
<213> ORGANISM: artificial sequence
<220> FEATURE:
<223> OTHER INFORMATION: polynucleotide sequence encoding 30 first CCR5
      amino acids

<400> SEQUENCE: 3
atggattatc aagtgtcaag tccaatctat gacatcaatt attatacatc ggagccctgc    60
caaaaaatca atgtgaagca aatcgcagcc cgcctcctg                           99

<210> SEQ ID NO 4
<211> LENGTH: 60
<212> TYPE: DNA
<213> ORGANISM: artificial sequence
<220> FEATURE:
<223> OTHER INFORMATION: polynucleotide sequence encoding 20 first CCR5
      amino acids

<400> SEQUENCE: 4
atggattatc aagtgtcaag tccaatctat gacatcaatt attatacatc ggagccctgc    60

<210> SEQ ID NO 5
<211> LENGTH: 48
<212> TYPE: DNA
<213> ORGANISM: artificial sequence
<220> FEATURE:
<223> OTHER INFORMATION: polynucleotide sequence encoding 2-18 CCR5
      amino acids

<400> SEQUENCE: 5
tatcaagtgt caagtccaat ctatgacatc aattattata catcggag                 48

<210> SEQ ID NO 6
<211> LENGTH: 16
<212> TYPE: DNA
<213> ORGANISM: artificial sequence
<220> FEATURE:
<223> OTHER INFORMATION: TALEN T3L target sequence

<400> SEQUENCE: 6
tatcaagtgt caagtc                                                    16

<210> SEQ ID NO 7
<211> LENGTH: 16
<212> TYPE: DNA
<213> ORGANISM: artificial sequence
<220> FEATURE:
<223> OTHER INFORMATION: TALEN T3R target sequence
```

-continued

```
<400> SEQUENCE: 7
tccgatgtat aataat                                                       16

<210> SEQ ID NO 8
<211> LENGTH: 15
<212> TYPE: DNA
<213> ORGANISM: artificial sequence
<220> FEATURE:
<223> OTHER INFORMATION: TALEN T3 spacer sequence

<400> SEQUENCE: 8
caatctatga catca                                                        15

<210> SEQ ID NO 9
<211> LENGTH: 925
<212> TYPE: PRT
<213> ORGANISM: artificial sequence
<220> FEATURE:
<223> OTHER INFORMATION: TALEN T3L polypeptide sequence

<400> SEQUENCE: 9

Met Gly Asp Pro Lys Lys Arg Lys Val Ile Asp Ile Ala Asp Leu
 1               5                  10                  15

Arg Thr Leu Gly Tyr Ser Gln Gln Gln Glu Lys Ile Lys Pro Lys
                20                  25                  30

Val Arg Ser Thr Val Ala Gln His His Glu Ala Leu Val Gly His
                35                  40                  45

Phe Thr His Ala His Ile Val Ala Leu Ser Gln His Pro Ala Ala Leu
     50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
            130                 135                 140

Gly Ala Pro Leu Asn Leu Thr Pro Glu Gln Val Val Ala Ile Ala Ser
145                 150                 155                 160

Asn Ile Gly Gly Lys Gln Ala Leu Glu Thr Val Gln Ala Leu Leu Pro
                165                 170                 175

Val Leu Cys Gln Ala His Gly Leu Thr Pro Gln Gln Val Val Ala Ile
            180                 185                 190

Ala Ser Asn Gly Gly Gly Lys Gln Ala Leu Glu Thr Val Gln Arg Leu
            195                 200                 205

Leu Pro Val Leu Cys Gln Ala His Gly Leu Thr Pro Glu Gln Val Val
            210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
            260                 265                 270

Val Gln Ala Leu Leu Pro Val Leu Cys Gln Ala His Gly Leu Thr Pro
            275                 280                 285
```

```
Glu Gln Val Val Ala Ile Ala Ser Asn Ile Gly Gly Lys Gln Ala Leu
290                 295                 300

Glu Thr Val Gln Ala Leu Leu Pro Val Leu Cys Gln Ala His Gly Leu
305                 310                 315                 320

Thr Pro Gln Gln Val Val Ala Ile Ala Ser Asn Asn Gly Gly Lys Gln
            325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
            405                 410                 415

Cys Gln Ala His Gly Leu Thr Pro Gln Gln Val Val Ala Ile Ala Ser
            420                 425                 430

Asn Gly Gly Lys Gln Ala Leu Glu Thr Val Gln Arg Leu Leu Pro
            435                 440                 445

Val Leu Cys Gln Ala His Gly Leu Thr Pro Glu Gln Val Val Ala Ile
450                 455                 460

Ala Ser His Asp Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
            485                 490                 495

Ala Ile Ala Ser Asn Ile Gly Gly Lys Gln Ala Leu Glu Thr Val Gln
            500                 505                 510

Ala Leu Leu Pro Val Leu Cys Gln Ala His Gly Leu Thr Pro Glu Gln
            515                 520                 525

Val Val Ala Ile Ala Ser Asn Ile Gly Gly Lys Gln Ala Leu Glu Thr
            530                 535                 540

Val Gln Ala Leu Leu Pro Val Leu Cys Gln Ala His Gly Leu Thr Pro
545                 550                 555                 560

Gln Gln Val Val Ala Ile Ala Ser Asn Asn Gly Gly Lys Gln Ala Leu
            565                 570                 575

Glu Thr Val Gln Arg Leu Leu Pro Val Leu Cys Gln Ala His Gly Leu
            580                 585                 590

Thr Pro Gln Gln Val Val Ala Ile Ala Ser Asn Gly Gly Gly Lys Gln
            595                 600                 605

Ala Leu Glu Thr Val Gln Arg Leu Leu Pro Val Leu Cys Gln Ala His
            610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
            645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
690                 695                 700
```

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
            725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
            770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
            835                 840                 845

Lys Val Tyr Pro Ser Ser Val Thr Glu Phe Lys Phe Leu Phe Val Ser
850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
            885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
            915                 920                 925

<210> SEQ ID NO 10
<211> LENGTH: 925
<212> TYPE: PRT
<213> ORGANISM: artificial sequence
<220> FEATURE:
<223> OTHER INFORMATION: TALEN T3R polypeptide sequence

<400> SEQUENCE: 10

Met Gly Asp Pro Lys Lys Lys Arg Lys Val Ile Asp Ile Ala Asp Leu
1               5                   10                  15

Arg Thr Leu Gly Tyr Ser Gln Gln Gln Gln Lys Ile Lys Pro Lys
            20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
        50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
130                 135                 140

```
Gly Ala Pro Leu Asn Leu Thr Pro Glu Gln Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Glu Gln Val Val Ala Ile
            180                 185                 190

Ala Ser His Asp Gly Gly Lys Gln Ala Leu Glu Thr Val Gln Arg Leu
        195                 200                 205

Leu Pro Val Leu Cys Gln Ala His Gly Leu Thr Pro Gln Gln Val Val
    210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
            260                 265                 270

Val Gln Ala Leu Leu Pro Val Leu Cys Gln Ala His Gly Leu Thr Pro
        275                 280                 285

Gln Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Asn Gly Gly Lys Gln
                325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Gln Gln Val Val Ala Ile Ala Ser
            420                 425                 430

Asn Gly Gly Gly Lys Gln Ala Leu Glu Thr Val Gln Arg Leu Leu Pro
        435                 440                 445

Val Leu Cys Gln Ala His Gly Leu Thr Pro Glu Gln Val Val Ala Ile
    450                 455                 460

Ala Ser Asn Ile Gly Gly Lys Gln Ala Leu Glu Thr Val Gln Ala Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
            500                 505                 510

Ala Leu Leu Pro Val Leu Cys Gln Ala His Gly Leu Thr Pro Gln Gln
        515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Ala His Gly Leu Thr Pro
545                 550                 555                 560
```

Glu Gln Val Val Ala Ile Ala Ser Asn Ile Gly Gly Lys Gln Ala Leu
             565                 570                 575

Glu Thr Val Gln Ala Leu Leu Pro Val Leu Cys Gln Ala His Gly Leu
        580                 585                 590

Thr Pro Glu Gln Val Val Ala Ile Ala Ser Asn Ile Gly Gly Lys Gln
            595                 600                 605

Ala Leu Glu Thr Val Gln Ala Leu Leu Pro Val Leu Cys Gln Ala His
        610                 615                 620

Gly Leu Thr Pro Gln Gln Val Val Ala Ile Ala Ser Asn Gly Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Lys
                725                 730                 735

Lys Ser Glu Leu Arg His Lys Leu Lys Tyr Val Pro His Glu Tyr Ile
                740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 11
<211> LENGTH: 7445
<212> TYPE: DNA
<213> ORGANISM: artificial sequence
<220> FEATURE:
<223> OTHER INFORMATION: TALEN T3L plasmid sequence

<400> SEQUENCE: 11

```
aaacccacga cacctgaaat ggaagaaaaa aactttgaac cactgtctga ggcttgagaa      60
tgaaccaaga tccaaactca aaaagggcaa attccaagga gaattacatc aagtgccaag     120
ctggcctaac ttcagtctcc acccactcag tgtggggaaa ctccatcgca taaaacccct    180
cccccaacc taaagacgac gtactccaaa agctcgagaa ctaatcgagg tgcctggacg     240
gcgcccggta ctccgtggag tcacatgaag cgacggctga ggacggaaag gccctttttcc    300
tttgtgtggg tgactcaccc gcccgctctc ccgagcgccg cgtcctccat tttgagctcc    360
ctgcagcagg gccgggaagc ggccatcttt ccgctcacgc aactggtgcc gaccgggcca    420
gccttgccgc ccagggcggg gcgatacacg gcggcgcgag gccaggcacc agagcaggcc    480
ggccagcttg agactacccc cgtccgattc tcggtggccg cgctcgcagg ccccgcctcg    540
ccgaacatgt gcgctgggac gcacgggccc cgtcgccgcc cgcggcccca aaaaccgaaa    600
taccagtgtg cagatcgatc ttggcccgca tttacaagac tatcttgcca gaaaaaaagc    660
gtcgcagcag gtcatcaaaa attttaaatg gctagagact tatcgaaagc agcgagacag    720
gcgcgaaggt gccaccagat tcgcacgcgg cggcccagc gcccaagcca ggcctcaact    780
caagcacgag gcgaaggggc tccttaagcg caaggcctcg aactctccca cccacttcca    840
acccgaagct cgggatcaag aatcacgtac tgcagccagg ggcgtggaag taattcaagg    900
cacgcaaggg ccataacccg taaagaggcc aggcccgcgg gaaccacaca cggcacttac    960
ctgtgttctg gcggcaaacc cgttgcgaaa agaacgttc acggcgacta ctgcacttat   1020
atacggttct ccccaccct cgggaaaaag gcggagccag tacacgacat cacttttccca   1080
gtttaccccg cgccaccttc tctaggcacc ggttcaattg ccgacccctc cccccaactt   1140
ctcggggact gtgggcgatg tgcgctctgc ccactgacgg gcaccggagc ctcacgcatg   1200
ctcttctcca cctcagtgat gacgagagcg ggcgggtgag ggggcgggaa cgcagcgatc   1260
tctgggttct acgttagtgg gagtttaacg acggtccctg ggattcccca aggcaggggc   1320
gagtcctttt gtatgaatta ctctcagctc cggtcggggc gggttggggg gggtggtgac   1380
gggggaggccg cctggaaggg acgtgcagaa tcttccctct accattgctg gcttagctcc   1440
aaaggttgta ttgagattag ggtgtacctt cgcctctcaa tcagcctccc gtcctcagcc   1500
ttgccatctc gctagtccgg gacaaatccc tagagcgtct tcctctgcgg gtctcagccc   1560
agcccggggt tggctcctcc tccgccccgg cttccgcgcc cctcccgtgt ggcaaggagt   1620
accaggcccg gggaccccga ggggcttggg gcgaagggtc gggactgggg gcctccttaa   1680
cggctcacgg acttgcgaga ggttcggctc gatggccgtg aaagcgacga atccgctcct   1740
gtgctggcct cttggctcct tccattcaaa gccagctgct tttatggaag cccgtaacac   1800
gtcatctccc cctggtactc cagatgtcca ggctttcagt ttagaataga ctcagtccta   1860
cagttagctt tggcgcgatt cactggccgt cgttttacaa cgtcgtgact gggaaaaccc   1920
tggcgttacc caacttaatc gccttgcagc acatccccct ttcgccagct ggcgtaatag   1980
cgaagaggcc cgcaccgatc gcccttccca acagttgcgc agcctgaatg gcgaatggcg   2040
cctgatgcgg tatttctcc ttacgcatct gtgcggtatt tcacaccgca tagtcaggtg   2100
gcacttttcg gggaaatgtg cgcggaaccc ctatttgttt attttttctaa atacattcaa   2160
atatgtatcc gctcatgaga caataaccct gataaatgct tcaataatat tgaaaaagga   2220
agagtatgag tattcaacat ttccgtgtcg cccttattcc cttttttgcg gcattttgcc   2280
ttcctgtttt tgctcaccca gaaacgctgg tgaaagtaaa agatgctgaa gatcagttgg   2340
```

-continued

```
gtgcacgagt gggttacatc gaactggatc tcaacagcgg taagatcctt gagagttttc      2400
gccccgaaga acgttttcca atgatgagca ctttttaaagt tctgctatgt ggcgcggtat     2460
tatcccgtat tgacgccggg caagagcaac tcggtcgccg catacactat tctcagaatg     2520
acttggttga gtactcacca gtcacagaaa agcatcttac ggatggcatg acagtaagag     2580
aattatgcag tgctgccata accatgagtg ataacactgc ggccaactta cttctgacaa     2640
cgatcggagg accgaaggag ctaaccgctt ttttgcacaa catggggggat catgtaactc     2700 gccttgatcg ttgggaaccg gagctgaatg aagccatacc aaacgacgag cgtgacacca     2760
cgatgcctgt agcaatggca acaacgttgc gcaaactatt aactggcgaa ctacttactc     2820
tagcttcccg gcaacaatta atagactgga tggaggcgga taaagttgca ggaccacttc     2880
tgcgctcggc ccttccggct ggctggttta ttgctgataa atctggagcc ggtgagcgtg     2940
ggtctcgcgg tatcattgca gcactggggc cagatggtaa gccctcccgt atcgtagtta     3000
tctacacgac ggggagtcag gcaactatgg atgaacgaaa tagacagatc gctgagatag     3060
gtgcctcact gattaagcat tggtaactgt cagaccaagt ttactcatat atactttaga     3120
ttgatttaaa acttcatttt taatttaaaa ggatctaggt gaagatcctt tttgataatc     3180
tcatgaccaa aatcccttaa cgtgagtttt cgttccactg agcgtcagac cccgtagaaa     3240
agatcaaagg atcttcttga gatcctttt ttctgcgcgt aatctgctgc ttgcaaacaa     3300
aaaaaccacc gctaccagcg gtggtttgtt tgccggatca agagctacca actcttttc     3360 cgaaggtaac tggcttcagc agagcgcaga taccaaatac tgtccttcta gtgtagccgt     3420
agttaggcca ccacttcaag aactctgtag caccgcctac atacctcgct ctgctaatcc     3480
tgttaccagt ggctgctgcc agtggcgata gtcgtgtct taccggggttg gactcaagac     3540 gatagttacc ggataaggcg cagcggtcgg gctgaacggg gggttcgtgc acacagccca     3600
gcttggagcg aacgacctac accgaactga gatacctaca gcgtgagcta tgagaaagcg     3660
ccacgcttcc cgaagggaga aaggcggaca ggtatccgt aagcggcagg gtcggaacag     3720
gagagcgcac gagggagctt ccaggggggaa acgcctggta tctttatagt cctgtcgggt     3780
ttcgccacct ctgacttgag cgtcgatttt tgtgatgctc gtcaggggg cggagcctat     3840 ggaaaaacgc cagcaacgcg gcctttttac ggttcctggc cttttgctgg ccttttgctc     3900
acatgttctt tcctgcgtta tcccctgatt ctgtggataa ccgtattacc gcctttgagt     3960
gagctgatac cgctcgccgc agccgaacga ccgagcgcag cgagtcagtg agcgaggaag     4020
cggaagagcg cccaatacgc aaaccgcctc tccccgcgcg ttggccgatt cattaatgca     4080
gctggcacga caggtttccc gactggaaag cgggcagtga gcgcaacgca attaatgtga     4140
gttagctcac tcattaggca ccccaggctt tacactttat gcttccggct cgtatgttgt     4200
gtggaattgt gagcggataa caatttcaca caggaaacag ctatgaccat gattacgcca     4260
agctctaggt cttaattaag aagatatccc atagagccca ccgcatcccc agcatgcctg     4320
ctattgtctt cccaatcctc cccccttgctg tcctgccccca ccccaccccc cagaatagaa     4380
tgacacctac tcagacaatg cgatgcaatt tcctcatttt attaggaaag gacagtggga     4440 gtggcaccttt ccagggtcaa ggaaggcacg ggggaggggc aaacaacaga tggctggcaa     4500
ctagaaggca cagtcgaagc ttcagctgct gcaggctcga ggagctcgtc tagaggatcg     4560
ctcgagttat cagtcggccg cgaagttgat ctcgccgttg ttgaacttcc tcctcacctc     4620
ctccagggtc agggtgccgg ccttgatcat ctcgccgccg atcaggagct cctccacgga     4680
cagcacggcg ccgttgcagt tggtgatgtg gttcagcctg gtcagctggg ccttgtagtt     4740
```

```
gcccttgaag tggccggaca cgaacaggaa cttgaactcg gtcacgctgg aggggtacac    4800
cttccaccac tcgttggggt tgatgtgctt gttcctggtc tggttctcct ccacgtacct    4860
ctgcatttcg tcggcctggc cgatgggcag gttgtagccg ccggagtagg ccttggtgtc    4920
cacgatcacg ccgtagtcga tgggggagcc cacggtgtag atggcgccgt cgggcttcct    4980
ggagccgccc aggtgcttgc ccctgtagcc gtacaccttc atgaagaact ccatcacctt    5040
catctccagg atacggtcct gggtgctgtt ccgggcgatc tcgatcagct cgatgtactc    5100
gtggggcacg tacttcagct tgtgcctcaa ctcggatttc ttctcctcca gctcggactt    5160
caccagctgg gaacggctga taggatcccc caatccctt ttcactgcat ccagcgcagg    5220
acgcccgccg aggcaggcca aggcgacgag gtggtcgttg gtcaacgcgg ccaacgccgg    5280
atcagggcga gataactggg caacaatgct ctcgagggcg ggcctaccgc ctccattaga    5340
agctatagcg accacctgct gcggtgtgag cccatgagcc tgacacaaaa caggcaacaa    5400
tcgctgcacc gtttccaggg cctgttttcc gccgtcatgg ctcgcgatag caacaacctg    5460
ttcgggtgtc agcccgtgtg cttgacagag aacaggcaac agcctctgga ctgtctccaa    5520
tgcctgtttc cctccgccat tgcttgcaat tgcgacgact tgctgtgggg tcagaccgtg    5580
tgcctgacac agcacgggca gcaggcgctg gactgtttcg agggcttgct tgccaccgtt    5640
attggatgcg atggccacaa cttgttgtgg ggtaagcccg tgcgcctggc acaacactgg    5700
cagcaacgcc tgaactgttt ccagcgcttg cttaccgcca atattgctgg cgatcgctac    5760
cacttgttcg ggagtcaggc catgagcctg gcacagaacg ggcaggaggg cctgaacggt    5820
ttcgagggcc tgcttgcctc caatgttaga ggcaatggcg accacctgtt caggggtaag    5880
gccgtgagcc tggcagagca caggcagcag cctctgcact gtttccaatg cttgcttccc    5940
tccgtcatga gaagcgatag cgacaacttg ctcgggggtc aggccatgtg cttggcagag    6000
aactgggagc aacctttgca cagtctcgag tgcctgcttt ccgcctccgt tgctagcaat    6060
agccacaacc tgttgtgggg tcaggccgtg cgcctgacac aggacgggaa ggagtctttg    6120
caccgtttcg agtgcctgtt taccgccgtt gtttgatgcg attgccacga cctgctgggg    6180
tgtgagtcca tgagcttgac agaggaccgg aaggagtctc tggacggttt ccagtgcttg    6240
tttacctcct ccgtttgaag cgattgcaac cacttgttgc ggggtaagtc catgcgcttg    6300
gcagagcacc ggcagcagtc tctgtacggt ttccagagct tgcttgccgc cattattact    6360
ggcaatagcc accacctgtt ggggagtgag gccgtgagct tggcagagta caggcaacag    6420
agcctgcacg gtttcgagcg cctgcttccc gccaatgttt gaggcaatag cgactacttg    6480
ttcgggtgta aggccgtggg cctgacacaa gactggcagg agagcctgta cggtctcgag    6540
agcctgcttc ccaccgatat tggacgcgat ggctacgacc tgctcaggcg tcagtccgtg    6600
ggcttgacac aaaacgggca gcagccgctg cacagtctcc agggcttgct ttcctccgtc    6660
gtgtgaagct atggccacga cctgttcagg agtcagccca tgagcttggc acaatactgg    6720
gagaagtctc tgcactgtct ccaggcctg cttccctcct ccattgctag cgatggccac    6780
cacttgctgt ggagtcagcc cgtgggcctg gcaaagcaca ggaagcaagg cctgaacagt    6840
ctcgagcgct tgtttccctc cgatattaga agcaatagca acgacctgtt ctggggtcaa    6900
gttgagcggg gcaccgtca gtgcattgcg ccatgcatgc actgcctcca ctgcggtcac    6960
gccgccacgt tttgcaatct tgagaagttg gcctgtgtcc aactgtaacg gtggacctct    7020
caactctccc gccaccgtga gcaaggcctc cagagcgcgt gcgccggacc actgtttgcc    7080
gacgccaacg atcgcttcgt gtgtcgcctc tggcaacgct gcgatcatgt cctgatactt    7140
```

| | |
|---|---:|
| gacagcgacg gtccctaacg ctgccgggtg ttggcttaac gcaacgatgt gcgcgtgtgt | 7200 |
| aaacccgtgg ccgaccagtg cctcgtggtg ctgcgccact gtcgaacgaa ccttcggttt | 7260 |
| gatcttctcc tgttgctgct ggctgtagcc gagcgtgcgt agatcggcga tatcgatagc | 7320 |
| gtaatctgga acatcgtatg ggtaatcgat gaccttacgt ttcttttag gatcgcccat | 7380 |
| ggtggcggct tggcgcgtga cagcgctagt ggcgcgccga actagttatg gtaccaagtt | 7440 |
| taaac | 7445 |

```
<210> SEQ ID NO 12
<211> LENGTH: 7463
<212> TYPE: DNA
<213> ORGANISM: artificial sequence
<220> FEATURE:
<223> OTHER INFORMATION: TALEN T3R plasmid sequence

<400> SEQUENCE: 12
```

| | |
|---|---:|
| aaacccacga cacctgaaat ggaagaaaaa aactttgaac cactgtctga ggcttgagaa | 60 |
| tgaaccaaga tccaaactca aaagggcaa attccaagga gaattacatc aagtgccaag | 120 |
| ctggcctaac ttcagtctcc acccactcag tgtggggaaa ctccatcgca taaaacccct | 180 |
| ccccccaacc taaagacgac gtactccaaa agctcgagaa ctaatcgagg tgcctggacg | 240 |
| gcgcccggta ctccgtggag tcacatgaag cgacggctga ggacggaaag gccctttcc | 300 |
| tttgtgtggg tgactcaccc gcccgctctc ccgagcgccg cgtcctccat tttgagctcc | 360 |
| ctgcagcagg gccgggaagc ggccatcttt ccgctcacgc aactggtgcc gaccgggcca | 420 |
| gccttgccgc ccagggcggg gcgatacacg cggcgcgag gccaggcacc agagcaggcc | 480 |
| ggccagcttg agactacccc cgtccgattc tcggtggccg cgctcgcagg ccccgcctcg | 540 |
| ccgaacatgt gcgctgggac gcacgggccc gtcgccgcc gcggccccca aaaaccgaaa | 600 |
| taccagtgtg cagatcgatc ttggcccgca tttacaagac tatcttgcca gaaaaaaagc | 660 |
| gtcgcagcag gtcatcaaaa attttaaatg gctagagact tatcgaaagc agcgagacag | 720 |
| gcgcgaaggt gccaccagat cgcacgcgg cggcccagc gcccaagcca ggcctcaact | 780 |
| caagcacgag gcgaagggc tccttaagcg caaggcctcg aactctccca cccacttcca | 840 |
| acccgaagct cgggatcaag aatcacgtac tgcagccagg ggcgtggaag taattcaagg | 900 |
| cacgcaaggg ccataacccg taaagaggcc aggcccgcgg gaaccacaca cggcacttac | 960 |
| ctgtgttctg gcggcaaacc cgttgcgaaa aagaacgttc acggcgacta ctgcacttat | 1020 |
| atacggttct ccccccaccct cgggaaaaag gcggagccag tacacgacat cactttccca | 1080 |
| gtttaccccg cgccaccttc tctaggcacc ggttcaattg ccgacccctc cccccaactt | 1140 |
| ctcggggact gtgggcgatg tgcgctctgc ccactgacgg gcaccggagc ctcacgcatg | 1200 |
| ctcttctcca cctcagtgat gacgagagcg ggcgggtgag ggggcgggaa cgcagcgatc | 1260 |
| tctgggttct acgttagtgg gagtttaacg acggtccctg ggattcccca aggcaggggc | 1320 |
| gagtcctttt gtatgaatta ctctcagctc cggtcgggc gggttgggg gggtggtgac | 1380 |
| ggggaggccg cctggaaggg acgtgcagaa tcttccctct accattgctg gcttagctcc | 1440 |
| aaaggttgta ttgagattag ggtgtacctt cgcctctcaa tcagcctccc gtcctcagcc | 1500 |
| ttgccatctc gctagtccgg gacaaatccc tagagcgtct tcctctgcgg gtctcagccc | 1560 |
| agcccggggt tggctcctcc tccgccccgg cttccgcgcc cctcccgtgt ggcaaggagt | 1620 |
| accaggcccg gggaccccga ggggcttggg gcgaagggtc gggactgggg gcctccttaa | 1680 |
| cggctcacgg acttgcgaga ggttcggctc gatggccgtg aaagcgacga atccgctcct | 1740 |

```
                                                        -continued gtgctggcct cttggctcct tccattcaaa gccagctgct tttatggaag cccgtaacac    1800
gtcatctccc cctggtactc cagatgtcca ggctttcagt ttagaataga ctcagtccta    1860
cagttagctt tggcgcgatt cactggccgt cgttttacaa cgtcgtgact gggaaaaccc    1920
tggcgttacc caacttaatc gccttgcagc acatccccct ttcgccagct ggcgtaatag    1980
cgaagaggcc cgcaccgatc gcccttccca acagttgcgc agcctgaatg gcgaatggcg    2040
cctgatgcgg tattttctcc ttacgcatct gtgcggtatt tcacaccgca tagtcaggtg    2100
gcacttttcg gggaaatgtg cgcggaaccc ctatttgttt attttttctaa atacattcaa   2160 atatgtatcc gctcatgaga caataaccct gataaatgct tcaataatat tgaaaaagga    2220
agagtatgag tattcaacat ttccgtgtcg cccttattcc cttttttgcg cattttgcc     2280 ttcctgtttt tgctcaccca gaaacgctgg tgaaagtaaa agatgctgaa gatcagttgg    2340
gtgcacgagt gggttacatc gaactggatc tcaacagcgg taagatcctt gagagttttc    2400
gccccgaaga cgttttccca atgatgagca cttttaaagt tctgctatgt ggcgcggtat    2460
tatcccgtat tgacgccggg caagagcaac tcggtcgccg catacactat tctcagaatg    2520
acttggttga gtactcacca gtcacagaaa agcatcttac ggatggcatg acagtaagag    2580
aattatgcag tgctgccata accatgagtg ataacactgc ggccaactta cttctgacaa    2640
cgatcggagg accgaaggag ctaaccgctt ttttgcacaa catgggggat catgtaactc    2700
gccttgatcg ttgggaaccg gagctgaatg aagccatacc aaacgacgag cgtgacacca    2760
cgatgcctgt agcaatggca acaacgttgc gcaaactatt aactggcgaa ctacttactc    2820
tagcttcccg gcaacaatta atagactgga tggaggcgga taaagttgca ggaccacttc    2880
tgcgctcggc ccttccggct ggctggttta ttgctgataa atctggagcc ggtgagcgtg    2940
ggtctcgcgg tatcattgca gcactggggc cagatggtaa gccctcccgt atcgtagtta    3000
tctacacgac ggggagtcag gcaactatgg atgaacgaaa tagacagatc gctgagatag    3060
gtgcctcact gattaagcat tggtaactgt cagaccaagt ttactcatat atactttaga    3120
ttgatttaaa acttcatttt taatttaaaa ggatctaggt gaagatcctt tttgataatc    3180
tcatgaccaa aatcccttaa cgtgagtttt cgttccactg agcgtcagac cccgtagaaa    3240
agatcaaagg atcttcttga gatcctttt ttctgcgcgt aatctgctgc ttgcaaacaa    3300
aaaaaccacc gctaccagcg gtggtttgtt tgccggatca agagctacca actctttttc    3360
cgaaggtaac tggcttcagc agagcgcaga taccaaatac tgtccttcta gtgtagccgt    3420
agttaggcca ccacttcaag aactctgtag caccgcctac atacctcgct ctgctaatcc    3480
tgttaccagt ggctgctgcc agtggcgata agtcgtgtct taccgggttg gactcaagac    3540
gatagttacc ggataaggcg cagcggtcgg gctgaacggg gggttcgtgc acacagccca    3600
gcttggagcg aacgacctac accgaactga gatacctaca gcgtgagcta tgagaaagcg    3660
ccacgcttcc cgaagggaga aaggcggaca ggtatccggt aagcggcagg gtcggaacag    3720
gagagcgcac gagggagctt ccaggggaa acgcctggta tctttatagt cctgtcgggt     3780
ttcgccacct ctgacttgag cgtcgatttt tgtgatgctc gtcaggggg cggagcctat     3840 ggaaaaacgc cagcaacgcg gcctttttac ggttcctggc cttttgctgg cttttgctc     3900 acatgttctt tcctgcgtta tcccctgatt ctgtggataa ccgtattacc gcctttgagt    3960
gagctgatac cgctcgccgc agccgaacga ccgagcgcag cgagtcagtg agcgaggaag    4020
cggaagagcg cccaatacgc aaaccgcctc tccccgcgcg ttggccgatt cattaatgca    4080
gctggcacga caggtttccc gactggaaag cgggcagtga gcgcaacgca attaatgtga    4140
```

```
gttagctcac tcattaggca ccccaggctt tacactttat gcttccggct cgtatgttgt    4200
gtggaattgt gagcggataa caatttcaca caggaaacag ctatgaccat gattacgcca    4260
agctctaggt cttaattaag aagatatccc atagagccca ccgcatcccc agcatgcctg    4320
ctattgtctt cccaatcctc ccccttgctg tcctgcccca ccccaccccc cagaatagaa    4380
tgacacctac tcagacaatg cgatgcaatt tcctcatttt attaggaaag gacagtggga    4440
gtggcacctt ccagggtcaa ggaaggcacg ggggaggggc aaacaacaga tggctggcaa    4500
ctagaaggca cagtcgaagc ttcagctgct gcaggctcga ggagctcgtc tagaggatcg    4560
ctcgagttat cagtcggccg cgaagttgat ctcgccgttg ttgaacttcc tcctcacctc    4620
ctccagggtc agggtgccgg ccttgatcat ctcgccgccg atcaggagct cctccacgga    4680
cagcacggcg ccgttgcagt tggtgatgtg gttcagcctg gtcagctggg ccttgtagtt    4740
gcccttgaag tggccggaca cgaacaggaa cttgaactcg gtcacgctgg aggggtacac    4800
cttccaccac tcgttggggt tgatgtgctt gttcctggtc tggttctcct ccacgtacct    4860
ctgcatttcg tcggcctggc cgatgggcag gttgtagccg ccggagtagg ccttggtgtc    4920
cacgatcacg ccgtagtcga tgggggagcc cacggtgtag atggcgccgt cgggcttcct    4980
ggagccgccc aggtgcttgc ccctgtagcc gtacaccttc atgaagaact ccatcacctt    5040
catctccagg atacggtcct gggtgctgtt ccgggcgatc tcgatcagct cgatgtactc    5100
gtggggcacg tacttcagct tgtgcctcaa ctcggatttc ttctcctcca gctcggactt    5160
caccagctgg gaacggctga taggatcccc caatcccttt ttcactgcat ccagcgcagg    5220
acgcccgccc aggcaggcca aggcgacgag gtggtcgttg gtcaacgcgg ccaacgccgg    5280
atcagggcga gataactggg caacaatgct ctccaaagcg ggtcgccctc cgccgttact    5340
agcgattgcc acaacttgct gtggagtgag tccatgcgcc tggcagagca caggcagaag    5400
gcgctggacc gtttccaagg cttgcttccc accgccatta gaggctatgg cgaccacttg    5460
ctgtggggtc agaccgtgtg cttgacacaa gacaggcaac agagcttgaa cggtttcaag    5520
tgcctgcttt cccccaatat tggatgcgat tgcaaccact tgctcaggag tcaggccgtg    5580
tgcctgacaa agcacaggca gcaatgcctg aacggtttcc aatgcttgct tcccgccgat    5640
gttggaagca attgctacca cttgctcggg ggtgaggccg tgtgcttggc acagtaccgg    5700
cagcagccgt tggacggtct cgagagcctg tttcccgcct ccattactag cgatagccac    5760
tacttgctgg ggtgtgagcc cgtgggcttg gcaaagcaca ggaaggaggg cttgtactgt    5820
ttcgagcgcc tgcttcccgc ctatgttgga ggcgattgct accacctgct cggggggtcag   5880 tccgtgggct tgacacaaca cagggaggag agcttggaca gtttcgaggg cctgtttgcc    5940
gcctatgttt gaagcaatgg ccacgacttg ctctggtgtc aaaccgtgag cctgacagag    6000
cactgggagg agtctctgta cggtttcgag ggcttgcttg ccgcctccgt tggacgcaat    6060
ggcaacgacc tgctggggag tcaagccgtg cgcctgacaa agtacgggca acagcgcctg    6120
gaccgtttcg agagcctgct ttccgccgat attactggca atagcaacca cttgttcagg    6180
tgtaagaccg tgcgcctggc acagtactgg caacagccgt tgcacggttt ccagtgcctg    6240
cttgcccccg ccatttgagg ctatcgctac gacttgctga ggtgtcagtc cgtgcgcttg    6300
acagaggacg ggcagcagcc tttgcacagt ttccagtgct tgtttgccac cattattgga    6360
agcgatggcc acgacctgct gtggagtaag cccgtgagcc tggcaaagca cgggcagcag    6420
gcgctgcact gtctccaggg cctgtttccc tcccccgttg ctagcgatgg caaccacctg    6480
ctgaggggtc aagccgtggg cctggcacag cacagggaga agcgcctgga cagtctccag    6540
```

```
cgcctgtttc ccacctatgt tgcttgcgat cgccaccacc tgctctggcg tcaagccatg    6600
tgcttggcaa aggacgggga gcaagcgctg aacggtttcg agagcttgct tccctccatt    6660
gttggatgca attgctacta cctgctgtgg tgtcagcccg tgggcctgac aaagaactgg    6720
cagcaatcgc tgcactgttt ccaaggcctg cttaccccca tcatgacttg cgattgcgac    6780
gacctgctct ggtgtaagac catgtgcctg gcaaaggaca ggcaggagtc tctgcactgt    6840
ctcgagtgct tgtttacctc catcatgaga agcaatagcc accttgtt cgggggtcaa      6900 gttgagcggg gcacccgtca gtgcattgcg ccatgcatgc actgcctcca ctgcggtcac    6960
gccgccacgt tttgcaatct tgagaagttg gcctgtgtcc aactgtaacg gtggacctct    7020
caactctccc gccaccgtga gcaaggcctc cagagcgcgt gcgccggacc actgtttgcc    7080
gacgccaacg atcgcttcgt gtgtcgcctc tggcaacgct gcgatcatgt cctgatactt    7140
gacagcgacg gtccctaacg ctgccgggtg ttggcttaac gcaacgatgt gcgcgtgtgt    7200
aaacccgtgg ccgaccagtg cctcgtggtg ctgcgccact gtcgaacgaa ccttcggttt    7260
gatcttctcc tgttgctgct ggctgtagcc gagcgtgcgt agatcggcga tatcgatgct    7320
gtccatgtgc tgtctctcga acttggcagc ggcggtctcc ttatcgatga ccttacgttt    7380 cttttttagga tcgcccatgg tggcggcttg gcgcgtgaca cgctagtgg cgcgccgaac   7440 tagttatggt accaagttta aac                                            7463

<210> SEQ ID NO 13
<211> LENGTH: 23
<212> TYPE: DNA
<213> ORGANISM: artificial sequence
<220> FEATURE:
<223> OTHER INFORMATION: CLS_CCR5gRNA1

<400> SEQUENCE: 13
tgacatcaat tattatacat cgg                                              23

<210> SEQ ID NO 14
<211> LENGTH: 23
<212> TYPE: DNA
<213> ORGANISM: artificial sequence
<220> FEATURE:
<223> OTHER INFORMATION: CLS_CCR5gRNA2

<400> SEQUENCE: 14
tttgcttcac attgattttt tgg                                              23

<210> SEQ ID NO 15
<211> LENGTH: 23
<212> TYPE: DNA
<213> ORGANISM: artificial sequence
<220> FEATURE:
<223> OTHER INFORMATION: CLS_CCR5gRNA3

<400> SEQUENCE: 15
cttcacattg attttttggc agg                                              23

<210> SEQ ID NO 16
<211> LENGTH: 23
<212> TYPE: DNA
<213> ORGANISM: artificial sequence
<220> FEATURE:
<223> OTHER INFORMATION: CLS_CCR5gRNA4

<400> SEQUENCE: 16
ttcacattga ttttttggca ggg                                              23
```

<210> SEQ ID NO 17
<211> LENGTH: 23
<212> TYPE: DNA
<213> ORGANISM: artificial sequence
<220> FEATURE:
<223> OTHER INFORMATION: CLS_CCR5gRNA5

<400> SEQUENCE: 17
taataattga tgtcatagat tgg                                              23

<210> SEQ ID NO 18
<211> LENGTH: 19
<212> TYPE: DNA
<213> ORGANISM: artificial sequence
<220> FEATURE:
<223> OTHER INFORMATION: TALEN T1L target sequence

<400> SEQUENCE: 18
tgtgggcaac atgctggtc                                                   19

<210> SEQ ID NO 19
<211> LENGTH: 8344
<212> TYPE: DNA
<213> ORGANISM: artificial sequence
<220> FEATURE:
<223> OTHER INFORMATION: TALEN T1L plasmid sequence

<400> SEQUENCE: 19
gacgtcaggt ggcacttttc ggggaaatgt gcgcggaacc cctatttgtt tatttttcta        60
aatacattca aatatgtatc cgctcatgag acaataaccc tgataaatgc ttcaataata       120
ttgaaaaagg aagagtatga gtattcaaca tttccgtgtc gcccttattc ccttttttgc       180
ggcattttgc cttcctgttt ttgctcaccc agaaacgctg gtgaaagtaa aagatgctga       240
agatcagttg ggtgcacgag tgggttacat cgaactggat ctcaacagcg gtaagatcct       300
tgagagtttt cgccccgaag aacgttttcc aatgatgagc acttttaaag ttctgctatg       360
tggcgcggta ttatcccgta ttgacgccgg gcaagagcaa ctcggtcgcc gcatacacta       420
ttctcagaat gacttggttg agtactcacc agtcacagaa aagcatctta cggatggcat       480
gacagtaaga gaattatgca gtgctgccat aaccatgagt gataacactg cggccaactt       540
acttctgaca acgatcggag gaccgaagga gctaaccgct tttttgcaca catgggggga       600
tcatgtaact cgccttgatc gttgggaacc ggagctgaat gaagccatac caaacgacga       660
gcgtgacacc acgatgcctg tagcaatggc aacaacgttg cgcaaactat taactggcga       720
actacttact ctagcttccc ggcaacaatt aatagactgg atggaggcgg ataaagttgc       780
aggaccactt ctgcgctcgg cccttccggc tggctggttt attgctgata atctggagc        840 cggtgagcgt gggtctcgcg gtatcattgc agcactgggg ccagatggta agccctcccg       900
tatcgtagtt atctacacga cggggagtca ggcaactatg gatgaacgaa atagacagat       960
cgctgagata ggtgcctcac tgattaagca ttggtaactg tcagaccaag tttactcata      1020
tatactttag attgatttaa aacttcattt ttaatttaaa aggatctagg tgaagatcct      1080
ttttgataat ctcatgacca aaatccctta acgtgagttt tcgttccact gagcgtcaga      1140
ccccgtagaa aagatcaaag gatcttcttg agatcctttt tttctgcgcg taatctgctg      1200
cttgcaaaca aaaaaaccac cgctaccagc ggtggtttgt ttgccggatc aagagctacc      1260
aactcttttt ccgaaggtaa ctggcttcag cagagcgcag ataccaaata ctgtccttct      1320
agtgtagccg tagttaggcc accacttcaa gaactctgta gcaccgccta catacctcgc      1380

-continued

```
tctgctaatc ctgttaccag tggctgctgc cagtggcgat aagtcgtgtc ttaccgggtt    1440
ggactcaaga cgatagttac cggataaggc gcagcggtcg ggctgaacgg ggggttcgtg    1500
cacacagccc agcttggagc gaacgaccta caccgaactg agatacctac agcgtgagca    1560
ttgagaaagc gccacgcttc ccgaagggag aaaggcggac aggtatccgg taagcggcag    1620
ggtcggaaca ggagagcgca cgagggagct tccaggggga aacgcctggt atctttatag    1680
tcctgtcggg tttcgccacc tctgacttga gcgtcgattt ttgtgatgct cgtcaggggg    1740
gcggagccta tggaaaaacg ccagcaacgc ggcctttttta cggttcctgg cctttttgctg   1800 gcctttttgct cacatgttct ttcctgcgtt atccccctgat tctgtggata accgtattac    1860
cgcctttgag tgagctgata ccgctcgccg cagccgaacg accgagcgca gcgagtcagt    1920
gagcgaggaa gcggaagagc gcccaatacg caaaccgcct ctccccgcgc gttggccgat    1980
tcattaatgc agctggcacg acaggtttcc cgactggaaa gcgggcagtg agcgcaacgc    2040
aattaatgtg agttagctca ctcattaggc accccaggct ttacacttta tgcttccggc    2100
tcgtatgttg tgtggaattg tgagcggata acaatttcac acaggaaaca gctatgacca    2160
tgattacgcc aagctctagc tagaggtcga cggtatacag acatgataag atacattgat    2220
gagtttggac aaaccacaac tagaatgcag tgaaaaaaat gctttatttg tgaaatttgt    2280
gatgctattg ctttatttgt aaccattata agctgcaata acaagttgg ggtgggcgaa     2340 gaactccagc atgagatccc cgcgctggag gatcatccag ccggcgtccc ggaaaacgat    2400
tccgaagccc aacctttcat agaaggcggc ggtggaatcg aaatctcgta gcacgtgtca    2460
gtcctgctcc tcggccacga agtgcttagc cctcccacac ataaccagag ggcagcaatt    2520
cacgaatccc aactgccgtc ggctgtccat cactgtcctt cactatcgct ttgatcccag    2580
gatgcagatc gagaagcacc tgtcgacacc gtccgcaggg gctcaagatg cccctgttct    2640
catttccgat cgcgacgata caagtcaggt tgccagctgc cgcagcagca gcagtgccca    2700
gcaccacgag ttctgcacaa ggtccccccag taaaatgata tacattgaca ccagtgaaga    2760
tgcggccgtc gctagagaga gctgcgctgg cgacgctgta gtcttcagag atggggatgc    2820
tgttgattgt agccgttgct ctttcaatga gggtggattc ttcttgagac aaaggcttgg    2880
ccatggttta gttcctcacc ttgtcgtatt atactatgcc gatatactat gccgatgatt    2940
aattgtcaac acgtgctgat cagatccgaa aatggatata caagctcccg ggagcttttt    3000
gcaaaagcct aggcctccaa aaaagcctcc tcactacttc tggaatagct cagaggcaga    3060
ggcggcctcg gcctctgcat aaataaaaaa aattagtcag ccatggggcg gagaatgggc    3120
ggaactgggc ggagttaggg gcgggatggg cggagttagg ggcgggacta tggttgctga    3180
ctaattgaga tgcatgcttt gcatacttct gcctgctggg gagcctgggg actttccaca    3240
cctggttgct gactaattga gatgcatgct ttgcatactt ctgcctgcct ggggagcctg    3300
gggactttcc acaccctaac tgacacacat tccacagaat taattcgcgt taaatttttg    3360
ttaaatcagc tcattttttta accaataggc cgaaatcccc aaaatccctt ataaatcaaa    3420
agaatagacc gagataggt tgagtgttgt tccagtttgg aacaagagtc cactattaaa    3480
gaacgtggac tccaacgtca aagggcgaaa aacgtctat cagggcgatg gcccactacg    3540
tgaaccatca ccctaatcaa gttttttggg gtcgaggtgc cgtaaagcac taaatcggaa    3600
ccctaaaggg atgccccgat ttagagcttg acggggaaag ccggcgaacg tggcgagaaa    3660
ggaagggaag aaagcgaaag gagcgggcgc tagggcgctg gcaagtgtag cggtcacgct    3720
gcgcgtaacc accacacccg ccgcgcttaa tgcgccgcta cagggcgcgt ggggatacccc   3780
```

```
cctagagccc cagctggttc tttccgcctc agaagccata gagcccaccg catccccagc    3840
atgcctgcta ttgtcttccc aatcctcccc cttgctgtcc tgcccaccc caccccccag    3900
aatagaatga cacctactca gacaatgcga tgcaatttcc tcattttatt aggaaaggac    3960
agtgggagtg gcaccttcca gggtcaagga aggcacgggg gaggggcaaa caacagatgg    4020
ctggcaacta gaaggcacag tcgaggctga tcagcgggtt taaactcaat ggtgatggtg    4080
atgatgaccg gtacgcgtag aatcgagacc gaggagaggg ttagggatag gcttaccttc    4140
gaagggccct taaaagttta tctcgccgtt attaaatttc cgtctcactt cctctaaggt    4200
taatgtgccg gctttaatca tttctccacc aattaaaagc tcttctacac taagaacagc    4260
tccattacaa ttagtgatat gatttaatcg tgtaagctga gctttgtagt ttcctttaaa    4320
gtgaccactc acaaataaaa acttaaattc cgttacagaa gatggataga cttttccacca   4380
ttcattaggg ttgatatgtt tgtttcgtgt ttgattttct tcgacatatc gttgcatttc    4440
atctgcttgg ccaattggca gattataacc tccgctataa gctttagtat ccacgatcac    4500
accgtaatca ataggagatc cgacagtata aattgctccg tccggtttcc ttgatccacc    4560
caaatgttta cctctatatc cataaacttt cataaaaaat tccattacct tcatttcaag    4620
aattctatcc tgagtggaat ttctggcaat ttcaattaat tcaatatatt catgaggcac    4680
atatttcaat ttatgacgaa gttcagattt cttctcctcc agttcacttt tgactagttg    4740
ggatccacta gtagtcaacg tgatcaaggc cggcgcgtgc ggcaatccct ttttcactgc    4800
atccagcgca ggacgtccgc cgaggcaggc caaggcgacg aggtggtcgt tggtcaacgc    4860
ggccaacgcc ggatcagggc gagataactg ggcaacaatg ctctccagcg ccggcctgcc    4920
gccgccattg ctggcgatgg ccaccacctg ctggggtgtc aggccatggg cctggcacag    4980
caccggcaac agcgcctgca ccgtctccag cgcctgcttg ccgccgccat tgctggcgat    5040
ggccaccacc tgctgcgggg tcaggccatg ggcctggcac agcaccggca acagccgctg    5100
caccgtctcc agcgcctgct tgcccccatt attgctggcg atggccacca cctgctccgg    5160
ggtcaggcca tgggcctggc acagcaccgg caacagccgc tgcaccgtct ccagagcctg    5220
cttgccacca atattgctgg cgatggccac cacctgctcc ggggtcaggc catgggcctg    5280
gcacagcacc ggcaacagcc gctgcaccgt ctcaagcgcc tgcttgccac cgtcgtggct    5340
ggcgatggcc accacctgct ccggggtcag gccatgggcc tggcacagca ccggcaacag    5400
ccgctggaca gtctccagcg cctgcttgcc accattattg ctggcgatgg ccaccacctg    5460
ctccggggtc aggccatggg cctggcacag caccggcaac aatcgctgca ccgtctccag    5520
cgcctgcttg ccaccgccat tgctggcgat ggccaccacc tgctgcgggg tcaggccatg    5580
ggcctggcac agcaccggaa gcagccgctg caccgtctcc agcgcctgct tgccaccgcc    5640
attgctggcg atcgctacca cctgctgggg tgtcaggcca tgggcctggc acagcaccgg    5700
caacagccgc tgcaccgtct ccagcgcctg cttgccaccg ccattgctgg cgatggctac    5760
cacctgttgc ggggtcaggc catgggcctg gcacagcacc ggcaacagcc gctgcaccgt    5820
ctccagcgcc tgcttgccac cgccattgct ggcgattgcc accacctgct ccggggtcag    5880
gccatgggcc tggcacagca ccggcaacag cgcctgcacc gtctccagcg cctgcttgcc    5940
accgtcgtgg cttgcgatgg ccaccacctg ctccggggtc aggccatggg cctggcacag    6000
caccggcaac agcgcctgca ccgtctccag cgcctgcttg ccgccgtcgt ggctggcgat    6060
ggccaccacc tgctgcgggg tcaggccatg ggcctggcac agcaccggca acagccgctg    6120
```

-continued

```
caccgtctcc agcgcctgct tgcccccatt attgctggcg atggccacca cctgctccgg    6180
ggtcaggcca tgggcctggc acagcaccgg caacagccgc tgcaccgtct ccagagcctg    6240
cttgccacca atattgctgg cgatggccac cacctgctcc ggggtcaggc catgggcctg    6300
gcacagcacc ggcaacagcc gctgcaccgt ctcaagcgcc tgcttgccac cgtcgtggct    6360
ggcgatggcc accacctgct ccggggtcag gccatgggcc tggcacagca ccggcaacag    6420
ccgctggaca gtctccagcg cctgcttgcc accgccattg ctggcgatgg ccaccacctg    6480
ctccggggtc aggccatggg cctggcacag caccggcaac aatcgctgca ccgtctccag    6540
cgcctgcttg ccaccgccat tgctggcgat ggccaccacc tgctgcgggg tcaggccatg    6600
ggcctggcac agcaccggaa gcagccgctg caccgtctcc agcgcctgct tgccgccatc    6660
gtggctggcg atggccacca cctgctgcgg cgtaaggttc agggggcac ccgtcagtgc    6720
attgcgccat gcatgcactg cctccactgc ggtcacgccg ccacgttttg caatcttgag    6780
aagttggcct gtgtccaact gtaacggtgg acctctcaac tctcccgcca ccgtgagcaa    6840
ggcctccaga gcgcgtgcgc cggaccactg tttgccgacg ccaacgatcg cttcgtgtgt    6900
cgcctctggc aacgctgcga tcatgtcctg atacttgaca gcgacggtcc ctaacgctgc    6960
cgggtgttgg ctgagcgcaa cgatgtgcgc gtgtgtaaac ccatggccga ccagtgcctc    7020
gtggtgctgc gccactgtcg aacgaacctt cggtttgatc ttctcctgtt gctgctggct    7080
gtagccgagc gtgcgtagat ccacctgcgc ggccggcgaa gcgtcggagg gttgcgcagc    7140
acgtcgtcgc ggcgccagat ctaagctagc gtggatgccc actttccgct ttttcttggg    7200
tctagaggcg tagtcaggca cgtcgtaagg gtagcccatc ctagacacct gtggagagaa    7260
aggcaaagtg gatgttattc tatagtgtca cctaaatcgt atgtgtatga tacataaggt    7320
tatgtattaa ttgtagccgc gttctaacga agccaagggg gtgggccata gactctatag    7380
gcggtactta cgtcactctt ggcacgggga atccgcgttc caatgcaccg ttcccggccg    7440
cggaggctgg atcggtcccg gtgtcttcta tggaggtcaa aacagcgtgg atggcgtctc    7500
caggcgatct gacggttcac taaacgagct ctgcttatat agacctccca ccgtacacgg    7560
ctaccgccca tttgcgtcaa tggggcggag ttgttacgac attttggaaa gtgccgttga    7620
ttttggtgcc aaaacaaact cccattgacg tcaatgggt ggagacttgg aaatccccgt    7680
gagtcaaacc gctatccacg cccattgatg tactgccaaa accgcatcac catggtaata    7740
gcgatgacta atacgtagat gtactgccaa gtaggaaagt cccataaggt catgtactgg    7800
gcataatgcc aggcgggcca tttaccgtca ttgacgtcaa taggggcgt acttggcata    7860
tgatacactt gatgtactgc caagtgggca gtttaccgta aatagtccac ccattgacgt    7920
caatggaaag tccctattgg cgttactatg ggaacatacg tcattattga cgtcaatggg    7980
cggggtcgt tgggcggtca gccaggcggg ccatttaccg taagttatgt aacgcggaac    8040
tccatatatg gctatgaac taatgacccc gtaattgatt actattaata actagtcaat    8100
aatcaatgtc aacgcgtata tctggcccgt acatcgcgaa gcagcgcaaa acgcctaacc    8160
ctaagcagat tcttcatgca attgtcggtc aagccttgcc ttgttgtagc ttaaattttg    8220
ctcgcgcact actcagcgac ctccaacaca caagcaggga gcagatactg gcttaactat    8280
gcggcatcag agcagattgt actgagagtc gaccataggg gatcgggaga tctcccgatc    8340
cgtc                                                                8344
```

<210> SEQ ID NO 20
<211> LENGTH: 19
<212> TYPE: DNA
<213> ORGANISM: artificial sequence
<220> FEATURE:
<223> OTHER INFORMATION: TALEN T1R target sequence

<400> SEQUENCE: 20
tcttcagcct tttgcagtt                                              19

<210> SEQ ID NO 21
<211> LENGTH: 7120
<212> TYPE: DNA
<213> ORGANISM: artificial sequence
<220> FEATURE:
<223> OTHER INFORMATION: TALEN T1R plasmid sequence

<400> SEQUENCE: 21

```
gacgtcaggt ggcactttc gggaaatgt gcgcggaacc cctatttgtt tattttctat     60
aatacattca aatatgtatc cgctcatgag acaataaccc tgataaatgc ttcaataata    120
ttgaaaaagg aagagtatga gtattcaaca tttccgtgtc gcccttattc ccttttttgc    180
ggcattttgc cttcctgttt ttgctcaccc agaaacgctg gtgaaagtaa agatgctga    240 agatcagttg ggtgcacgag tgggttacat cgaactggat ctcaacagcg gtaagatcct    300
tgagagtttt cgccccgaag aacgttttcc aatgatgagc acttttaaag ttctgctatg    360
tggcgcggta ttatcccgta ttgacgccgg gcaagagcaa ctcggtcgcc gcatacacta    420
ttctcagaat gacttggttg agtactcacc agtcacagaa aagcatctta cggatggcat    480
gacagtaaga gaattatgca gtgctgccat aaccatgagt gataacactg cggccaactt    540
acttctgaca acgatcggag gaccgaagga gctaaccgct tttttgcaca acatggggga    600
tcatgtaact cgccttgatc gttgggaacc ggagctgaat gaagccatac caaacgacga    660
gcgtgacacc acgatgcctg tagcaatggc aacaacgttg cgcaaactat taactggcga    720
actacttact ctagcttccc ggcaacaatt aatagactgg atggaggcgg ataaagttgc    780
aggaccactt ctgcgctcgg cccttccggc tggctggttt attgctgata atctggagc    840 cggtgagcgt gggtctcgcg gtatcattgc agcactgggg ccagatggta gccctcccg    900 tatcgtagtt atctacacga cggggagtca ggcaactatg gatgaacgaa atagacagat    960
cgctgagata ggtgcctcac tgattaagca ttggtaactg tcagaccaag tttactcata   1020
tatactttag attgatttaa aacttcattt ttaatttaaa aggatctagg tgaagatcct   1080
ttttgataat ctcatgacca aaatccctta acgtgagttt tcgttccact gagcgtcaga   1140
ccccgtagaa aagatcaaag gatcttcttg agatcctttt tttctgcgcg taatctgctg   1200
cttgcaaaca aaaaaaccac cgctaccagc ggtggtttgt ttgccggatc aagagctacc   1260
aactcttttt ccgaaggtaa ctggcttcag cagagcgcag ataccaaata ctgtccttct   1320
agtgtagccg tagttaggcc accacttcaa gaactctgta gcaccgccta catacctcgc   1380
tctgctaatc ctgttaccag tggctgctgc cagtggcgat aagtcgtgtc ttaccgggtt   1440
ggactcaaga cgatagttac cggataaggc gcagcggtcg ggctgaacgg ggggttcgtg   1500
cacacagccc agcttggagc gaacgaccta caccgaactg agatacctac agcgtgagca   1560
ttgagaaagc gccacgcttc ccgaagggag aaaggcggac aggtatccgg taagcggcag   1620
ggtcggaaca ggagagcgca cgagggagct tccaggggga aacgcctggt atctttatag   1680
tcctgtcggg tttcgccacc tctgacttga gcgtcgattt ttgtgatgct cgtcaggggg   1740
```

```
gcggagccta tggaaaaacg ccagcaacgc ggccttttta cggttcctgg ccttttgctg   1800
gccttttgct cacatgttct ttcctgcgtt atcccctgat tctgtggata accgtattac   1860
cgcctttgag tgagctgata ccgctcgccg cagccgaacg accgagcgca gcgagtcagt   1920
gagcgaggaa gcggaagagc gcccaatacg caaaccgcct ctccccgcgc gttggccgat   1980
tcattaatgc agctggcacg acaggtttcc cgactggaaa gcgggcagtg agcgcaacgc   2040
aattaatgtg agttagctca ctcattaggc accccaggct ttacacttta tgcttccggc   2100
tcgtatgttg tgtggaattg tgagcggata acaatttcac acaggaaaca gctatgacca   2160
tgattacgcc aagctctagc tagaggtcga cggtatacag acatgataag atacattgat   2220
gagtttggac aaaccacaac tagaatgcag tgaaaaaaat gctttatttg tgaaatttgt   2280
gatgctattg ctttatttgt aaccattata agctgcaata acaagttggg gtgggcgaa    2340 gaactccagc atgagatccc cgcgctggag gatcatccag ccggcgtccc ggaaaacgat   2400
tccgaagccc aacctttcat agaaggcggc ggtggaatcg aaatctcgta gcacgtgtca   2460
gtcctgctcc tcggccacga agtgcttagc cctcccacac ataaccagag ggcagcaatt   2520
cacgaatccc aactgccgtc ggctgtccat cactgtcctt cactatcgct ttgatcccag   2580
gatgcagatc gagaagcacc tgtcgacacc gtccgcaggg gctcaagatg cccctgttct   2640
catttccgat cgcgacgata caagtcaggt tgccagctgc cgcagcagca gcagtgccca   2700
gcaccacgag ttctgcacaa ggtcccccag taaaatgata tacattgaca ccagtgaaga   2760
tgcggccgtc gctagagaga gctgcgctgg cgacgctgta gtcttcagag atggggatgc   2820
tgttgattgt agccgttgct ctttcaatga gggtggattc ttcttgagac aaaggcttgg   2880
ccatggttta gttcctcacc ttgtcgtatt atactatgcc gatatactat gccgatgatt   2940
aattgtcaac acgtgctgat cagatccgaa atggatata caagctcccg ggagcttttt    3000
gcaaaagcct aggcctccaa aaaagcctcc tcactacttc tggaatagct cagaggcaga   3060
ggcggcctcg gcctctgcat aaataaaaaa aattagtcag ccatggggcg gagaatgggc   3120
ggaactgggc ggagttaggg gcgggatggg cggagttagg ggcgggacta tggttgctga   3180
ctaattgaga tgcatgcttt gcatacttct gcctgctggg gagcctgggg actttccaca   3240
cctggttgct gactaattga gatgcatgct ttgcatactt ctgcctgcct ggggagcctg   3300 gggacttttcc acaccctaac tgacacacat tccacagaat taattcgcgt taaattttg    3360 ttaaatcagc tcatttttta accaataggc cgaaatcccc aaaatccctt ataaatcaaa   3420
agaatagacc gagatagggt tgagtgttgt tccagtttgg aacaagagtc cactattaaa   3480
gaacgtggac tccaacgtca aagggcgaaa accgtctat cagggcgatg cccactacg    3540 tgaaccatca ccctaatcaa gttttttggg gtcgaggtgc cgtaaagcac taaatcggaa   3600
ccctaaaggg atgccccgat ttagagcttg acggggaaag ccggcgaacg tggcgagaaa   3660
ggaagggaag aaagcgaaag gagcgggcgc tagggcgctg gcaagtgtag cggtcacgct   3720
gcgcgtaacc accacacccg ccgcgcttaa tgcgccgcta cagggcgcgt ggggatacc    3780 cctagagccc cagctggttc tttccgcctc agaagccata gagcccaccg catcccagc    3840 atgcctgcta ttgtcttccc aatcctcccc cttgctgtcc tgcccaccc cacccccag    3900 aatagaatga cacctactca gacaatgcga tgcaatttcc tcattttatt aggaaaggac   3960
agtgggagtg gcaccttcca gggtcaagga aggcacgggg gagggcaaa caacagatgg   4020 ctggcaacta gaaggcacag tcgaggctga tcagcgggtt taaactcaat ggtgatggtg   4080
atgatgaccg gtacgcgtag aatcgagacc gaggagaggg ttagggatag gcttaccttc   4140
```

```
gaagggccct taaaagttta tctcgccgtt attaaatttc cgtctcactt cctctaaggt   4200
taatgtgccg gctttaatca tttctccacc aattaaaagc tcttctacac taagaacagc   4260
tccattacaa ttagtgatat gatttaatcg tgtaagctga gctttgtagt ttcctttaaa   4320
gtgaccactc acaaataaaa acttaaattc cgttacagaa gatggataga ctttccacca   4380
ttcattaggg ttgatatgtt tgtttcgtgt ttgattttct tcgacatatc gttgcatttc   4440
atctgcttgg ccaattggca gattataacc tccgctataa gctttagtat ccacgatcac   4500
accgtaatca ataggagatc cgacagtata aattgctccg tccggtttcc ttgatccacc   4560
caaatgttta cctctatatc cataaacttt cataaaaaat tccattacct tcatttcaag   4620
aattctatcc tgagtggaat ttctggcaat ttcaattaat tcaatatatt catgaggcac   4680
atatttcaat ttatgacgaa gttcagattt cttctcctcc agttcacttt tgactagttg   4740
ggatccacta gtagtcaacg tgatcaaggc cggcgcgtgc ggcaatccct ttttcactgc   4800
atccagcgca ggacgtccgc cgaggcaggc caaggcgacg aggtggtcgt tggtcaacgc   4860
ggccaacgcc ggatcagggc gagataactg gcaacaatg ctctccagcg ccggcctgcc   4920
gccgccattg ctggcgatgg ccaccacctg ctggggtgtc aggccatggg cctggcacag   4980
caccggcaac agcgcctgca ccgtctccag cgcctgcttg ccgccgccat tgctggcgat   5040
ggccaccacc tgctgcgggg tcaggccatg ggcctggcac agcaccggca acagccgctg   5100
caccgtctcc agcgcctgct tgcccccatt attgctggcg atggccacca cctgctccgg   5160
ggtcaggcca tgggcctggc acagcaccgg caacagccgc tgcaccgtct ccagagcctg   5220
cttgccacca atattgctgg cgatggccac cacctgctcc ggggtcaggc catgggcctg   5280
gcacagcacc ggcaacagcc gctgcaccgt ctcaagcgcc tgcttgccac cgtcgtggct   5340
ggcgatggcc accacctgct ccggggtcag gccatgggcc tggcacagca ccggcaacag   5400
ccgctggaca gtctccagcg cctgcttgcc accattattg ctggcgatgg ccaccacctg   5460
ctccggggtc aggccatggg cctggcacag caccggcaac aatcgctgca ccgtctccag   5520
cgcctgcttg ccaccgccat tgctggcgat ggccaccacc tgctgcgggg tcaggccatg   5580
ggcctggcac agcaccggaa gcagccgctg caccgtctcc agcgcctgct tgccaccgcc   5640
attgctggcg atcgctacca cctgctgggg tgtcaggcca tgggcctggc acagcaccgg   5700
caacagccgc tgcaccgtct ccagcgcctg cttgccaccg ccattgctgg cgatggctac   5760
cacctgttgc ggggtcaggc catgggcctg gcacagcacc ggcaacagcc gctgcaccgt   5820
ctccagcgcc tgcttgccac cgccattgct ggcgattgcc accacctgct ccggggtcag   5880
gccatgggcc tggcacagca ccggcaacag cgcctgcacc gtctccagcg cctgcttgcc   5940
accgtcgtgg cttgcgatgg ccaccacctg ctccggggtc aggccatggg cctggcacag   6000
caccggcaac agcgcctgca ccgtctccag cgcctgcttg ccgccgtcgt ggctggcgat   6060
ggccaccacc tgctgcgggg tcaggccatg ggcctggcac agcaccggca acagccgctg   6120
caccgtctcc agcgcctgct tgcccccatt attgctggcg atggccacca cctgctccgg   6180
ggtcaggcca tgggcctggc acagcaccgg caacagccgc tgcaccgtct ccagagcctg   6240
cttgccacca atattgctgg cgatggccac cacctgctcc ggggtcaggc catgggcctg   6300
gcacagcacc ggcaacagcc gctgcaccgt ctcaagcgcc tgcttgccac cgtcgtggct   6360
ggcgatggcc accacctgct ccggggtcag gccatgggcc tggcacagca ccggcaacag   6420
ccgctggaca gtctccagcg cctgcttgcc accgccattg ctggcgatgg ccaccacctg   6480
ctccggggtc aggccatggg cctggcacag caccggcaac aatcgctgca ccgtctccag   6540
```

| | |
|---|---|
| cgcctgcttg ccaccgccat tgctggcgat ggccaccacc tgctgcgggg tcaggccatg | 6600 |
| ggcctggcac agcaccggaa gcagccgctg caccgtctcc agcgcctgct tgccgccatc | 6660 |
| gtggctggcg atggccacca cctgctgcgg cgtaaggttc agggggggcac ccgtcagtgc | 6720 |
| attgcgccat gcatgcactg cctccactgc ggtcacgccg ccacgttttg caatcttgag | 6780 |
| aagttggcct gtgtccaact gtaacggtgg acctctcaac tctcccgcca ccgtgagcaa | 6840 |
| ggcctccaga gcgcgtgcgc cggaccactg tttgccgacg ccaacgatcg cttcgtgtgt | 6900 |
| cgcctctggc aacgctgcga tcatgtcctg atacttgaca gcgacggtcc ctaacgctgc | 6960 |
| cgggtgttgg ctgagcgcaa cgatgtgcgc gtgtgtaaac ccatggccga ccagtgcctc | 7020 |
| gtggtgctgc gccactgtcg aacgaacctt cggtttgatc ttctcctgtt gctgctggct | 7080 |
| gtagccgagc gtgcgtagat ccacctgcgc ggccggcgaa | 7120 |

<210> SEQ ID NO 22
<211> LENGTH: 19
<212> TYPE: DNA
<213> ORGANISM: artificial sequence
<220> FEATURE:
<223> OTHER INFORMATION: TALEN T2L target sequence

<400> SEQUENCE: 22

| | |
|---|---|
| tttgtgggca acatgctgg | 19 |

<210> SEQ ID NO 23
<211> LENGTH: 5885
<212> TYPE: DNA
<213> ORGANISM: artificial sequence
<220> FEATURE:
<223> OTHER INFORMATION: TALEN T2L plasmid sequence

<400> SEQUENCE: 23

| | |
|---|---|
| aagaacatgt gagcaaaagg ccagcaaaag cccaggaacc gtaaaaaggc cgcgttgctg | 60 |
| gcgtttttcc ataggctccg ccccctgac gagcatcaca aaaatcgacg ctcaagtcag | 120 |
| aggtggcgaa acccgacagg actataaaga taccaggcgt ttccccctgg aagctccctc | 180 |
| gtgcgctctc ctgttccgac cctgccgctt accggatacc tgtccgcctt ctcccttcg | 240 |
| ggaagcgtgg cgctttctca tagctcacgc tgtaggtatc tcagttcggt gtaggtcgtt | 300 |
| cgctccaagc tgggctgtgt gcacgaaccc ccgttcagc ccgaccgctg cgccttatcc | 360 |
| ggtaactatc gtcttgagtc aacccggta agacacgact tatcgccact ggcagcagcc | 420 |
| actggtaaca ggattagcag agcgaggtat gtaggcggtg ctacagagtt cttgaagtgg | 480 |
| tggcctaact acggctacac tagaaggaca gtatttggta tctgcgctct gctgaagcca | 540 |
| gttaccttcg gaaaaagagt tggtagctct tgatccggca acaaaccac cgctggtagc | 600 |
| ggtggttttt ttgtttgcaa gcagcagatt acgcgcagaa aaaaggatc tcaagaagat | 660 |
| cctttgatct tttctacggg gtctgacgct cagtggaacg aaaactcacg ttaagggatt | 720 |
| ttggtcatga gattatcaaa aaggatcttc acctagatcc ttttaaatta aaaatgaagt | 780 |
| tttagcacgt gctattattg aagcatttat caggggttatt gtctcatgag cggatacata | 840 |
| tttgaatgta tttagaaaaa taaacaaata ggggttccgc gcacatttcc ccgaaaagtg | 900 |
| ccacctgtat gcggtgtgaa ataccgcaca gatgcgtaag gagaaaatac cgcatcagga | 960 |
| aattgtaagc gttaataatt cagaagaact cgtcaagaag gcgatagaag gcgatgcgct | 1020 |
| gcgaatcggg agcggcgata ccgtaaagca cgaggaagcg gtcagcccat tcgccgccaa | 1080 |
| gctcttcagc aatatcacgg gtagccaacg ctatgtcctg atagcggtcc gccacaccca | 1140 |

```
gccggccaca gtcgatgaat ccagaaaagc ggccattttc caccatgata ttcggcaagc    1200
aggcatcgcc atgggtcacg acgagatcct cgccgtcggg catgctcgcc ttgagcctgg    1260
cgaacagttc ggctggcgcg agcccctgat gctcttcgtc cagatcatcc tgatcgacaa    1320
gaccggcttc catccgagta cgtgctcgct cgatgcgatg tttcgcttgg tggtcgaatg    1380
ggcaggtagc cggatcaagc gtatgcagcc gccgcattgc atcagccatg atggatactt    1440
tctcggcagg agcaaggtga gatgacagga gatcctgccc cggcacttcg cccaatagca    1500
gccagtccct tcccgcttca gtgacaacgt cgagcacagc tgcgcaagga acgcccgtcg    1560
tggccagcca cgatagccgc gctgcctcgt cttgcagttc attcagggca ccggacaggt    1620
cggtcttgac aaaaagaacc gggcgcccct gcgctgacag ccggaacacg gcggcatcag    1680
agcagccgat tgtctgttgt gcccagtcat agccgaatag cctctccacc caagcggccg    1740
gagaacctgc gtgcaatcca tcttgttcaa tcatgcgaaa cgatcctcat cctgtctctt    1800
gatcagagct tgatccctg cgccatcaga tccttggcgg cgagaaagcc atccagttta    1860 cttttgcaggg cttcccaacc ttaccagagg gcgcccagc tggcaattcc ggttcgcttg    1920
ctgtccataa aaccgcccag tagaagcca agagcccacc gcatcccag catgcctgct    1980 attttcttcc caatcctccc ccttgctgtc ctgcccacc ccaccccca gaatagaatg    2040 acacctactc agacaatgcg atgcaatttc ctcattttat taggaaagga cagtgggagt    2100
ggcaccttcc agggtcaagg aaggcacggg ggaggggcaa acaacagatg ctggcaact    2160 agaaggcaca gtcgaggctg atcagcgggt ttaaacgggc ccttaaaagt ttatctcgcc    2220
gttattaaat ttccgtctca cttcctctaa ggttaatgtg ccggctttaa tcatttctcc    2280
accaattaaa agctcttcta cactaagaac agctccatta caattagtga tatgatttaa    2340
tcgtgtaagc tgagctttgt agtttccttt aaagtgacca ctcacaaata aaaacttaaa    2400
ttccgttaca gaagatggat agactttcca ccattcatta gggttgatat gtttgtttcg    2460
tgtttgattt tcttcgacat atcgttgcat ttcatctgct tggccaattg gcagattata    2520
acctccgcta taagctttag tatccacgat cacaccgtaa tcaataggag atccgacagt    2580
ataaattgct ccgtccggtt tccttgatcc acccaaatgt ttacctctat atccataaac    2640
tttcataaaa aattccatta ccttcatttc aagaattcta tcctgagtgg aatttctggc    2700
aatttcaatt aattcaatat attcatgagg cacatatttc aatttatgac gaagttcaga    2760
tttcttctcc tccagttcac ttttgactag ttgggatcct gtcagggcgg ccagagctgg    2820
gtcgggtctg ctcagctggg ccacaataga ttccagggcg gtctgcctc ccttgttgct    2880 ggcaatggcc acgacctgct ggggtgtcag gccatgggcc tggcacagca ccggcaacag    2940
cgcctgcacc gtctccagcg cctgcttgcc gccattattg ctggcgatgg ccaccacctg    3000
ctgcggggtc aggccatggg cctggcacag caccggcaac agccgctgca ccgtctccag    3060
cgcctgcttg cccccgccat tgctggcgat ggccaccacc tgctccgggg tcaggccatg    3120
ggcctggcac agcaccggca acagccgctg caccgtctcc agagcctgct tgccaccgtc    3180
gtggctggcg atggccacca cctgctgcgg ggtcaggcca tgggcctggc acagcaccgg    3240
caacagccgc tgcaccgtct caagcgcctg cttgccacca ttattgctgg cgatggccac    3300
cacctgctcc ggggtcaggc catgggcctg gcacagcacc ggcaacagcc gctggacagt    3360
ctccagcgcc tgcttgccac cgccattgct ggcgatggcc accacctgct ccggggtcag    3420
gccatgggcc tggcacagca ccggcaacaa tcgctgcacc gtctccagcg cctgcttgcc    3480
accaatattg ctggcgatgg ccaccacctg ctccggggtc aggccatggg cctggcacag    3540
```

```
caccggaagc agccgctgca ccgtctccag cgcctgcttg ccaccgtcgt ggctggcgat    3600
cgctaccacc tgctggggtg tcaggccatg ggcctggcac agcaccggca acagccgctg    3660
caccgtctcc agcgcctgct tgccaccaat attgctggcg atggctacca cctgttgcgg    3720
ggtcaggcca tgggcctggc acagcaccgg caacagccgc tgcaccgtct ccagcgcctg    3780
cttgccacca atattgctgg cgattgccac cacctgctcc ggggtcaggc catgggcctg    3840
gcacagcacc ggcaacagcg cctgcaccgt ctccagcgcc tgcttgccac cgtcgtggct    3900
tgcgatggcc accacctgct ccggggtcag gccatgggcc tggcacagca ccggcaacag    3960
cgcctgcacc gtctccagcg cctgcttgcc gccattattg ctggcgatgg ccaccacctg    4020
ctgcggggtc aggccatggg cctggcacag caccggcaac agccgctgca ccgtctccag    4080
cgcctgcttg ccccattat tgctggcgat ggccaccacc tgctccgggg tcaggccatg    4140
ggcctggcac agcaccggca acagccgctg caccgtctcc agagcctgct tgccaccatt    4200
attgctggcg atggccacca cctgctgcgg gtcaggcca tgggcctggc acagcaccgg    4260
caacagccgc tgcaccgtct caagcgcctg cttgccaccg ccattgctgg cgatggccac    4320
cacctgctcc ggggtcaggc catgggcctg gcacagcacc ggcaacagcc gctggacagt    4380
ctccagcgcc tgcttgccac cattattgct ggcgatggcc accacctgct ccggggtcag    4440
gccatgggcc tggcacagca ccggcaacaa tcgctgcacc gtctccagcg cctgcttgcc    4500
accgccattg ctggcgatgg ccaccacctg ctgcggggtc aggccatggg cctggcacag    4560
caccggaagc agccgctgca ccgtctccag cgcctgcttg ccaccgccat tgctggcgat    4620
ggccaccacc tgctgcggcg taaggttcag gggagcgcct gtcagggcat tccgccaagc    4680
gtgcacggct tccacggctg tcacgcctcc ccgcttggcg atcttcagca gctggccggt    4740
gtccagctgc agtggagggc ctctcagctc gccggccact gtcagcaagg cctcgagtgc    4800
tctagcgccg gaccactgct tgcccacgcc cacgatagcc tcgtgtgtgg cctcgggcag    4860
ggcggcgatc atgtcctggt acttcacggc cacggttccc agagcggcag gatgctggct    4920
cagggccacg atgtgagcgt gggtaaagcc gtggcccacg agggcttcgt ggtgctgggc    4980
cacggtgctc cgcactttgg gcttgatctt ttcctgctgc tgctggctgt agcccagggt    5040
tctcaggtcc acctgggcgg caggagaggc atcggaaggc tgagcggccc ttcttctggg    5100
ggcgctagcg tggatgccca ctttccgctt tttcttgggt ctagaggcgt agtcaggcac    5160
gtcgtaaggg tagcccatga tatcactagc cagcttgggt ctccctatag tgagtcgtat    5220
taatttcgat aagccagtaa gcagtgggtt ctctagttag ccagagagct ctgcttatat    5280
agacctccca ccgtacacgc ctaccgccca tttgcgtcaa tggggcggag ttgttacgac    5340
attttggaaa gtcccgttga ttttggtgcc aaaacaaact cccattgacg tcaatggggt    5400
ggagacttgg aaatccccgt gagtcaaacc gctatccacg cccattgatg tactgccaaa    5460
accgcatcac catggtaata gcgatgacta atacgtagat gtactgccaa gtaggaaagt    5520
cccataaggt catgtactgg gcataatgcc aggcgggcca tttaccgtca ttgacgtcaa    5580
taggggggcgt acttggcata tgatacactt gatgtactgc caagtgggca gtttaccgta    5640
aatagtccac ccattgacgt caatggaaag tccctattgg cgttactatg ggaacatacg    5700
tcattattga cgtcaatggg cggggtcgt gggcggtca gccaggcggg ccatttaccg    5760
taagttatgt aacgcggaac tccatatatg ggctatgaac taatgacccc gtaattgatt    5820
actattaata actagtcaat aatcaatgtc aacgcgtata tctggcccgt acatcgcgaa    5880
gagtc                                                                5885
```

```
<210> SEQ ID NO 24
<211> LENGTH: 19
<212> TYPE: DNA
<213> ORGANISM: artificial sequence
<220> FEATURE:
<223> OTHER INFORMATION: TALEN T2R target sequence

<400> SEQUENCE: 24 tcagccttttt gcagtttat                                                19

<210> SEQ ID NO 25
<211> LENGTH: 5885
<212> TYPE: DNA
<213> ORGANISM: artificial sequence
<220> FEATURE:
<223> OTHER INFORMATION: TALEN T2R plasmid sequence

<400> SEQUENCE: 25
aagaacatgt gagcaaaagg ccagcaaaag cccaggaacc gtaaaaaggc cgcgttgctg      60
gcgtttttcc ataggctccg ccccctgac gagcatcaca aaatcgacg ctcaagtcag      120 aggtggcgaa acccgacagg actataaaga taccaggcgt ttccccctgg aagctccctc    180
gtgcgctctc ctgttccgac cctgccgctt accggatacc tgtccgcctt tctcccttcg    240
ggaagcgtgg cgctttctca tagctcacgc tgtaggtatc tcagttcggt gtaggtcgtt    300
cgctccaagc tgggctgtgt gcacgaaccc ccgttcagc ccgaccgctg cgccttatcc     360
ggtaactatc gtcttgagtc aacccggta agacacgact tatcgccact ggcagcagcc    420
actggtaaca ggattagcag agcgaggtat gtaggcggtg ctacagagtt cttgaagtgg    480
tggcctaact acggctacac tagaaggaca gtatttggta tctgcgctct gctgaagcca    540
gttaccttcg gaaaaagagt tggtagctct tgatccggca acaaaccac cgctggtagc    600 ggtggttttt ttgtttgcaa gcagcagatt acgcgcagaa aaaaggatc tcaagaagat    660 cctttgatct tttctacggg gtctgacgct cagtggaacg aaaactcacg ttaagggatt    720
ttggtcatga gattatcaaa aaggatcttc acctagatcc ttttaaatta aaatgaagt    780 tttagcacgt gctattattg aagcatttat cagggttatt gtctcatgag cggatacata    840
tttgaatgta tttagaaaaa taaacaaata ggggttccgc gcacatttcc ccgaaaagtg    900
ccacctgtat gcggtgtgaa ataccgcaca gatgcgtaag gagaaaatac cgcatcagga    960
aattgtaagc gttaataatt cagaagaact cgtcaagaag gcgatagaag gcgatgcgct   1020
gcgaatcggg agcggcgata ccgtaaagca cgaggaagcg gtcagcccat cgccgccaa    1080 gctcttcagc aatatcacgg gtagccaacg ctatgtcctg atagcggtcc gccacaccca   1140
gccggccaca gtcgatgaat ccagaaaagc ggccattttc caccatgata ttcggcaagc   1200
aggcatcgcc atgggtcacg acgagatcct cgccgtcggg catgctcgcc ttgagcctgg   1260
cgaacagttc ggctggcgcg agcccctgat gctcttcgtc cagatcatcc tgatcgacaa   1320
gaccggcttc catccgagta cgtgctcgct cgatgcgatg tttcgcttgg tggtcgaatg   1380
ggcaggtagc cggatcaagc gtatgcagcc gccgcattgc atcagccatg atggatactt   1440
tctcggcagg agcaaggtga gatgacagga gatcctgccc cggcacttcg cccaatagca   1500
gccagtccct tcccgcttca gtgacaacgt cgagcacagc tgcgcaagga acgcccgtcg   1560
tggccagcca cgatagccgc gctgcctcgt cttgcagttc attcagggca ccggacaggt   1620
cggtcttgac aaaaagaacc gggcgcccct gcgctgacag ccggaacacg gcggcatcag   1680
agcagccgat tgtctgttgt gcccagtcat agccgaatag cctctccacc caagcggccg   1740
```

```
gagaacctgc gtgcaatcca tcttgttcaa tcatgcgaaa cgatcctcat cctgtctctt    1800
gatcagagct tgatcccctg cgccatcaga tccttggcgg cgagaaagcc atccagttta    1860
ctttgcaggg cttcccaacc ttaccagagg gcgccccagc tggcaattcc ggttcgcttg    1920
ctgtccataa aaccgcccag tagaagccat agagcccacc gcatccccag catgcctgct    1980
attttcttcc caatcctccc ccttgctgtc ctgccccacc ccacccccca gaatagaatg    2040
acacctactc agacaatgcg atgcaatttc ctcattttat taggaaagga cagtgggagt    2100
ggcaccttcc agggtcaagg aaggcacggg ggaggggcaa acaacagatg gctggcaact    2160
agaaggcaca gtcgaggctg atcagcgggt ttaaacgggc ccttaaaagt ttatctcgcc    2220
gttattaaat ttccgtctca cttcctctaa ggttaatgtg ccggctttaa tcatttctcc    2280
accaattaaa agctcttcta cactaagaac agctccatta caattagtga tatgatttaa    2340
tcgtgtaagc tgagctttgt agtttccttt aaagtgacca ctcacaaata aaaacttaaa    2400
ttccgttaca gaagatggat agactttcca ccattcatta gggttgatat gtttgtttcg    2460
tgtttgattt tcttcgacat atcgttgcat ttcatctgct tggccaattg gcagattata    2520
acctccgcta taagctttag tatccacgat cacaccgtaa tcaataggag atccgacagt    2580
ataaattgct ccgtccggtt tccttgatcc acccaaatgt ttacctctat atccataaac    2640
tttcataaaa aattccatta ccttcatttc aagaattcta tcctgagtgg aatttctggc    2700
aatttcaatt aattcaatat attcatgagg cacatatttc aatttatgac gaagttcaga    2760
tttcttctcc tccagttcac ttttgactag ttgggatcct gtcagggcgg ccagagctgg    2820
gtcgggtctg ctcagctggg ccactataga ttccagggcg gtctgcctc cgccgttgct    2880 ggcaatggcc acgacctgct ggggtgtcag gccatgggcc tggcacagca ccggcaacag    2940
cgcctgcacc gtctccagcg cctgcttgcc gccaatattg ctggcgatgg ccaccacctg    3000
ctgcggggtc aggccatggg cctggcacag caccggcaac agccgctgca ccgtctccag    3060
cgcctgcttg cccccgccat gctggcgat ggccaccacc tgctccgggg tcaggccatg    3120
ggcctggcac agcaccggca acagccgctg caccgtctcc agagcctgct tgccaccgcc    3180
attgctggcg atggccacca cctgctccgg ggtcaggcca tggcctggc acagcaccgg    3240 caacagccgc tgcaccgtct caagcgcctg cttgccaccg ccattgctgg cgatggccac    3300
cacctgctcc ggggtcaggc catgggcctg gcacagcacc ggcaacagcc gctggacagt    3360
ctccagcgcc tgcttgccac cattattgct ggcgatggcc accacctgct ccggggtcag    3420
gccatgggcc tggcacagca ccggcaacaa tcgctgcacc gtctccagcg cctgcttgcc    3480
accaatattg ctggcgatgg ccaccacctg ctccggggtc aggccatggg cctggcacag    3540
caccggaagc agccgctgca ccgtctccag cgcctgcttg ccaccgtcgt ggctggcgat    3600
cgctaccacc tgctggggtg tcaggccatg ggcctggcac agcaccggca acagccgctg    3660
caccgtctcc agcgcctgct tgccaccatt attgctggcg atggctacca cctgttgcgg    3720
ggtcaggcca tgggcctggc acagcaccgg caacagccgc tgcaccgtct ccagcgcctg    3780
cttgccaccg tcattgctgg cgattgccac cacctgctcc ggggtcaggc catgggcctg    3840
gcacagcaac ggaaacagcc cctgcaccgt ctcaagcgcc tgcttgccac cgccattgct    3900
ggcgatggcc accacctgct ccggggtcag gccatgggcc tggcacagca ccggcaacag    3960
cgcctgcacc gtctccagcg cctgcttgcc gccgccattg ctggcgatgg ccaccacctg    4020
ctgcggggtc aggccatggg cctggcacag caccggcaac agccgctgca ccgtctccag    4080
cgcctgcttg cccccgccat gctggcgat ggccaccacc tgctccgggg tcaggccatg    4140
```

```
ggcctggcac agcaccggca acagccgctg caccgtctcc agagcctgct tgccaccgtc    4200
gtggctggcg atggccacca cctgctgcgg ggtcaggcca tgggcctggc acagcaccgg    4260
caacagccgc tgcaccgtct caagcgcctg cttgccaccg tcgtggctgg cgatggccac    4320
cacctgctcc ggggtcaggc catgggcctg gcacagcacc ggcaacagcc gctggacagt    4380
ctccagcgcc tgcttgccac cattattgct ggcgatggcc accacctgct ccggggtcag    4440
gccatgggcc tggcacagca ccggcaacaa tcgctgcacc gtctccagcg cctgcttgcc    4500
accaatattg ctggcgatgg ccaccacctg ctccggggtc aggccatggg cctggcacag    4560
caccggaagc agccgctgca ccgtctccag cgcctgcttg ccgccatcgt ggctggcgat    4620
ggccaccacc tgctgcggcg taaggttcag gggagcgcct gtcagggcat tccgccaagc    4680
gtgcacggct ccacggctg tcacgcctcc ccgcttggcg atcttcagca gctggccggt    4740
gtccagctgc agtggagggc ctctcagctc gccggccact gtcagcaagg cctcgagtgc    4800
tctagcgccg gaccactgct tgcccacgcc cacgatagcc tcgtgtgtgg cctcgggcag    4860
ggcggcgatc atgtcctggt acttcacggc acggttccc agagcggcag gatgctggct    4920
cagggccacg atgtgagcgt gggtaaagcc gtggcccacg agggcttcgt ggtgctgggc    4980
cacggtgctc cgcactttgg gcttgatctt ttcctgctgc tgctggctgt agcccagggt    5040
tctcaggtcc acctgggcgg caggagaggc atcggaaggc tgagcggccc ttcttctggg    5100
ggcgctagcg tggatgccca cttttccgctt tttcttgggt ctagaggcgt agtcaggcac    5160
gtcgtaaggg tagcccatga tatcactagc cagcttgggt ctccctatag tgagtcgtat    5220
taatttcgat aagccagtaa gcagtgggtt ctctagttag ccagagagct ctgcttatat    5280
agacctccca ccgtacacgc ctaccgccca tttgcgtcaa tggggcggag ttgttacgac    5340
attttgaaaa gtcccgttga ttttggtgcc aaaacaaact cccattgacg tcaatggggt    5400
ggagacttgg aaatccccgt gagtcaaacc gctatccacg cccattgatg tactgccaaa    5460
accgcatcac catggtaata gcgatgacta atacgtagat gtactgccaa gtaggaaagt    5520
cccataaggt catgtactgg gcataatgcc aggcgggcca tttaccgtca ttgacgtcaa    5580
tagggggcgt acttggcata tgatacactt gatgtactgc caagtgggca gtttaccgta    5640
aatagtccac ccattgacgt caatggaaag tccctattgg cgttactatg ggaacatacg    5700
tcattattga cgtcaatggg cggggtcgt tgggcggtca gccaggcggg ccatttaccg    5760
taagttatgt aacgcggaac tccatatatg gctatgaac taatgacccc gtaattgatt    5820
actattaata actagtcaat aatcaatgtc aacgcgtata tctggcccgt acatcgcgaa    5880
gagtc                                                                5885

<210> SEQ ID NO 26
<211> LENGTH: 19
<212> TYPE: DNA
<213> ORGANISM: artificial sequence
<220> FEATURE:
<223> OTHER INFORMATION: TALEN T4/5L target sequence

<400> SEQUENCE: 26
tctcattttc catacagtc                                                     19

<210> SEQ ID NO 27
<211> LENGTH: 5885
<212> TYPE: DNA
<213> ORGANISM: artificial sequence
<220> FEATURE:
<223> OTHER INFORMATION: TALEN T4/5L plasmid sequence
```

```
<400> SEQUENCE: 27
aagaacatgt gagcaaaagg ccagcaaaag cccaggaacc gtaaaaaggc cgcgttgctg    60
gcgttttcc ataggctccg cccccctgac gagcatcaca aaaatcgacg ctcaagtcag   120
aggtggcgaa acccgacagg actataaaga taccaggcgt ttccccctgg aagctccctc   180
gtgcgctctc ctgttccgac cctgccgctt accggatacc tgtccgcctt tctcccttcg   240
ggaagcgtgg cgctttctca tagctcacgc tgtaggtatc tcagttcggt gtaggtcgtt   300
cgctccaagc tgggctgtgt gcacgaaccc cccgttcagc ccgaccgctg cgccttatcc   360
ggtaactatc gtcttgagtc caacccggta agacacgact tatcgccact ggcagcagcc   420
actggtaaca ggattagcag agcgaggtat gtaggcggtg ctacagagtt cttgaagtgg   480
tggcctaact acggctacac tagaaggaca gtatttggta tctgcgctct gctgaagcca   540
gttaccttcg gaaaaagagt tggtagctct tgatccggca acaaaccac cgctggtagc    600
ggtggttttt ttgtttgcaa gcagcagatt acgcgcagaa aaaaggatc tcaagaagat   660
cctttgatct tttctacggg gtctgacgct cagtggaacg aaaactcacg ttaagggatt   720
ttggtcatga gattatcaaa aaggatcttc acctagatcc ttttaaatta aaaatgaagt   780
tttagcacgt gctattattg aagcatttat cagggttatt gtctcatgag cggatacata   840
tttgaatgta tttagaaaaa taaacaaata ggggttccgc gcacatttcc ccgaaaagtg   900
ccacctgtat gcggtgtgaa ataccgcaca gatgcgtaag gagaaaatac cgcatcagga   960
aattgtaagc gttaataatt cagaagaact cgtcaagaag gcgatagaag gcgatgcgct   1020
gcgaatcggg agcggcgata ccgtaaagca cgaggaagcg gtcagcccat tcgccgccaa   1080
gctcttcagc aatatcacgg gtagccaacg ctatgtcctg atagcggtcc gccacaccca   1140
gccggccaca gtcgatgaat ccagaaaagc ggccattttc caccatgata ttcggcaagc   1200
aggcatcgcc atgggtcacg acgagatcct cgccgtcggg catgctcgcc ttgagcctgg   1260
cgaacagttc ggctggcgcg agcccctgat gctcttcgtc cagatcatcc tgatcgacaa   1320
gaccggcttc catccgagta cgtgctcgct cgatgcgatg tttcgcttgg tggtcgaatg   1380
ggcaggtagc cggatcaagc gtatgcagcc gccgcattgc atcagccatg atggatactt   1440
tctcggcagg agcaaggtga gatgacagga gatcctgccc cggcacttcg cccaatagca   1500
gccagtccct tcccgcttca gtgacaacgt cgagcacagc tgcgcaagga acgcccgtcg   1560
tggccagcca cgatagccgc gctgcctcgt cttgcagttc attcagggca ccggacaggt   1620
cggtcttgac aaaaagaacc gggcgcccct gcgctgacag ccggaacacg gcggcatcag   1680
agcagccgat tgtctgttgt gcccagtcat agccgaatag cctctccacc caagcggccg   1740
gagaacctgc gtgcaatcca tcttgttcaa tcatgcgaaa cgatcctcat cctgtctctt   1800
gatcagagct tgatcccctg cgccatcaga tccttggcgg cgagaaagcc atccagttta   1860
ctttgcaggg cttcccaacc ttaccagagg gcgccccagc tggcaattcc ggttcgcttg   1920
ctgtccataa aaccgcccag tagaagccat agagcccacc gcatcccag catgcctgct    1980
attttcttcc caatcctccc ccttgctgtc ctgccccacc ccaccccca gaatagaatg    2040
acacctactc agacaatgcg atgcaatttc ctcatttat taggaaagga cagtgggagt    2100
ggcaccttcc agggtcaagg aaggcacggg ggaggggcaa acaacagatg gctggcaact   2160
agaaggcaca gtcgaggctg atcagcgggt ttaaacgggc ccttaaagt ttatctcgcc    2220
gttattaaat ttccgtctca cttcctctaa ggttaatgtg ccggctttaa tcatttctcc    2280
accaattaaa agctcttcta cactaagaac agctccatta caattagtga tatgatttaa   2340
```

```
tcgtgtaagc tgagctttgt agtttccttt aaagtgacca ctcacaaata aaaacttaaa    2400
ttccgttaca gaagatggat agactttcca ccattcatta gggttgatat gtttgtttcg    2460
tgtttgattt tcttcgacat atcgttgcat ttcatctgct tggccaattg gcagattata    2520
acctccgcta taagctttag tatccacgat cacaccgtaa tcaataggag atccgacagt    2580
ataaattgct ccgtccggtt tccttgatcc acccaaatgt ttacctctat atccataaac    2640
tttcataaaa aattccatta ccttcatttc aagaattcta tcctgagtgg aatttctggc    2700
aatttcaatt aattcaatat attcatgagg cacatatttc aatttatgac gaagttcaga    2760
tttcttctcc tccagttcac ttttgactag ttgggatcct gtcagggcgg ccagagctgg    2820
gtcgggtctg ctcagctggg ccacaataga ttccagggcg ggtctgcctc cgtcgtggct    2880
ggcaatggcc acgacctgct ggggtgtcag gccatgggcc tggcacagca ccggcaacag    2940
cgcctgcacc gtctccagcg cctgcttgcc gccgccattg ctggcgatgg ccaccacctg    3000
ctgcggggtc aggccatggg cctggcacag caccggcaac agccgctgca ccgtctccag    3060
cgcctgcttg cccccattat tgctggcgat ggccaccacc tgctccgggg tcaggccatg    3120
ggcctggcac agcaccggca acagccgctg caccgtctcc agagcctgct tgccaccaat    3180
attgctggcg atgccaccca cctgctccgg ggtcaggcca tgggcctggc acagcaccgg    3240
caacagccgc tgcaccgtct caagcgcctg cttgccaccg tcgtggctgg cgatggccac    3300
cacctgctcc ggggtcaggc catgggcctg gcacagcacc ggcaacagcc gctgacagt     3360 ctccagcgcc tgcttgccac caatattgct ggcgatggcc accacctgct ccggggtcag    3420
gccatgggcc tggcacagca ccggcaacaa tcgctgcacc gtctccagcg cctgcttgcc    3480
accgccattg ctggcgatgg ccaccacctg ctgcggggtc aggccatggg cctggcacag    3540
caccggaagc agccgctgca ccgtctccag cgcctgcttg ccaccaatat tgctggcgat    3600
cgctaccacc tgctggggtg tcaggccatg ggcctggcac agcaccggca acagccgctg    3660
caccgtctcc agcgcctgct tgccaccgtc gtggctggcg atggctacca cctgttgcgg    3720
ggtcaggcca tgggcctggc acagcaccgg caacagccgc tgcaccgtct ccagcgcctg    3780
cttgccaccg tcgtggctgg cgattgccac cacctgctcc ggggtcaggc catgggcctg    3840
gcacagcacc ggcaacagcg cctgcaccgt ctccagcgcc tgcttgccac cgccattgct    3900
tgcgatggcc accacctgct ccggggtcag gccatgggcc tggcacagca ccggcaacag    3960
cgcctgcacc gtctccagcg cctgcttgcc gccgccattg ctggcgatgg ccaccacctg    4020
ctgcggggtc aggccatggg cctggcacag caccggcaac agccgctgca ccgtctccag    4080
cgcctgcttg cccccgccat tgctggcgat ggccaccacc tgctccgggg tcaggccatg    4140
ggcctggcac agcaccggca acagccgctg caccgtctcc agagcctgct tgccaccgcc    4200
attgctggcg atgccaccca cctgctccgg ggtcaggcca tgggcctggc acagcaccgg    4260
caacagccgc tgcaccgtct caagcgcctg cttgccacca atattgctgg cgatggccac    4320
cacctgctcc ggggtcaggc catgggcctg gcacagcacc ggcaacagcc gctgacagt     4380 ctccagcgcc tgcttgccac cgtcgtggct ggcgatggcc accacctgct ccggggtcag    4440
gccatgggcc tggcacagca ccggcaacaa tcgctgcacc gtctccagcg cctgcttgcc    4500
accgccattg ctggcgatgg ccaccacctg ctgcggggtc aggccatggg cctggcacag    4560
caccggaagc agccgctgca ccgtctccag cgcctgcttg ccgccatcgt ggctggcgat    4620
ggccaccacc tgctgcggcg taaggttcag gggagcgcct gtcagggcat tccgccaagc    4680
gtgcacggct tccacggctg tcacgcctcc ccgcttggcg atcttcagca gctggccggt    4740
```

-continued

```
gtccagctgc agtggagggc ctctcagctc gccggccact gtcagcaagg cctcgagtgc    4800
tctagcgccg gaccactgct tgcccacgcc cacgatagcc tcgtgtgtgg cctcgggcag    4860
ggcggcgatc atgtcctggt acttcacggc cacggttccc agagcggcag gatgctggct    4920
cagggccacg atgtgagcgt gggtaaagcc gtggcccacg agggcttcgt ggtgctgggc    4980
cacggtgctc cgcactttgg gcttgatctt ttcctgctgc tgctggctgt agcccagggt    5040
tctcaggtcc acctgggcgg caggagaggc atcggaaggc tgagcggccc ttcttctggg    5100
ggcgctagcg tggatgccca ctttccgctt tttcttgggt ctagaggcgt agtcaggcac    5160
gtcgtaaggg tagcccatga tatcactagc cagcttgggc tccctatag tgagtcgtat    5220 taatttcgat aagccagtaa gcagtgggtt ctctagttag ccagagagct ctgcttatat    5280
agacctccca ccgtacacgc ctaccgccca tttgcgtcaa tggggcggag ttgttacgac    5340
attttggaaa gtcccgttga ttttggtgcc aaaacaaact cccattgacg tcaatggggt    5400
ggagacttgg aaatcccgt gagtcaaacc gctatccacg cccattgatg tactgccaaa    5460
accgcatcac catggtaata gcgatgacta atacgtagat gtactgccaa gtaggaaagt    5520
cccataaggt catgtactgg gcataatgcc aggcgggcca tttaccgtca ttgacgtcaa    5580
tagggggcgt acttggcata tgatacactt gatgtactgc caagtgggca gtttaccgta    5640
aatagtccac ccattgacgt caatggaaag tccctattgg cgttactatg gaacatacg    5700 tcattattga cgtcaatggg cggggtcgt tgggcggtca gccaggcggg ccatttaccg    5760
taagttatgt aacgcggaac tccatatatg ggctatgaac taatgacccc gtaattgatt    5820
actattaata actagtcaat aatcaatgtc aacgcgtata tctggcccgt acatcgcgaa    5880
gagtc                                                                5885
```

```
<210> SEQ ID NO 28
<211> LENGTH: 19
<212> TYPE: DNA
<213> ORGANISM: artificial sequence
<220> FEATURE:
<223> OTHER INFORMATION: TALEN T4R target sequence

<400> SEQUENCE: 28
tttaatgtct ggaaattct                                                    19

<210> SEQ ID NO 29
<211> LENGTH: 5885
<212> TYPE: DNA
<213> ORGANISM: artificial sequence
<220> FEATURE:
<223> OTHER INFORMATION: TALEN T4R plasmid sequence

<400> SEQUENCE: 29
aagaacatgt gagcaaaagg ccagcaaaag cccaggaacc gtaaaaaggc cgcgttgctg      60
gcgttttccc ataggctccg ccccctgac gagcatcaca aaaatcgacg ctcaagtcag     120
aggtggcgaa acccgacagg actataaaga taccaggcgt ttccccctgg aagctccctc     180
gtgcgctctc ctgttccgac cctgccgctt accggatacc tgtccgcctt tctcccttcg     240
ggaagcgtgg cgctttctca tagctcacgc tgtaggtatc tcagttcggt gtaggtcgtt     300
cgctccaagc tgggctgtgt gcacgaaccc cccgttcagc ccgaccgctg cgccttatcc     360
ggtaactatc gtcttgagtc caacccggta agacacgact tatcgccact ggcagcagcc     420
actggtaaca ggattagcag agcgaggtat gtaggcggtg ctacagagtt cttgaagtgg     480
tggcctaact acggctacac tagaaggaca gtatttggta tctgcgctct gctgaagcca     540
```

```
gttaccttcg gaaaaagagt tggtagctct tgatccggca acaaaccac cgctggtagc       600 ggtggttttt ttgtttgcaa gcagcagatt acgcgcagaa aaaaaggatc tcaagaagat      660
cctttgatct tttctacggg gtctgacgct cagtggaacg aaaactcacg ttaagggatt      720
ttggtcatga gattatcaaa aaggatcttc acctagatcc ttttaaatta aaaatgaagt      780
tttagcacgt gctattattg aagcatttat cagggttatt gtctcatgag cggatacata      840
tttgaatgta tttagaaaaa taaacaaata ggggttccgc gcacatttcc ccgaaaagtg      900
ccacctgtat gcggtgtgaa ataccgcaca gatgcgtaag gagaaaatac cgcatcagga      960
aattgtaagc gttaataatt cagaagaact cgtcaagaag gcgatagaag gcgatgcgct     1020
gcgaatcggg agcggcgata ccgtaaagca cgaggaagcg gtcagcccat tcgccgccaa     1080
gctcttcagc aatatcacgg gtagccaacg ctatgtcctg atagcggtcc gccacaccca     1140
gccggccaca gtcgatgaat ccagaaaagc ggccattttc caccatgata ttcggcaagc     1200
aggcatcgcc atgggtcacg acgagatcct cgccgtcggg catgctcgcc ttgagcctgg     1260
cgaacagttc ggctggcgcg agcccctgat gctcttcgtc cagatcatcc tgatcgacaa     1320
gaccggcttc catccgagta cgtgctcgct cgatgcgatg tttcgcttgg tggtcgaatg     1380
ggcaggtagc cggatcaagc gtatgcagcc gccgcattgc atcagccatg atggatactt     1440
tctcggcagg agcaaggtga gatgacagga gatcctgccc cggcacttcg cccaatagca     1500
gccagtccct tcccgcttca gtgacaacgt cgagcacagc tgcgcaagga acgcccgtcg     1560
tggccagcca cgatagccgc gctgcctcgt cttgcagttc attcagggca ccggacaggt     1620
cggtcttgac aaaaagaacc gggcgcccct gcgctgacag ccggaacacg gcggcatcag     1680
agcagccgat tgtctgttgt gcccagtcat agccgaatag cctctccacc caagcggccg     1740
gagaacctgc gtgcaatcca tcttgttcaa tcatgcgaaa cgatcctcat cctgtctctt     1800
gatcagagct tgatcccctg cgccatcaga tccttggcgg cgagaaagcc atccagttta     1860
ctttgcaggg cttcccaacc ttaccagagg gcgccccagc tggcaattcc ggttcgcttg     1920
ctgtccataa aaccgcccag tagaagccat agagcccacc gcatccccag catgcctgct     1980 atttttcttcc caatcctccc ccttgctgtc ctgcccacc ccaccccca gaatagaatg     2040 acacctactc agacaatgcg atgcaatttc ctcattttat taggaaagga cagtgggagt     2100
ggcaccttcc agggtcaagg aaggcacggg ggaggggcaa acaacagatg gctggcaact     2160
agaaggcaca gtcgaggctg atcagcgggt ttaaacgggc cttaaaagt ttatctcgcc      2220 gttattaaat ttccgtctca cttcctctaa ggttaatgtg ccggctttaa tcatttctcc     2280
accaattaaa agctcttcta cactaagaac agctccatta caattagtga tatgatttaa     2340
tcgtgtaagc tgagctttgt agtttccttt aaagtgacca ctcacaaata aaaacttaaa     2400
ttccgttaca gaagatggat agactttcca ccattcatta gggttgatat gtttgtttcg     2460
tgtttgattt tcttcgacat atcgttgcat ttcatctgct tggccaattg gcagattata     2520
acctccgcta taagctttag tatccacgat cacaccgtaa tcaataggag atccgacagt     2580
ataaattgct ccgtccggtt tccttgatcc acccaaatgt ttacctctat atccataaac     2640
tttcataaaa aattccatta ccttcatttc aagaattcta tcctgagtgg aatttctggc     2700
aatttcaatt aattcaatat attcatgagg cacatatttc aatttatgac gaagttcaga     2760
tttcttctcc tccagttcac ttttgactag ttgggatcct gtcagggcgg ccagagctgg     2820
gtcgggtctg ctcagctggg ccacaataga ttccagggcg gtctgcctc cgccgttgct      2880 ggcaatggcc acgacctgct ggggtgtcag gccatgggcc tggcacagca ccggcaacag     2940
```

```
cgcctgcacc gtctccagcg cctgcttgcc gccgtcgtgg ctggcgatgg ccaccacctg   3000
ctgcggggtc aggccatggg cctggcacag caccggcaac agccgctgca ccgtctccag   3060
cgcctgcttg cccccgccat tgctggcgat ggccaccacc tgctccgggg tcaggccatg   3120
ggcctggcac agcaccggca acagccgctg caccgtctcc agagcctgct tgccaccgcc   3180
attgctggcg atggccacca cctgctccgg ggtcaggcca tgggcctggc acagcaccgg   3240
caacagccgc tgcaccgtct caagcgcctg cttgccacca atattgctgg cgatggccac   3300
cacctgctcc ggggtcaggc catgggcctg gcacagcacc ggcaacagcc gctggacagt   3360
ctccagcgct tgcttgccac caatattgct ggcgatggcc accacctgct ccggggtcag   3420
gccatgggcc tggcacagca ccggcaacaa tcgctgcacc gtctccagcg cctgcttgcc   3480
accaatattg ctggcgatgg ccaccacctg ctccggggtc aggccatggg cctggcacag   3540
caccggaagc agccgctgca ccgtctccag cgcctgcttg ccaccattat tgctggcgat   3600
ggctaccacc tgctggggtg tcaggccatg ggcctggcac agcaccggca acagccgctg   3660
caccgtctcc agcgcctgct tgccaccatt attgctggcg atggctacca cctgttgcgg   3720
ggtcaggcca tgggcctggc acagcaccgg caacagccgc tgcaccgtct ccagcgcctg   3780
cttgccaccg ccattgctgg cgatggccac cacctgctcc ggggtcaggc catgggcctg   3840
gcacagcacc ggcaacagcg cctgcaccgt ctccagcgcc tgcttgccac cgtcgtggct   3900
tgcgatggcc accacctgct ccggggtcag gccatgggcc tggcacagca ccggcaacag   3960
cgcctgcacc gtctccagcg cctgcttgcc gccgccattg ctggcgatgg ccaccacctg   4020
ctgcggggtc aggccatggg cctggcacag caccggcaac agccgctgca ccgtctccag   4080
cgcctgcttg cccccattat tgctggcgat ggccaccacc tgctccgggg tcaggccatg   4140
ggcctggcac agcaccggca acagccgctg caccgtctcc agagcctgct tgccaccgcc   4200
attgctggcg atggccacca cctgctccgg ggtcaggcca tgggcctggc acagcaccgg   4260
caacagccgc tgcaccgtct caagcgcctg cttgccacca atattgctgg cgatggccac   4320
cacctgctcc ggggtcaggc catgggcctg gcacagcacc ggcaacagcc gctggacagt   4380
ctccagcgct tgcttgccac caatattgct ggcgatggcc accacctgct ccggggtcag   4440
gccatgggcc tggcacagca ccggcaacaa tcgctgcacc gtctccagcg cctgcttgcc   4500
accgccattg ctggcgatgg ccaccacctg ctgcggggtc aggccatggg cctggcacag   4560
caccggaagc agccgctgca ccgtctccag cgcctgcttg ccaccgccat tgctggcgat   4620
ggccaccacc tgctgcggcg taaggttcag gggagcgcct gtcagggcat tccgccaagc   4680
gtgcacggct ccacggctg tcacgcctcc ccgcttggcg atcttcagca gctggccggt   4740
gtccagctgc agtggagggc ctctcagctc gccggccact gtcagcaagg cctcgagtgc   4800
tctagcgccg gaccactgct tgcccacgcc cacgatagcc tcgtgtgtgg cctcgggcag   4860
ggcggcgatc atgtcctggt acttcacggc cacggttccc agagcggcag gatgctggct   4920
cagggccacg atgtgagcgt gggtaaagcc gtggcccacg agggcttcgt ggtgctgggc   4980
cacggtgctc cgcactttgg gcttgatctt ttcctgctgc tgctggctgt agcccagggt   5040
tctcaggtcc acctgggcgg caggagaggc atcggaaggc tgagcggccc ttcttctggg   5100
ggcgctagcg tggatgccca ctttccgctt tttcttgggt ctagaggcgt agtcaggcac   5160
gtcgtaaggg tagcccatga tatcactagc cagcttgggt ctccctatag tgagtcgtat   5220
taatttcgat aagccagtaa gcagtgggtt ctctagttag ccagagagct ctgcttatat   5280
agacctccca ccgtacacgc ctaccgccca tttgcgtcaa tggggcggag ttgttacgac   5340
```

```
atttggaaa gtcccgttga ttttggtgcc aaaacaaact cccattgacg tcaatggggt    5400
ggagacttgg aaatccccgt gagtcaaacc gctatccacg cccattgatg tactgccaaa    5460
accgcatcac catggtaata gcgatgacta atacgtagat gtactgccaa gtaggaaagt    5520
cccataaggt catgtactgg gcataatgcc aggcgggcca tttaccgtca ttgacgtcaa    5580
tagggggcgt acttggcata tgatacactt gatgtactgc caagtgggca gtttaccgta    5640
aatagtccac ccattgacgt caatggaaag tccctattgg cgttactatg gaacatacg    5700 tcattattga cgtcaatggg cggggtcgt tgggcggtca gccaggcggg ccatttaccg    5760
taagttatgt aacgcggaac tccatatatg gctatgaac taatgacccc gtaattgatt    5820
actattaata actagtcaat aatcaatgtc aacgcgtata tctggcccgt acatcgcgaa    5880
gagtc                                                                5885

<210> SEQ ID NO 30
<211> LENGTH: 19
<212> TYPE: DNA
<213> ORGANISM: artificial sequence
<220> FEATURE:
<223> OTHER INFORMATION: TALEN T5R target sequence

<400> SEQUENCE: 30
taatgtctgg aaattcttc                                                  19

<210> SEQ ID NO 31
<211> LENGTH: 5894
<212> TYPE: DNA
<213> ORGANISM: artificial sequence
<220> FEATURE:
<223> OTHER INFORMATION: TALEN T5R plasmid sequence

<400> SEQUENCE: 31
aagaacatgt gagcaaaagg ccagcaaaag cccaggaacc gtaaaaaggc cgcgttgctg    60 gcgttttttcc ataggctccg ccccctgac gagcatcaca aaaatcgacg ctcaagtcag    120
aggtggcgaa acccgacagg actataaaga taccaggcgt ttccccctgg aagctccctc    180
gtgcgctctc ctgttccgac cctgccgctt accggatacc tgtccgcctt tctcccttcg    240
ggaagcgtgg cgctttctca tagctcacgc tgtaggtatc tcagttcggt gtaggtcgtt    300
cgctccaagc tgggctgtgt gcacgaaccc ccgttcagc ccgaccgctg cgccttatcc    360
ggtaactatc gtcttgagtc aacccggta agacacgact tatcgccact ggcagcagcc    420
actggtaaca ggattagcag agcgaggtat gtaggcggtg ctacagagtt cttgaagtgg    480
tggcctaact acggctacac tagaaggaca gtatttggta tctgcgctct gctgaagcca    540
gttaccttcg gaaaaagagt tggtagctct tgatccggca acaaaccac cgctggtagc    600 ggtggttttt ttgtttgcaa gcagcagatt acgcgcagaa aaaaggatc tcaagaagat    660 cctttgatct tttctacggg gtctgacgct cagtggaacg aaaactcacg ttaagggatt    720
ttggtcatga gattatcaaa aaggatcttc acctagatcc ttttaaatta aaatgaagt    780 tttagcacgt gctattattg aagcatttat cagggttatt gtctcatgag cggatacata    840
tttgaatgta tttagaaaaa taaacaaata ggggttccgc gcacatttcc ccgaaaagtg    900
ccacctgtat gcggtgtgaa ataccgcaca gatgcgtaag gagaaaatac cgcatcagga    960
aattgtaagc gttaataatt cagaagaact cgtcaagaag gcgatagaag gcgatgcgct    1020
gcgaatcggg agcggcgata ccgtaaagca cgaggaagcg gtcagcccat tcgccgccaa    1080
gctcttcagc aatatcacgg gtagccaacg ctatgtcctg atagcggtcc gccacaccca    1140
```

-continued

| | |
|---|---|
| gccggccaca gtcgatgaat ccagaaaagc ggccattttc caccatgata ttcggcaagc | 1200 |
| aggcatcgcc atgggtcacg acgagatcct cgccgtcggg catgctcgcc ttgagcctgg | 1260 |
| cgaacagttc ggctggcgcg agcccctgat gctcttcgtc cagatcatcc tgatcgacaa | 1320 |
| gaccggcttc catccgagta cgtgctcgct cgatgcgatg tttcgcttgg tggtcgaatg | 1380 |
| ggcaggtagc cggatcaagc gtatgcagcc gccgcattgc atcagccatg atggatactt | 1440 |
| tctcggcagg agcaaggtga gatgacagga gatcctgccc cggcacttcg cccaatagca | 1500 |
| gccagtccct tcccgcttca gtgacaacgt cgagcacagc tgcgcaagga acgcccgtcg | 1560 |
| tggccagcca cgatagccgc gctgcctcgt cttgcagttc attcagggca ccggacaggt | 1620 |
| cggtcttgac aaaaagaacc gggcgcccct cgctgacag ccggaacacg gcggcatcag | 1680 |
| agcagccgat tgtctgttgt gcccagtcat agccgaatag cctctccacc caagcggccg | 1740 |
| gagaacctgc gtgcaatcca tcttgttcaa tcatgcgaaa cgatcctcat cctgtctctt | 1800 |
| gatcagagct tgatccctg cgccatcaga tccttggcgg cgagaaagcc atccagttta | 1860 |
| ctttgcaggg cttcccaacc ttaccagagg gcgcccagc tggcaattcc ggttcgcttg | 1920 |
| ctgtccataa aaccgcccag tagaagccat agagcccacc gcatcccag catgcctgct | 1980 |
| attttcttcc caatcctccc ccttgctgtc ctgcccacc ccaccccca gaatagaatg | 2040 |
| acacctactc agacaatgcg atgcaatttc ctcattttat taggaaagga cagtgggagt | 2100 |
| ggcaccttcc agggtcaagg aaggcacggg ggaggggcaa acaacagatg gctggcaact | 2160 |
| agaaggcaca gtcgaggctg atcagcgggt ttaaacgggc ccttaaaagt ttatctcgcc | 2220 |
| gttattaaat ttccgtctca cttcctctaa ggttaatgtg ccggctttaa tcatttctcc | 2280 |
| accaattaaa agctcttcta cactaagaac agctccatta caattagtga tatgatttaa | 2340 |
| tcgtgtaagc tgagctttgt agtttccttt aaagtgacca ctcacaaata aaaacttaaa | 2400 |
| ttccgttaca gaagatggat agactttcca ccattcatta gggttgatat gtttgtttcg | 2460 |
| tgtttgattt tcttcgacat atcgttgcat ttcatctgct tggccaattg gcagattata | 2520 |
| acctccgcta taagctttag tatccacgat cacaccgtaa tcaataggag atccgacagt | 2580 |
| ataaattgct ccgtccggtt tccttgatcc acccaaatgt ttacctctat atccataaac | 2640 |
| tttcataaaa aattccatta ccttcatttc aagaattcta tcctgagtgg aatttctggc | 2700 |
| aatttcaatt aattcaatat attcatgagg cacatatttc aatttatgac gaagttcaga | 2760 |
| tttcttctcc tccagttcac ttttgactag ttgggatcct gtcagggcgg ccagagctgg | 2820 |
| gtcgggtctg ctcagctggg ccacaataga ttccagggcg ggtctgcctc cgtcgtggct | 2880 |
| ggcaatggcc acgacctgct ggggtgtcag gccatgggcc tggcacagca ccggcaacag | 2940 |
| cgcctgcacc gtctccagcg cctgcttgcc gccgccattg ctggcgatgg ccaccacctg | 3000 |
| ctgcggggtc aggccatggg cctggcacag caccggcaac agccgctgca ccgtctccag | 3060 |
| cgcctgcttg cccccgccat tgctggcgat ggccaccacc tgctccgggg tcaggccatg | 3120 |
| ggcctggcac agcaccggca acagccgctg caccgtctcc aaagcctgct tgccaccgtc | 3180 |
| gtggctggcg atgccacca cctgctgcgg ggtcaggcca tgggcctggc acagcaccgg | 3240 |
| caacagccgc tgcaccgtct caagcgcctg cttgccaccg ccattgctgg cgatggccac | 3300 |
| cacctgctcc ggggtcaggc catgggcctg gcacagcacc ggcaacagcc gctggacagt | 3360 |
| ctccagcgcc tgcttgccac cgccattgct ggcgatggcc accacctgct ccggggtcag | 3420 |
| gccatgggcc tggcacagca ccggcaacaa tcgctgcacc gtctccagcg cctgcttgcc | 3480 |
| accaatattg ctggcgatgg ccaccacctg ctccggggtc aggccatggg cctggcacag | 3540 |

```
caccggaagc agccgctgca ccgtctccag cgcctgcttg ccaccaatat tgctggcgat    3600
cgctaccacc tgctggggtg tcaggccatg ggcctggcac agcaccggca acagccgctg    3660
caccgtctcc agcgcctgct tgccaccaat attgctggcg atggctacca cctgttgcgg    3720
ggtcaggcca tgggcctggc acagcaccgg caacagccgc tgcaccgtct ccagcgcctg    3780
cttgccacca ttattgctgg cgattgccac cacctgctcc ggggtcaggc catgggcctg    3840
gcacagcacc ggcaacagcg cctgcaccgt ctccagcgcc tgcttgccac cattattgct    3900
ggcgatggcc accacctgct ccggggtcag gccatgggcc tggcacagca ccggcaacag    3960
cgcctgcacc gtctccagcg cctgcttgcc gccgccattg ctggcgatgg ccaccacctg    4020
ctgcggggtc aggccatggg cctggcacag caccggcaac agccgctgca ccgtctccag    4080
cgcctgcttg ccccgtcgt ggctggcgat ggccaccacc tgctccgggg tcaggccatg    4140
ggcctggcac agcaccggca acagccgctg caccgtctcc agagcctgct tgccaccgcc    4200
attgctggcg atggccacca cctgctccgg ggtcaggcca tgggcctggc acagcaccgg    4260
caacagccgc tgcaccgtct caagcgcctg cttgccacca ttattgctgg cgatggccac    4320
cacctgctcc ggggtcaggc catgggcctg gcacagcacc ggcaacagcc gctggacagt    4380
ctccagcgcc tgcttgccac cgccattgct ggcgatggcc accacctgct ccggggtcag    4440
gccatgggcc tggcacagca ccggcaacaa tcgctgcacc gtctccagcg cctgcttgcc    4500
accaatattg ctggcgatgg ccaccacctg ctccggggtc aggccatggg cctggcacag    4560
caccggaagc agccgctgca ccgtctccag cgcctgcttg ccaccaatat tgctggcgat    4620
ggccaccacc tgctgcggcg taaggtcagg gaggttcagg ggagcgcctg tcagggcatt    4680
ccgccaagcg tgcacggctt ccacggctgt cacgcctccc gcttggcga tcttcagcag    4740
ctggccggtg tccagctgca gtggagggcc tctcagctcg ccggccactg tcagcaaggc    4800
ctcgagtgct ctagcgccgg accactgctt gcccacgccc acgatagcct cgtgtgtggc    4860
ctcgggcagg gcgcgatca tgtcctggta cttcacggcc acggttccca gagcggcagg    4920
atgctggctc agggccacga tgtgagcgtg ggtaaagccg tggcccacga gggcttcgtg    4980
gtgctgggcc acggtgctcc gcactttggg cttgatcttt cctgctgct gctggctgta    5040
gcccagggtt ctcaggtcca cctgggcggc aggagaggca tcggaaggct gagcggccct    5100
tcttctgggg gcgctagcgt ggatgcccac tttccgcttt ttcttgggtc tagaggcgta    5160
gtcaggcacg tcgtaagggt agcccatgat atcactagcc agcttgggtc tccctatagt    5220
gagtcgtatt aatttcgata agccagtaag cagtgggttc tctagttagc cagagagctc    5280
tgcttatata gacctcccac cgtacacgcc taccgcccat ttgcgtcaat ggggcggagt    5340
tgttacgaca ttttgaaaag tcccgttgat tttggtgcca aaacaaactc ccattgacgt    5400
caatggggtg gagacttgga aatccccgtg agtcaaaccg ctatccacgc ccattgatgt    5460
actgccaaaa ccgcatcacc atggtaatag cgatgactaa tacgtagatg tactgccaag    5520
taggaaagtc ccataaggtc atgtactggg cataatgcca ggcgggccat ttaccgtcat    5580
tgacgtcaat agggggcgta cttggcatat gatacacttg atgtactgcc aagtgggcag    5640
tttaccgtaa atagtccacc cattgacgtc aatggaaagt ccctattggc gttactatgg    5700
gaacatacgt cattattgac gtcaatgggc ggggtcgtt gggcggtcag ccaggcgggc    5760
catttaccgt aagttatgta acgcggaact ccatatatgg gctatgaact aatgaccccg    5820
taattgatta ctattaataa ctagtcaata atcaatgtca acgcgtatat ctggcccgta    5880
catcgcgaag agtc                                                     5894
```

```
<210> SEQ ID NO 32
<211> LENGTH: 19
<212> TYPE: DNA
<213> ORGANISM: artificial sequence
<220> FEATURE:
<223> OTHER INFORMATION: TALEN T6L target sequence

<400> SEQUENCE: 32
ttcattacac ctgcagctc                                                    19

<210> SEQ ID NO 33
<211> LENGTH: 6201
<212> TYPE: DNA
<213> ORGANISM: artificial sequence
<220> FEATURE:
<223> OTHER INFORMATION: TALEN T6L plasmid sequence

<400> SEQUENCE: 33
aagaacatgt gagcaaaagg ccagcaaaag cccaggaacc gtaaaaaggc cgcgttgctg        60
gcgttttttcc ataggctccg ccccctgac gagcatcaca aaaatcgacg ctcaagtcag      120
aggtggcgaa acccgacagg actataaaga taccaggcgt ttccccctgg aagctccctc      180
gtgcgctctc ctgttccgac cctgccgctt accggatacc tgtccgcctt tctcccttcg      240
ggaagcgtgg cgctttctca tagctcacgc tgtaggtatc tcagttcggt gtaggtcgtt      300
cgctccaagc tgggctgtgt gcacgaaccc ccgttcagc ccgaccgctg cgccttatcc       360
ggtaactatc gtcttgagtc aacccggta agacacgact tatcgccact ggcagcagcc       420
actggtaaca ggattagcag agcgaggtat gtaggcggtg ctacagagtt cttgaagtgg      480
tggcctaact acggctacac tagaaggaca gtatttggta tctgcgctct gctgaagcca      540
gttaccttcg gaaaaagagt tggtagctct tgatccggca acaaaccac cgctggtagc       600
ggtggttttt tgttgcaa gcagcagatt acgcgcagaa aaaaggatc tcaagaagat         660
cctttgatct tttctacggg gtctgacgct cagtggaacg aaaactcacg ttaagggatt      720
ttggtcatga gattatcaaa aaggatcttc acctagatcc ttttaaatta aaaatgaagt      780
tttagcacgt gctattattg aagcatttat cagggttatt gtctcatgag cggatacata      840
tttgaatgta tttagaaaaa taaacaaata ggggttccgc gcacatttcc ccgaaaagtg      900
ccacctgtat gcggtgtgaa ataccgcaca gatgcgtaag gagaaaatac cgcatcagga      960
aattgtaagc gttaataatt cagaagaact cgtcaagaag gcgatagaag gcgatgcgct     1020
gcgaatcggg agcggcgata ccgtaaagca cgaggaagcg gtcagcccat cgccgccaa      1080
gctcttcagc aatatcacgg gtagccaacg ctatgtcctg atagcggtcc gccacaccca     1140
gccggccaca gtcgatgaat ccagaaaagc ggccattttc caccatgata ttcggcaagc     1200
aggcatcgcc atgggtcacg acgagatcct cgccgtcggg catgctcgcc ttgagcctgg     1260
cgaacagttc ggctggcgcg agccctgat gctcttcgtc cagatcatcc tgatcgacaa      1320
gaccggcttc catccgagta cgtgctcgct cgatgcgatg tttcgcttgg tggtcgaatg     1380
ggcaggtagc cggatcaagc gtatgcagcc gccgcattgc atcagccatg atggatactt     1440
tctcggcagg agcaaggtga gatgacagga gatcctgccc cggcacttcg cccaatagca     1500
gccagtccct tcccgcttca gtgacaacgt cgagcacagc tgcgcaagga acgcccgtcg     1560
tggccagcca cgatagccgc gctgcctcgt cttgcagttc attcagggca ccggacaggt     1620
cggtcttgac aaaaagaacc gggcgcccct gcgctgacag ccggaacacg gcggcatcag     1680
agcagccgat tgtctgttgt gcccagtcat agccgaatag cctctccacc caagcggccg     1740
```

```
gagaacctgc gtgcaatcca tcttgttcaa tcatgcgaaa cgatcctcat cctgtctctt    1800
gatcagagct tgatccoctg cgccatcaga tccttggcgg cgagaaagcc atccagttta    1860
ctttgcaggg cttcccaacc ttaccagagg gcgccccagc tggcaattcc ggttcgcttg    1920
ctgtccataa aaccgcccag tagaagccat agagcccacc gcatcccag catgcctgct     1980 attgtcttcc caatcctccc ccttgctgtc ctgccccacc ccaccccca gaatagaatg      2040 acacctactc agacaatgcg atgcaatttc ctcattttat taggaaagga cagtgggagt    2100
ggcaccttcc agggtcaagg aaggcacggg ggaggggcaa acaacagatg ctggcaact     2160 agaaggcaca gtcgaggctg atcagcgggt ttaaacgggc cctctagact cgaggcggcc    2220
gcgctcttct tttttttttt tttttttttt tttttttttt tttttttttt tttttttttt    2280
tttttttttt tttttttttt tttttttttt tttttttttt tttttttttt tttttttttt    2340
tttttttttc tgcaggcaat gaaaataaat gttttttatt aggcagaatc cagatgctca    2400
aggcccttca taatatcccc cagtttagta gttggactta gggaacaaag gaacctttaa    2460
tagaaattgg acagcaagaa agcgagcggt accgatcgct taaaagttta tctcgccgtt    2520
attaaatttc cgtctcactt cctctaaggt taatgtgccg gctttaatca tttctccacc    2580
aattaaaagc tcttctacac taagaacagc tccattacaa ttagtgatat gatttaatcg    2640
tgtaagctga gctttgtagt ttcctttaaa gtgaccactc acaaataaaa acttaaattc    2700
cgttacagaa gatggataga cttttccacca ttcattaggg ttgatatgtt tgtttcgtgt    2760 ttgatttttct tcgacatatc gttgcatttc atctgcttgg ccaattggca gattataacc    2820
tccgctataa gctttagtat ccacgatcac accgtaatca ataggagatc cgacagtata    2880
aattgctccg tccggtttcc ttgatccacc caaatgttta cctctatatc cataaacttt    2940
cataaaaaat tccattacct tcatttcaag aattctatcc tgagtggaat ttctggcaat    3000
ttcaattaat tcaatatatt catgaggcac atatttcaat ttatgacgaa gttcagattt    3060
cttctcctcc agttcacttt tgactagttg ggatcctgtc agggcggcca gagctgggtc    3120
gggtctgctc agctgggcca caatagattc cagggcaggt cttccaccat cgtgtgaagc    3180
gatcgcaacc acttgttggg gtgtgagtcc atgatcttgg cagagcactg gcaggagtcg    3240
ttgaactgtc tcaagtgctt gcttgccccc gccatttgaa gctatagcga ctacctgttc    3300
aggggttagg ccgtggtctt gacagaggac gggaagtaac ctctggacag tttcgagggc    3360 ctgcttttcca ccatcgtgac tagcaatagc aaccacttga tctggtgtga gtccgtgcgc    3420
ctggcacaac accggcagaa gggcctggac cgtttcaagc gcttgcttgc ccccattgtt     3480
attcgctatt gctaccacct gtgctggcgt gagcccatga gcctggcaaa gaaccggaag    3540
aagccgttgg acagtctcaa gtgcctgctt gcctccgatg ttggacgcaa tcgccaccac    3600
ttggtccggt gtcaacccgt gatcttgaca aagtactggg agcaatcgtt gtacggtttc    3660
cagggcctgt ttcccaccat cgtggctggc gatagctacg acttgttgag gagtaaggcc    3720
atggtcctga cataagacag gaagtaatcg ttgcactgtc tccaaggctt gtttgccacc    3780
attgttagat gcaatcgcta caacttgctc tggggttaaa ccatgcgctt ggcatagtac    3840
gggtaacaat ctttggacag tctctagtgc ttgtttacct ccgccattag atgcgattgc    3900
cactacctga tcgggcgtca gtccatgagc ttgacatagg actggcaaca gtgcttgtac    3960
tgtttcgaga gcttgcttgc ccccatcgtg gttggcgatg gcaacgacct gggccggggt    4020
gaggccatga tcctggcata acacaggcaa gagcctctgg actgtctcaa gcgcctgttt    4080
gccgccatcg tgggaagcaa tggctacgac ctggtccgga gttagaccgt ggtcctgaca    4140
```

```
gagtaccggg agcaatcgct gaactgtttc taatgcctgt tttcctccga tgttgcttgc    4200
tatggcaact acttgctggg gggttagccc gtgagcttgg cacaaaactg aagaagtcg     4260 ctgtacggtt tcaagagcct gcttccctcc atcgtggctg gcgatggcca caacctgctc    4320
aggcgtcaag ccgtgggctt gacacaaaac aggaaggagt ctctgcacag tttccagagc    4380
ttgtttcccg ccgatgttgg aggcaattgc aaccacctga tctggcgtaa gtccgtgatc    4440
ctggcagagg accggcaata acgcctggac agtctccaaa gcctgtttac ccccgccatt    4500
gttcgctatc gctactactt gagcgggtgt taacccatgg tcttggcaca gaacgggcaa    4560
caacctttga accgtttcta gggcttgttt gcccccgcca ttactggcta tcgcgacaac    4620
ttggtcaggt gtcagaccgt gagcctgaca cagcacgggg agcaggcgtt gcacagtctc    4680
aagggcttgc ttaccgccga tgttacttgc tattgcgaca acctgttggg gggtgaggcc    4740
atgcgcctga caaagtacag gcagcaatct ctgaacagtt ccagcgcct  gcttccccc     4800 atcgtggctc gcgatcgcga cgacttgctc cggagtcaat ccatgatctt ggcagagcac    4860
tggaaggagt cgttgaactg tctcaagtgc ttgcttgccc ccgccatttg aagctatagc    4920
gactacctga tcaggcgtaa ggttcagggg agcgcctgtc agggcattcc gccaagcgtg    4980
cacggcttcc acgctgtca cgcctccccg cttggcgatc ttcagcagct ggccggtgtc     5040
cagctgcagt ggagggcctc tcagctcgcc ggccactgtc agcaaggcct cgagtgctct    5100
agcgccggac cactgcttgc ccacgcccac gatagcctcg tgtgtggcct cgggcagggc    5160
ggcgatcatg tcctggtact tcacggccac ggttcccaga gcggcaggat gctggctcag    5220
ggccacgatg tgagcgtggg taaagccgtg gcccacgagg gcttcgtggt gctgggccac    5280
ggtgctccgc actttgggct tgatcttttc ctgctgctgc tggctgtagc ccagggttct    5340
caggtccacc tgggcggcag gagaggcatc ggaaggctga gcggcccttc ttctgggggc    5400
gctagcgtgg atgcccactt tccgcttttt cttgggtcta gaggcgtagt caggcacgtc    5460
gtaagggtag cccatggtgg cgaccggtta cggaaccacg gcttgccagc ttgggtctcc    5520
ctatagtgag tcgtattaat ttcgataagc cagtaagcag tgggttctct agttagccag    5580
agagctctgc ttatatagac ctcccaccgt acacgcctac cgcccatttg cgtcaatggg    5640
gcggagttgt tacgacattt tggaaagtcc cgttgatttt ggtgccaaaa caaactccca    5700
ttgacgtcaa tggggtggag acttggaaat cccgtgagt  caaaccgcta tccacgccca    5760
ttgatgtact gccaaaaccg catcaccatg gtaatagcga tgactaatac gtagatgtac    5820
tgccaagtag gaaagtccca taaggtcatg tactgggcat aatgccaggc gggccattta    5880
ccgtcattga cgtcaatagg gggcgtactt ggcatatgat acacttgatg tactgccaag    5940
tgggcagttt accgtaaata gtccacccat tgacgtcaat ggaaagtccc tattggcgtt    6000
actatgggaa catacgtcat tattgacgtc aatgggcggg ggtcgttggg cggtcagcca    6060
ggcgggccat ttaccgtaag ttatgtaacg cggaactcca tatatgggct atgaactaat    6120
gaccccgtaa ttgattacta ttaataacta gtcaataatc aatgtcaacg cgtatatctg    6180
gcccgtacat cgcgaagagt c                                              6201
```

<210> SEQ ID NO 34
<211> LENGTH: 19
<212> TYPE: DNA
<213> ORGANISM: artificial sequence
<220> FEATURE:
<223> OTHER INFORMATION: TALEN T6R target sequence

<400> SEQUENCE: 34
ttccagaatt gatactgac					19

<210> SEQ ID NO 35
<211> LENGTH: 6205
<212> TYPE: DNA
<213> ORGANISM: artificial sequence
<220> FEATURE:
<223> OTHER INFORMATION: TALEN T6R plasmid sequence

<400> SEQUENCE: 35

| | | | | | |
|---|---|---|---|---|---|
| aagaacatgt | gagcaaaagg | ccagcaaaag | cccaggaacc | gtaaaaaggc | cgcgttgctg | 60 |
| gcgttttttcc | ataggctccg | ccccctgac | gagcatcaca | aaaatcgacg | ctcaagtcag | 120 |
| aggtggcgaa | acccgacagg | actataaaga | taccaggcgt | ttccccctgg | aagctccctc | 180 |
| gtgcgctctc | ctgttccgac | cctgccgctt | accggatacc | tgtccgcctt | tctcccttcg | 240 |
| ggaagcgtgg | cgctttctca | tagctcacgc | tgtaggtatc | tcagttcggt | gtaggtcgtt | 300 |
| cgctccaagc | tgggctgtgt | gcacgaaccc | cccgttcagc | ccgaccgctg | cgccttatcc | 360 |
| ggtaactatc | gtcttgagtc | caacccggta | agacacgact | tatcgccact | ggcagcagcc | 420 |
| actggtaaca | ggattagcag | agcgaggtat | gtaggcggtg | ctacagagtt | cttgaagtgg | 480 |
| tggcctaact | acggctacac | tagaaggaca | gtatttggta | tctgcgctct | gctgaagcca | 540 |
| gttaccttcg | gaaaaagagt | tggtagctct | tgatccggca | aacaaaccac | cgctggtagc | 600 |
| ggtggttttt | ttgtttgcaa | gcagcagatt | acgcgcagaa | aaaaggatc | tcaagaagat | 660 |
| cctttgatct | tttctacggg | gtctgacgct | cagtggaacg | aaaactcacg | ttaagggatt | 720 |
| ttggtcatga | gattatcaaa | aaggatcttc | acctagatcc | ttttaaatta | aaaatgaagt | 780 |
| tttagcacgt | gctattattg | aagcatttat | cagggttatt | gtctcatgag | cggatacata | 840 |
| tttgaatgta | tttagaaaaa | taaacaaata | ggggttccgc | gcacatttcc | ccgaaaagtg | 900 |
| ccacctgtat | gcggtgtgaa | ataccgcaca | gatgcgtaag | gagaaaatac | cgcatcagga | 960 |
| aattgtaagc | gttaataatt | cagaagaact | cgtcaagaag | gcgatagaag | gcgatgcgct | 1020 |
| gcgaatcggg | agcggcgata | ccgtaaagca | cgaggaagcg | gtcagcccat | tcgccgccaa | 1080 |
| gctcttcagc | aatatcacgg | gtagccaacg | ctatgtcctg | atagcggtcc | gccacaccca | 1140 |
| gccggccaca | gtcgatgaat | ccagaaaagc | ggccattttc | caccatgata | ttcggcaagc | 1200 |
| aggcatcgcc | atgggtcacg | acgagatcct | cgccgtcggg | catgctcgcc | ttgagcctgg | 1260 |
| cgaacagttc | ggctggcgcg | agcccctgat | gctcttcgtc | cagatcatcc | tgatcgacaa | 1320 |
| gaccggcttc | catccgagta | cgtgctcgct | cgatgcgatg | tttcgcttgg | tggtcgaatg | 1380 |
| ggcaggtagc | cggatcaagc | gtatgcagcc | gccgcattgc | atcagccatg | atggatactt | 1440 |
| tctcggcagg | agcaaggtga | gatgacagga | gatcctgccc | cggcacttcg | cccaatagca | 1500 |
| gccagtccct | tcccgcttca | gtgacaacgt | cgagcacagc | tgcgcaagga | acgcccgtcg | 1560 |
| tggccagcca | cgatagccgc | gctgcctcgt | cttgcagttc | attcagggca | ccggacaggt | 1620 |
| cggtcttgac | aaaaagaacc | gggcgcccct | gcgctgacag | ccggaacacg | gcggcatcag | 1680 |
| agcagccgat | tgtctgttgt | gcccagtcat | agccgaatag | cctctccacc | caagcggccg | 1740 |
| gagaacctgc | gtgcaatcca | tcttgttcaa | tcatgcgaaa | cgatcctcat | cctgtctctt | 1800 |
| gatcagagct | tgatccctg | cgccatcaga | tccttggcgg | cgagaaagcc | atccagttta | 1860 |
| ctttgcaggg | cttcccaacc | ttaccagagg | gcgccccagc | tggcaattcc | ggttcgcttg | 1920 |
| ctgtccataa | aaccgcccag | tagaagccat | agagcccacc | gcatccccag | catgcctgct | 1980 |

```
attgtcttcc caatcctccc ccttgctgtc ctgccccacc ccaccccca gaatagaatg    2040 acacctactc agacaatgcg atgcaatttc ctcattttat taggaaagga cagtgggagt   2100
ggcaccttcc agggtcaagg aaggcacggg ggagggggcaa acaacagatg gctggcaact  2160
agaaggcaca gtcgaggctg atcagcgggt ttaaacgggc cctctagact cgaggcggcc   2220
gcgctcttct tttttttttt tttttttttt tttttttttt tttttttttt tttttttttt   2280
tttttttttt tttttttttt tttttttttt tttttttttt tttttttttt tttttttttt   2340
tttttttttc tgcaggcaat gaaaataaat gttttttatt aggcagaatc cagatgctca   2400
aggcccttca taatatcccc cagtttagta gttggactta gggaacaaag gaacctttaa   2460
tagaaattgg acagcaagaa agcgagcggt accgatcgtc gacttaaaag tttatctcgc   2520
cgttattaaa tttccgtctc acttcctcta aggttaatgt gccggctttta atcatttctc   2580 caccaattaa aagctcttct acactaagaa cagctccatt acaattagtg atatgattta   2640
atcgtgtaag ctgagctttg tagtttcctt taaagtgacc actcacaaat aaaaacttaa   2700
attccgttac agaagatgga tagactttcc accattcatt agggttgata tgtttgtttc   2760
gtgtttgatt ttcttcgaca tatcgttgca tttcatctgc ttggccaatt ggcagattat   2820
aacctccgct ataagcttta gtatccacga tcacaccgta atcaatagga gatccgacag   2880
tataaattgc tccgtccggt ttccttgatc cacccaaatg tttacctcta tatccataaa   2940
ctttcataaa aaattccatt accttcattt caagaattct atcctgagtg gaatttctgg   3000
caatttcaat taattcaata tattcatgag gcacatattt caatttatga cgaagttcag   3060
atttcttctc ctccagttca cttttgacta gttgggatcc tgtcagggcg gccagagctg   3120
ggtcgggtct gctcagctgg gccacaatag attccagggc aggtcttcca ccatcgtgtg   3180
aagcgatcgc aaccacttgt tgggggtgtga gtccatgatc ttggcagagc actggcagga   3240
gtcgttgaac tgtctcaagt gcttgcttgc ccccgatgtt tgaagctata gcgactacct   3300
gttcaggggt taggccgtgg tcttgacaga ggacgggaag taacctctgg acagtttcga   3360
gggcctgctt tccaccattg ttactagcaa tagcaaccac ttgatctggt gtgagtccgt   3420
gcgcctggca caacaccggc agaagggcct ggaccgtttc aagcgcttgc ttgccccgc    3480 cattattcgc tattgctacc acctgtgctg gcgtgagccc atgagcctgg caaagaaccg   3540
gaagaagccg ttgacagtc tcaagtgcct gcttgcctcc atcgtgggac gcaatcgcca    3600
ccacttggtc cggtgtcaac ccgtgatctt gacaaagtac tgggagcaat cgttgtacgg   3660
tttccagggc ctgtttccca ccgatgttgc tggcgatagc tacgacttgt tgaggagtaa   3720
ggccatggtc ctgacataag acaggaagta atcgttgcac tgtctccaag gcttgtttgc   3780
caccgccatt agatgcaatc gctacaactt gctctgggt taaaccatgc gcttggcata    3840
gtacgggtaa caatctttgg acagtctcta gtgcttgttt acctccgatg ttagatgcga   3900
ttgccactac ctgatcgggc gtcagtccat gagcttgaca taggactggc aacagtgctt   3960
gtactgtttc gagagcttgc ttgccccat tgttgttggc gatggcaacg acctgggccg    4020
gggtgaggcc atgatcctgg cataacacag gcaagagcct ctggactgtc tcaagcgcct   4080
gtttgccgcc gccattggaa gcaatggcta cgacctggtc cggagttaga ccgtggtcct   4140
gacagagtac cgggagcaat cgctgaactg tttctaatgc ctgttttcct ccgccattgc   4200
ttgctatggc aactacttgc tgggggggtta gcccgtgagc ttggcacaaa actggaagaa   4260
gtcgctgtac ggtttcaaga gcctgcttcc ctccgatgtt gctggcgatg gccacaacct   4320
gctcaggcgt caagccgtgg gcttgacaca aaacaggaag gagtctctgc acagtttcca   4380
```

-continued

```
gagcttgttt cccgccgatg ttggaggcaa ttgcaaccac ctgatctggc gtaagtccgt    4440
gatcctggca gaggaccggc aataacgcct ggacagtctc caaagcctgt ttacccccat    4500
tgttgttcgc tatcgctact acttgagcgg gtgttaaccc atggtcttgg cacagaacgg    4560
gcaacaacct ttgaaccgtt tctagggctt gtttgccccc gatgttactg gctatcgcga    4620
caacttggtc aggtgtcaga ccgtgagcct gacacagcac ggggagcagg cgttgcacag    4680
tctcaagggc ttgcttaccg ccatcgtgac ttgctattgc gacaacctgt tgggggggtga   4740 ggccatgcgc ctgacaaagt acaggcagca atctctgaac agtttccagc gcctgcttcc    4800
ccccatcgtg ctcgcgatc gcgacgactt gctccggagt caatccatga tcttggcaga    4860
gcactggaag gagtcgttga actgtctcaa gtgcttgctt gccccgcca tttgaagcta    4920 tagcgactac ctgatcaggc gtaaggttca ggggagcgcc tgtcagggca ttccgccaag    4980
cgtgcacggc ttccacggct gtcacgcctc cccgcttggc gatcttcagc agctggccgg    5040
tgtccagctg cagtggaggg cctctcagct cgccggccac tgtcagcaag gcctcgagtg    5100
ctctagcgcc ggaccactgc ttgcccacgc ccacgatagc ctcgtgtgtg gcctcgggca    5160
gggcggcgat catgtcctgg tacttcacgg ccacggttcc cagagcggca ggatgctggc    5220
tcagggccac gatgtgagcg tgggtaaagc cgtggcccac gagggcttcg tggtgctggg    5280
ccacggtgct ccgcactttg ggcttgatct tttcctgctg ctgctggctg tagcccaggg    5340
ttctcaggtc cacctgggcg gcaggagagg catcggaagg ctgagcggcc cttcttctgg    5400
gggcgctagc gtggatgccc actttccgct ttttcttggg tctagaggcg tagtcaggca    5460
cgtcgtaagg gtagcccatg gtggcgaccg gttacgaaac cacggcttgc cagcttgggt    5520
ctccctatag tgagtcgtat aatttcgat aagccagtaa gcagtgggtt ctctagttag    5580
ccagagagct ctgcttatat agacctccca ccgtacacgc ctaccgccca tttgcgtcaa    5640
tggggcggag ttgttacgac attttggaaa gtcccgttga ttttggtgcc aaaacaaact    5700
cccattgacg tcaatggggt ggagacttgg aaatccccgt gagtcaaacc gctatccacg    5760
cccattgatg tactgccaaa accgcatcac catggtaata gcgatgacta atacgtagat    5820
gtactgccaa gtaggaaagt cccataaggt catgtactgg cataatgcc aggcgggcca    5880 tttaccgtca ttgacgtcaa tagggggcgt acttggcata tgatacactt gatgtactgc    5940
caagtgggca gtttaccgta aatagtccac ccattgacgt caatggaaag tccctattgg    6000
cgttactatg ggaacatacg tcattattga cgtcaatggg cggggtcgt tgggcggtca    6060 gccaggcggg ccatttaccg taagttatgt aacgcggaac tccatatatg gctatgaac    6120 taatgacccc gtaattgatt actattaata actagtcaat aatcaatgtc aacgcgtata    6180
tctggcccgt acatcgcgaa gagtc                                          6205
```

<210> SEQ ID NO 36
<211> LENGTH: 12
<212> TYPE: DNA
<213> ORGANISM: artificial sequence
<220> FEATURE:
<223> OTHER INFORMATION: ZFN L target sequence

<400> SEQUENCE: 36

```
gtcatcctca tc                                                           12
```

<210> SEQ ID NO 37
<211> LENGTH: 6280
<212> TYPE: DNA
<213> ORGANISM: artificial sequence
<220> FEATURE:
<223> OTHER INFORMATION: ZFN L plasmid sequence

<400> SEQUENCE: 37

| | | | | | |
|---|---|---|---|---|---|
| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacgggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | gcactttcca | aaatgtcgta | acaactccgc | cccattgacg | caaatgggcg | 780 |
| gtagccgtgt | acggtgggag | gtctatataa | gcagagctcg | tttagtgaac | cgtcagatcg | 840 |
| cctggagacg | ccatccacgc | tgttttgacc | tccatagaag | acaccgggac | cgatccagcc | 900 |
| tccgcggccg | gaacggtgc | attggaacgc | ggattcccg | tgccaagagt | gacgtaagta | 960 |
| ccgcctatag | agtctatggc | ccaccccctt | ggcttcgtta | aacgcggct | acaattaata | 1020 |
| cataaccta | tgtatcatac | acatacgatt | taggtgacac | tatagaataa | catccacttt | 1080 |
| gcctttctct | ccacaggtgt | ctaggatggg | ctacccttac | gacgtgcctg | actacgcctc | 1140 |
| tagacccaag | aaaaagcgga | agtgggcat | ccacgctagc | cctgccgcca | tggctgagag | 1200 |
| gcccttccag | tgccggatct | gcatgcggaa | cttcagcgac | cggtccaacc | tgagccggca | 1260 |
| catccggacc | cacaccggcg | agaagcccctt | cgcctgcgac | atctgcggcc | ggaagttcgc | 1320 |
| catcagcagc | aacctgaaca | gccacaccaa | gatccacacc | ggcagccaga | aacctttcca | 1380 |
| gtgcagaatc | tgtatgagaa | acttcagccg | cagcgacaac | ctggcaagac | acatcagaac | 1440 |
| acacacgggc | gagaaaccgt | ttgcatgtga | tatctgtggg | cgaaagttcg | ccacctccgg | 1500 |
| caatctgacc | cggcacacaa | agatccacct | gagggggatcc | caactagtca | agagcgagct | 1560 |
| ggaagaaaag | aagagcgaac | tgcgccacaa | gctgaaatac | gtgcctcacg | agtacatcga | 1620 |
| actgatcgaa | atcgcccgca | acagcaccca | ggaccgcatc | ctggaaatga | agtgatggaa | 1680 |
| attcttcatg | aaggtgtacg | gctaccgcgg | caagcacctg | ggcggcagcc | gcaagcctga | 1740 |
| cggcgccatc | tacaccgtgg | gcagcccctat | cgactacggc | gtgatcgtgg | acaccaaggc | 1800 |
| ctacagcggc | ggctacaacc | tgcctatcgg | ccaggccgac | gaaatggaac | gctacgtgga | 1860 |
| agaaaaccag | acccgcaaca | agcacgccaa | ccctaacgaa | tggtggaagg | tgtaccctag | 1920 |
| cagcgtgacc | gaattcaagt | tcctgttcgt | gagcggccac | ttcaagggca | actacaaggc | 1980 |
| ccagctgacc | cgcctgaacc | acatcaccaa | ctgcaacggc | gccgtgctgt | ccgtggaaga | 2040 |
| actgctgatc | ggcggcgaaa | tgattaaggc | cgggaccctg | acctggaag | aagtgcgccg | 2100 |
| caagttcaac | aacggcgaaa | tcaacttta | agggcccttc | gaaggtaagc | ctatccctaa | 2160 |
| ccctctcctc | ggtctcgatt | ctacgcgtac | cggtcatcat | caccatcacc | attgagttta | 2220 |

```
aacccgctga tcagcctcga ctgtgccttc tagttgccag ccatctgttg tttgcccctc    2280
ccccgtgcct tccttgaccc tggaaggtgc cactcccact gtcctttcct aataaaatga    2340
ggaaattgca tcgcattgtc tgagtaggtg tcattctatt ctgggggtg gggtggggca     2400 ggacagcaag ggggaggatt gggaagacaa tagcaggcat gctggggatg cggtgggctc    2460
tatggcttct gaggcggaaa gaaccagctg gggctctagg gggtatcccc acgcgccctg    2520
tagcggcgca ttaagcgcgg cgggtgtggt ggttacgcgc agcgtgaccg ctacacttgc    2580
cagcgcccta gcgcccgctc ctttcgcttt cttcccttcc tttctcgcca cgttcgccgg    2640
ctttccccgt caagctctaa atcggggcat ccctttaggg ttccgattta gtgctttacg    2700
gcacctcgac cccaaaaaac ttgattaggg tgatggttca cgtagtgggc catcgccctg    2760
atagacggtt tttcgccctt tgacgttgga gtccacgttc tttaatagtg gactcttgtt    2820
ccaaactgga acaacactca accctatctc ggtctattct tttgatttat aagggatttt    2880
ggggatttcg gcctattggt taaaaaatga gctgatttaa caaaaattta acgcgaatta    2940
attctgtgga atgtgtgtca gttagggtgt ggaaagtccc caggctcccc aggcaggcag    3000
aagtatgcaa agcatgcatc tcaattagtc agcaaccagg tgtggaaagt ccccaggctc    3060
cccagcaggc agaagtatgc aaagcatgca tctcaattag tcagcaacca tagtcccgcc    3120
cctaactccg cccatcccgc cctaactccg cccagttccg cccattctc cgccccatgg    3180 ctgactaatt ttttttattt atgcagaggc cgaggccgcc tctgcctctg agctattcca    3240
gaagtagtga ggaggctttt ttggaggcct aggcttttgc aaaaagctcc cgggagcttg    3300
tatatccatt ttcggatctg atcagcacgt gttgacaatt aatcatcggc atagtatatc    3360
ggcatagtat aatacgacaa ggtgaggaac taaaccatgg ccaagccttt gtctcaagaa    3420
gaatccaccc tcattgaaag agcaacggct acaatcaaca gcatccccat ctctgaagac    3480
tacagcgtcg ccagcgcagc tctctctagc gacggccgca tcttcactgg tgtcaatgta    3540
tatcatttta ctgggggacc ttgtgcagaa ctcgtggtgc tgggcactgc tgctgctgcg    3600
gcagctggca acctgacttg tatcgtcgcg atcggaaatg agaacagggg catcttgagc    3660
ccctgcggac ggtgtcgaca ggtgcttctc gatctgcatc ctgggatcaa agcgatagtg    3720
aaggacagtg atggacagcc gacggcagtt gggattcgtg aattgctgcc ctctggttat    3780
gtgtgggagg gctaagcact tcgtggccga ggagcaggac tgacacgtgc tacgagattt    3840
cgattccacc gccgccttct atgaaaggtt gggcttcgga atcgttttcc gggacgccgg    3900
ctggatgatc ctccagcgcg gggatctcat gctggagttc ttcgcccacc ccaacttgtt    3960
tattgcagct tataatggtt acaaataaag caatagcatc acaaatttca caaataaagc    4020
atttttttca ctgcattcta gttgtggttt gtccaaactc atcaatgtat cttatcatgt    4080
ctgtataccg tcgacctcta gctagagctt ggcgtaatca tggtcatagc tgtttcctgt    4140
gtgaaattgt tatccgctca caattccaca acatacga gccggaagca taaagtgtaa    4200
agcctggggt gcctaatgag tgagctaact cacattaatt gcgttgcgct cactgcccgc    4260
tttccagtcg ggaaacctgt cgtgccagct gcattaatga atcggccaac gcgcggggag    4320
aggcggtttg cgtattgggc gctcttccgc ttcctcgctc actgactcgc tgcgctcggt    4380
cgttcggctg cggcgagcgg tatcagctca ctcaaaggcg gtaatacggt tatccacaga    4440
atcaggggat aacgcaggaa agaacatgtg agcaaaaggc cagcaaaagg ccaggaaccg    4500
taaaaaggcc gcgttgctgg cgttttccca taggctccgc ccccctgacg agcatcacaa    4560
aaatcgacgc tcaagtcaga ggtggcgaaa cccgacagga ctataaagat accaggcgtt    4620
```

```
tccccctgga agctccctcg tgcgctctcc tgttccgacc ctgccgctta ccggatacct    4680
gtccgccttt ctcccttcgg gaagcgtggc gctttctcaa tgctcacgct gtaggtatct    4740
cagttcggtg taggtcgttc gctccaagct gggctgtgtg cacgaacccc ccgttcagcc    4800
cgaccgctgc gccttatccg gtaactatcg tcttgagtcc aacccggtaa gacacgactt    4860
atcgccactg gcagcagcca ctggtaacag gattagcaga gcgaggtatg taggcggtgc    4920
tacagagttc ttgaagtggt ggcctaacta cggctacact agaaggacag tatttggtat    4980
ctgcgctctg ctgaagccag ttaccttcgg aaaagagtt ggtagctctt gatccggcaa     5040
acaaaccacc gctggtagcg gtggtttttt tgtttgcaag cagcagatta cgcgcagaaa    5100
aaaaggatct caagaagatc ctttgatctt ttctacgggg tctgacgctc agtggaacga    5160
aaactcacgt taagggattt tggtcatgag attatcaaaa aggatcttca cctagatcct    5220
tttaaattaa aaatgaagtt ttaaatcaat ctaaagtata tatgagtaaa cttggtctga    5280
cagttaccaa tgcttaatca gtgaggcacc tatctcagcg atctgtctat ttcgttcatc    5340
catagttgcc tgactccccg tcgtgtagat aactacgata cgggagggct taccatctgg    5400
ccccagtgct gcaatgatac cgcgagaccc acgctcaccg gctccagatt tatcagcaat    5460
aaaccagcca gccggaaggg ccgagcgcag aagtggtcct gcaactttat ccgcctccat    5520
ccagtctatt aattgttgcc gggaagctag agtaagtagt tcgccagtta atagtttgcg    5580
caacgttgtt gccattgcta caggcatcgt ggtgtcacgc tcgtcgtttg gtatggcttc    5640
attcagctcc ggttcccaac gatcaaggcg agttacatga tcccccatgt tgtgcaaaaa    5700
agcggttagc tccttcggtc ctccgatcgt tgtcagaagt aagttggccg cagtgttatc    5760
actcatggtt atggcagcac tgcataattc tcttactgtc atgccatccg taagatgctt    5820
ttctgtgact ggtgagtact caaccaagtc attctgagaa tagtgtatgc ggcgaccgag    5880
ttgctcttgc ccggcgtcaa tacgggataa taccgcgcca catagcagaa ctttaaaagt    5940
gctcatcatt ggaaaacgtt cttcggggcg aaaactctca aggatcttac cgctgttgag    6000
atccagttcg atgtaaccca ctcgtgcacc caactgatct tcagcatctt ttactttcac    6060
cagcgtttct gggtgagcaa aaacaggaag gcaaaatgcc gcaaaaaagg gaataagggc    6120
gacacggaaa tgttgaatac tcatactctt ccttttcaa tattattgaa gcatttatca     6180
gggttattgt ctcatgagcg gatacatatt tgaatgtatt tagaaaaata aacaaatagg    6240
ggttccgcgc acatttcccc gaaaagtgcc acctgacgtc                          6280
```

<210> SEQ ID NO 38
<211> LENGTH: 12
<212> TYPE: DNA
<213> ORGANISM: artificial sequence
<220> FEATURE:
<223> OTHER INFORMATION: ZFN R target sequence

<400> SEQUENCE: 38
cttttgcagt tt                                                            12

<210> SEQ ID NO 39
<211> LENGTH: 6277
<212> TYPE: DNA
<213> ORGANISM: artificial sequence
<220> FEATURE:
<223> OTHER INFORMATION: ZFN R plasmid sequence

```
<400> SEQUENCE: 39
gacgtcaggt ggcacttttc ggggaaatgt gcgcggaacc cctatttgtt tattttcta         60
aatacattca aatatgtatc cgctcatgag acaataaccc tgataaatgc ttcaataata        120
ttgaaaaagg aagagtatga gtattcaaca tttccgtgtc gcccttattc ccttttttgc        180
ggcattttgc cttcctgttt ttgctcaccc agaaacgctg gtgaaagtaa agatgctga         240
agatcagttg ggtgcacgag tgggttacat cgaactggat ctcaacagcg gtaagatcct       300
tgagagtttt cgccccgaag aacgttttcc aatgatgagc acttttaaag ttctgctatg       360
tggcgcggta ttatcccgta ttgacgccgg gcaagagcaa ctcggtcgcc gcatacacta       420
ttctcagaat gacttggttg agtactcacc agtcacagaa aagcatctta cggatggcat       480
gacagtaaga gaattatgca gtgctgccat aaccatgagt gataacactg cggccaactt       540
acttctgaca acgatcggag gaccgaagga gctaaccgct tttttgcaca acatggggga      600
tcatgtaact cgccttgatc gttgggaacc ggagctgaat gaagccatac caaacgacga      660
gcgtgacacc acgatgcctg tagcaatggc aacaacgttg cgcaaactat taactggcga      720
actacttact ctagcttccc ggcaacaatt aatagactgg atggaggcgg ataaagttgc      780
aggaccactt ctgcgctcgg cccttccggc tggctggttt attgctgata atctggagc       840
cggtgagcgt gggtctcgcg gtatcattgc agcactgggg ccagatggta agccctcccg      900
tatcgtagtt atctacacga cggggagtca ggcaactatg gatgaacgaa atagacagat      960
cgctgagata ggtgcctcac tgattaagca ttggtaactg tcagaccaag tttactcata     1020
tatactttag attgatttaa aacttcattt ttaatttaaa aggatctagg tgaagatcct     1080
ttttgataat ctcatgacca aaatccctta acgtgagttt tcgttccact gagcgtcaga     1140
ccccgtagaa aagatcaaag gatcttcttg agatcctttt tttctgcgcg taatctgctg     1200
cttgcaaaca aaaaaaccac cgctaccagc ggtggtttgt ttgccggatc aagagctacc     1260
aactcttttt ccgaaggtaa ctggcttcag cagagcgcag ataccaaata ctgtccttct     1320
agtgtagccg tagttaggcc accacttcaa gaactctgta gcaccgccta catacctcgc     1380
tctgctaatc ctgttaccag tggctgctgc cagtggcgat aagtcgtgtc ttaccgggtt     1440
ggactcaaga cgatagttac cggataaggc gcagcggtcg ggctgaacgg ggggttcgtg     1500
cacacagccc agcttggagc gaacgaccta caccgaactg agatacctac agcgtgagca     1560
ttgagaaagc gccacgcttc ccgaagggag aaaggcggac aggtatccgg taagcggcag     1620
ggtcggaaca ggagagcgca cgagggagct tccaggggga aacgcctggt atctttatag     1680
tcctgtcggg tttcgccacc tctgacttga gcgtcgattt ttgtgatgct cgtcaggggg     1740
gcggagccta tggaaaaacg ccagcaacgc ggcctttta cggttcctgg ccttttgctg      1800
gccttttgct cacatgttct ttcctgcgtt atcccctgat tctgtggata accgtattac     1860
cgcctttgag tgagctgata ccgctcgccg cagccgaacg accgagcgca gcgagtcagt    1920
gagcgaggaa gcggaagagc gcccaatacg caaaccgcct ctccccgcgc gttggccgat    1980
tcattaatgc agctggcacg acaggtttcc cgactggaaa gcgggcagtg agcgcaacgc    2040
aattaatgtg agttagctca ctcattaggc accccaggct ttacacttta tgcttccggc    2100
tcgtatgttg tgtggaattg tgagcggata acaatttcac acaggaaaca gctatgacca    2160
tgattacgcc aagctctagc tagaggtcga cggtatacag acatgataag atacattgat    2220
gagtttggac aaaccacaac tagaatgcag tgaaaaaaat gctttatttg tgaaatttgt    2280
gatgctattg ctttatttgt aaccattata agctgcaata aacaagttgg ggtgggcgaa    2340
```

```
gaactccagc atgagatccc cgcgctggag gatcatccag ccggcgtccc ggaaaacgat    2400
tccgaagccc aacctttcat agaaggcggc ggtggaatcg aaatctcgta gcacgtgtca    2460
gtcctgctcc tcggccacga agtgcttagc cctcccacac ataaccagag ggcagcaatt    2520
cacgaatccc aactgccgtc ggctgtccat cactgtcctt cactatcgct ttgatcccag    2580
gatgcagatc gagaagcacc tgtcgacacc gtccgcaggg gctcaagatg cccctgttct    2640
catttccgat cgcgacgata caagtcaggt tgccagctgc cgcagcagca gcagtgccca    2700
gcaccacgag ttctgcacaa ggtcccccag taaaatgata tacattgaca ccagtgaaga    2760
tgcggccgtc gctagagaga gctgcgctgg cgacgctgta gtcttcagag atggggatgc    2820
tgttgattgt agccgttgct ctttcaatga gggtggattc ttcttgagac aaaggcttgg    2880
ccatggttta gttcctcacc ttgtcgtatt atactatgcc gatatactat gccgatgatt    2940
aattgtcaac acgtgctgat cagatccgaa aatggatata caagctcccg ggagcttttt    3000
gcaaaagcct aggcctccaa aaagcctcc tcactacttc tggaatagct cagaggcaga    3060
ggcggcctcg gcctctgcat aaataaaaaa aattagtcag ccatggggcg gagaatgggc    3120
ggaactgggc ggagttaggg gcgggatggg cggagttagg ggcgggacta tggttgctga    3180
ctaattgaga tgcatgcttt gcatacttct gcctgctggg gagcctgggg actttccaca    3240
cctggttgct gactaattga gatgcatgct ttgcatactt ctgcctgcct ggggagcctg    3300 gggacttttcc acaccctaac tgacacacat tccacagaat taattcgcgt taaattttttg    3360 ttaaatcagc tcatttttta accaataggc cgaaatcccc aaaatccctt ataaatcaaa    3420
agaatagacc gagatagggt tgagtgttgt tccagtttgg aacaagagtc cactattaaa    3480
gaacgtggac tccaacgtca aagggcgaaa aaccgtctat cagggcgatg ccccactacg    3540
tgaaccatca ccctaatcaa gttttttggg gtcgaggtgc cgtaaagcac taaatcggaa    3600
ccctaaaggg atgccccgat ttagagcttg acggggaaag ccggcgaacg tggcgagaaa    3660
ggaagggaag aaagcgaaag gagcgggcgc tagggcgctg gcaagtgtag cggtcacgct    3720
gcgcgtaacc accacacccg ccgcgcttaa tgcgccgcta cagggcgcgt ggggataccc    3780
cctagagccc cagctggttc tttccgcctc agaagccata gagcccaccg catccccagc    3840
atgcctgcta ttgtcttccc aatcctcccc cttgctgtcc tgccccaccc cacccccag    3900 aatagaatga cacctactca gacaatgcga tgcaatttcc tcattttatt aggaaaggac    3960
agtgggagtg gcaccttcca gggtcaagga aggcacgggg gaggggcaaa caacagatgg    4020
ctggcaacta gaaggcacag tcgaggctga tcagcgggtt taaactcaat ggtgatggtg    4080
atgatgaccg gtacgcgtag aatcgagacc gaggagaggg ttagggatag gcttaccttc    4140
gaagggccct taaagttga tttcgccgtt gttgaacttg cggcgcactt cttccagggt    4200
cagggtgccg gccttaatca tttcgccgcc gatcagcagt tcttccacgg acagcacggc    4260
gccgttgcag ttggtcacgt ggttcaggcg ggtcagctgg gccttgtagt tgcccttgaa    4320
gtggccgctc acgaacagga acttgaattc ggtcacgctg ctagggtaca ccttccacca    4380
ttcgttaggg ttgatgtgct tgttgcgggt ctggtttttct ttcacgtagc gctgcatttc    4440
gtcggcctgg ccgataggca ggttgtagcc gccgctgtag gccttggtgt ccacgatcac    4500
gccgtagtcg atagggctgc ccacggtgta gatggcgccg tcaggcttgc ggctgccgcc    4560
caggtgcttg ccgcggtagc cgtacacctt catgaagaat tccatcactt tcatttccag    4620
gatgcggtcc tgggtgctgt tgcgggcgat ttcgatcagt tcgatgtact cgtgaggcac    4680
gtatttcagc ttgtggcgca gttcgctctt cttttcttcc agctcgctct tgactagttg    4740
```

```
ggatcccctc aggtggatct tgtgtgggt ggtccggtgg ttccgctggg caaactttct    4800
cccacatata tcgcaggcaa acggtttctc ccctgtgtgt gttctgatgt gctcggacag    4860
cacgtcgctg cggctgaagt ttctcataca tattctgcat tggaaaggct tttcgcctgt    4920
gtggatcttg gtgtgcacct ggaggttgat tttctgggcg aacttccggc cgcagatgtc    4980
gcaggcgaag ggcttctcgc cggtgtgggt ccggatgtgc acgctcaggt tgtcggatct    5040
gctgaagttc cgcatgcaga tccggcactg gaagggcctc tcagccatgg cggcagggct    5100
agcgtggatg cccactttcc gcttttttctt gggtctagag gcgtagtcag gcacgtcgta    5160
agggtagccc atcctagaca cctgtggaga gaaaggcaaa gtggatgtta ttctatagtg    5220
tcacctaaat cgtatgtgta tgatacataa ggttatgtat taattgtagc cgcgttctaa    5280
cgaagccaag ggggtgggcc atagactcta taggcggtac ttacgtcact cttggcacgg    5340
ggaatccgcg ttccaatgca ccgttcccgg ccgcggaggc tggatcggtc ccggtgtctt    5400
ctatggaggt caaaacagcg tggatggcgt ctccaggcga tctgacggtt cactaaacga    5460
gctctgctta tatagacctc ccaccgtaca cggctaccgc ccatttgcgt caatggggcg    5520
gagttgttac gacattttgg aaagtgccgt tgattttggt gccaaaacaa actcccattg    5580
acgtcaatgg ggtggagact tggaaatccc cgtgagtcaa accgctatcc acgcccattg    5640
atgtactgcc aaaaccgcat caccatggta atagcgatga ctaatacgta gatgtactgc    5700
caagtaggaa agtcccataa ggtcatgtac tgggcataat gccaggcggg ccatttaccg    5760
tcattgacgt caatagggg cgtacttggc atatgataca cttgatgtac tgccaagtgg    5820
gcagtttacc gtaaatagtc cacccattga cgtcaatgga aagtccctat tggcgttact    5880
atgggaacat acgtcattat tgacgtcaat gggcggggt cgttgggcgg tcagccaggc    5940
gggccattta ccgtaagtta tgtaacgcgg aactccatat atgggctatg aactaatgac    6000
cccgtaattg attactatta ataactagtc aataatcaat gtcaacgcgt atatctggcc    6060
cgtacatcgc gaagcagcgc aaaacgccta accctaagca gattcttcat gcaattgtcg    6120
gtcaagcctt gccttgttgt agcttaaatt ttgctcgcgc actactcagc gacctccaac    6180
acacaagcag ggagcagata ctggcttaac tatgcggcat cagagcagat tgtactgaga    6240
gtcgaccata ggggatcggg agatctcccg atccgtc                              6277
```

<210> SEQ ID NO 40
<211> LENGTH: 20
<212> TYPE: DNA
<213> ORGANISM: artificial sequence
<220> FEATURE:
<223> OTHER INFORMATION: gRNA#3

<400> SEQUENCE: 40
cctgcctccg ctctactcac                                                   20

<210> SEQ ID NO 41
<211> LENGTH: 32
<212> TYPE: DNA
<213> ORGANISM: artificial sequence
<220> FEATURE:
<223> OTHER INFORMATION: Delta32

<400> SEQUENCE: 41
gtcagtatca attctggaag aatttccaga ca                                     32

-continued

```
<210> SEQ ID NO 42
<211> LENGTH: 11
<212> TYPE: DNA
<213> ORGANISM: artificial sequence
<220> FEATURE:
<223> OTHER INFORMATION: MegaTAL-T target sequence

<400> SEQUENCE: 42
gtccttctcc t                                                         11

<210> SEQ ID NO 43
<211> LENGTH: 22
<212> TYPE: DNA
<213> ORGANISM: artificial sequence
<220> FEATURE:
<223> OTHER INFORMATION: MegaTAL- M cleavage sequence

<400> SEQUENCE: 43
cttccaggaa ttctttggcc tg                                             22

<210> SEQ ID NO 44
<211> LENGTH: 3378
<212> TYPE: DNA
<213> ORGANISM: artificial sequence
<220> FEATURE:
<223> OTHER INFORMATION: MegaTAL polynucleotide sequence

<400> SEQUENCE: 44
atgggatcct gcaggtatcc atatgatgtc ccagattatg cgccacctaa gaagaaacgc     60
aaagtcgtgg atctacgcac gctcggctac agtcagcagc agcaagagaa gatcaaaccg    120
aaggtgcgtt cgacagtggc gcagcaccac gaggcactgg tgggccatgg gtttacacac    180
gcgcacatcg ttgcgctcag ccaacacccg gcagcgttag gaccgtcgc tgtcacgtat     240 cagcacataa tcacggcgtt gccagaggcg acacacgaag acatcgttgg cgtcggcaaa    300
cagtggtccg gcgcacgcgc cctggaggcc ttgctcacgg atgcggggga gttgagaggt    360
ccgccgttac agttggacac aggccaactt gtgaagattg caaaacgtgg cggcgtgacc    420
gcaatggagg cagtgcatgc atcgcgcaat gcactgacgg gtgcccccct gaacctgacc    480
ccggaccaag tggtggctat cgccagcaac aatggcggca agcaagcgct cgaaacggtg    540
cagcggctgt tgccggtgct gtgccaggac catggcctga ccccggacca agtggtggct    600
atcgccagca acggtggcgg caagcaagcg ctcgaaacgg tgcagcggct gttgccggtg    660
ctgtgccagg accatggcct gactccggac caagtggtgg ctatcgccag ccacgatggc    720
ggcaagcaag cgctcgaaac ggtgcagcgg ctgttgccgg tgctgtgcca ggaccatggc    780
ctgactccgg accaagtggt ggctatcgcc agccacgatg cggcaagca agcgctcgaa    840 acggtgcagc ggctgttgcc ggtgctgtgc caggaccatg gcctgacccc ggaccaagtg    900
gtggctatcg ccagcaacgg tggcggcaag caagcgctcg aaacggtgca gcggctgttg    960
ccggtgctgt gccaggacca tggcctgacc ccggaccaag tggtggctat cgccagcaac   1020
ggtggcggca agcaagcgct cgaaacggtg cagcggctgt tgccggtgct gtgccaggac   1080
catggcctga ctccggacca agtggtggct atcgccagcc acgatggcgg caagcaagcg   1140
ctcgaaacgg tgcagcggct gttgccggtg ctgtgccagg accatggcct gaccccggac   1200
caagtggtgg ctatcgccag caacggtggc ggcaagcaag cgctcgaaac ggtgcagcgg   1260
ctgttgccgg tgctgtgcca ggaccatggc ctgactccgg accaagtggt ggctatcgcc   1320
agccacgatg cggcaagca agcgctcgaa acggtgcagc ggctgttgcc ggtgctgtgc    1380
```

```
caggaccatg gcctgactcc ggaccaagtg gtggctatcg ccagccacga tggcggcaag      1440
caagcgctcg aaacggtgca gcggctgttg ccggtgctgt gccaggacca tggcctgacc      1500
ccggaccaag tggtggctat cgccagcaac ggtggcggca agcaagcgct cgaaagcatt      1560
gtggcccagc tgagccggcc tgatccggcg ttggccgcgt tgaccaacga ccacctcgtc      1620
gccttggcct gcctcggcgg acgtcctgcc atggatgcag tgaaaaaggg attgccgcac      1680
gcgccggaat tgatcagaag agtcaatcgc cgtattggcg aacgcacgtc ccatcgcgtt      1740
gcgatatcta gagtgggagg aagctcgcgc agagagtcca tcaacccatg gattctgact      1800
ggtttcgctg atgccgaagc atccttcatg ctaagaatcc gtagcgcgaa caaccggtca      1860
gtagggtact acactgacct ggtattcgaa atcactctgc acaacaagga caaatcgatt      1920
ctggagaata tccagtcgac ttggaaggtc ggcacaatca caaccgaggc gacggcacc      1980 gtcagactga gcgtcacgcg ccacgaagat ttgaaagtga ttatcgacca cttcgagaaa      2040
tatccgctga ttacccagaa attgggcgat acaagttgt ttaaacaggc attcagcgtc      2100
atggagaaca agaacatct taaggagaat gggattaagg agctcgtacg aatcaaagct      2160
aagatgaatt ggggtctcaa tgacgaattg aaaaaagcat tccagagaa catcagcaaa      2220 gagcgccccc ttatcaataa gaacattccg aatctcaaat ggctggctgg attcacatct      2280
ggtgaaggca cattctacgt gcacctagca aagcccaccc gccagaacaa ggtacaggtg      2340
cgactgaggt tcataatcgg ccagcacatc cgagacaaga acctgatgaa ttcattgata      2400
acatacctag gctgtggtac gatccaggag aagaacaggc taagggcag tatgctccac      2460 ttcatagtaa ctaaattcag cgatatcaac gacaagatca ttccggtatt ccaggaaaat      2520
actctgattg gcgtcaaact cgaggacttt gaagattggt gcaaggttgc caaattgatc      2580
gaagagaaga aacacctgac cgaatccggt ttggatgaga ttaagaaaat caagctgaac      2640
atgaacaaag gtcgtgtctt cgctagcacc ggttctgagc cacctcgggc tgagaccttt      2700
gtattcctgg acctagaagc cactgggctc ccaaacatgg accctgagat tgcagagata      2760
tccctttttg ctgttcaccg ctcttccctg gagaacccag aacgggatga ttctggttcc      2820
ttggtgctgc cccgtgttct ggacaagctc acactgtgca tgtgcccgga gcgcccctttt    2880 actgccaagg ccagtgagat tactggtttg agcagcgaaa gcctgatgca ctgcgggaag     2940
gctggtttca tggcgctgt ggtaaggaca ctgcagggct tcctaagccg ccaggagggc      3000
cccatctgcc ttgtgcccca caatggcttc gattatgact tccccactgct gtgcacggag    3060 ctacaacgtc tgggtgccca tctgccccaa gacactgtct gcctggacac actgcctgca    3120 ttgcgggggcc tggaccgtgc tcacagccac ggcaccaggg ctcaaggccg caaaagctac   3180
agcctggcca gtctcttcca ccgctacttc caggctgaac ccgtgctgc ccattcagca     3240 gaaggtgatg tgcacaccct gcttctgatc ttcctgcatc gtgctcctga gctgctcgcc    3300
tgggcagatg agcaggcccg cagctgggct catattgagc ccatgtacgt gccacctgat    3360
ggtccaagcc tcgaagcc                                                   3378
```

<210> SEQ ID NO 45
<211> LENGTH: 3378
<212> TYPE: DNA
<213> ORGANISM: artificial sequence
<220> FEATURE:
<223> OTHER INFORMATION: MegaTAL + Trex2 polynucleotide sequence

```
<400> SEQUENCE: 45
atgggatcct gcaggtatcc atatgatgtc ccagattatg cgccacctaa gaagaaacgc      60
aaagtcgtgg atctacgcac gctcggctac agtcagcagc agcaagagaa gatcaaaccg     120
aaggtgcgtt cgacagtggc gcagcaccac gaggcactgg tgggccatgg gtttacacac     180
gcgcacatcg ttgcgctcag ccaacacccg gcagcgttag ggaccgtcgc tgtcacgtat     240
cagcacataa tcacggcgtt gccagaggcg acacacgaag acatcgttgg cgtcggcaaa     300
cagtggtccg gcgcacgcgc cctggaggcc ttgctcacgg atgcggggga gttgagaggt     360
ccgccgttac agttggacac aggccaactt gtgaagattg caaaacgtgg cggcgtgacc     420
gcaatggagg cagtgcatgc atcgcgcaat gcactgacgg gtgcccccct gaacctgacc     480
ccggaccaag tggtggctat cgccagcaac aatggcggca agcaagcgct cgaaacggtg     540
cagcggctgt tgccggtgct gtgccaggac catggcctga ccccggacca agtggtggct     600
atcgccagca acggtggcgg caagcaagcg ctcgaaacgg tgcagcggct gttgccggtg     660
ctgtgccagg accatggcct gactccggac caagtggtgg ctatcgccag ccacgatggc     720
ggcaagcaag cgctcgaaac ggtgcagcgg ctgttgccgg tgctgtgcca ggaccatggc     780
ctgactccgg accaagtggt ggctatcgcc agccacgatg cggcaagca agcgctcgaa     840 acggtgcagc ggctgttgcc ggtgctgtgc caggaccatg gcctgacccc ggaccaagtg     900
gtggctatcg ccagcaacgg tggcggcaag caagcgctcg aaacggtgca gcggctgttg     960
ccggtgctgt gccaggacca tggcctgacc ccggaccaag tggtggctat cgccagcaac    1020
ggtggcggca agcaagcgct cgaaacggtg cagcggctgt tgccggtgct gtgccaggac    1080
catggcctga ctccggacca agtggtggct atcgccagcc acgatggcgg caagcaagcg    1140
ctcgaaacgg tgcagcggct gttgccggtg ctgtgccagg accatggcct gaccccggac    1200
caagtggtgg ctatcgccag caacggtggc ggcaagcaag cgctcgaaac ggtgcagcgg    1260
ctgttgccgg tgctgtgcca ggaccatggc ctgactccgg accaagtggt ggctatcgcc    1320
agccacgatg cggcaagca agcgctcgaa acggtgcagc ggctgttgcc ggtgctgtgc    1380
caggaccatg gcctgactcc ggaccaagtg gtggctatcg ccagccacga tggcggcaag    1440
caagcgctcg aaacggtgca gcggctgttg ccggtgctgt gccaggacca tggcctgacc    1500
ccggaccaag tggtggctat cgccagcaac ggtggcggca agcaagcgct cgaaagcatt    1560
gtggcccagc tgagccggcc tgatccggcg ttggccgcgt tgaccaacga ccacctcgtc    1620
gccttggcct gcctcggcgg acgtcctgcc atggatgcag tgaaaaaggg attgccgcac    1680
gcgccggaat tgatcagaag agtcaatcgc cgtattggcg aacgcacgtc ccatcgcgtt    1740
gcgatatcta gagtgggagg aagctcgcgc agagagtcca tcaacccatg gattctgact    1800
ggtttcgctg atgccgaagc atccttcatg ctaagaatcc gtagcgcgaa caaccggtca    1860
gtagggtact acactgacct ggtattcgaa atcactctgc acaacaagga caaatcgatt    1920
ctggagaata tccagtcgac ttggaaggtc ggcacaatca caaccgaggc gacggcacc     1980 gtcagactga gcgtcacgcg ccacgaagat ttgaaagtga ttatcgacca cttcgagaaa    2040
tatccgctga ttacccagaa attgggcgat tacaagttgt ttaaacaggc attcagcgtc    2100
atggagaaca agaacatctc taaggagaat gggattaagg agctcgtacg aatcaaagct    2160
aagatgaatt ggggtctcaa tgacgaattg aaaaaagcat tcccagagaa catcagcaaa    2220
gagcgccccc ttatcaataa gaacattccg aatctcaaat ggctggctgg attcacatct    2280
ggtgaaggca cattctacgt gcacctagca aagcccaccc gccagaacaa ggtacaggtg    2340
```

```
cgactgaggt tcataatcgg ccagcacatc cgagacaaga acctgatgaa ttcattgata      2400
acatacctag gctgtggtac gatccaggag aagaacaggt ctaagggcag tatgctccac      2460
ttcatagtaa ctaaattcag cgatatcaac gacaagatca ttccggtatt ccaggaaaat      2520
actctgattg gcgtcaaact cgaggacttt gaagattggt gcaaggttgc caaattgatc      2580
gaagagaaga aacacctgac cgaatccggt ttggatgaga ttaagaaaat caagctgaac      2640
atgaacaaag gtcgtgtctt cgctagcacc ggttctgagc cacctcgggc tgagaccttt      2700
gtattcctgg acctagaagc cactgggctc ccaaacatgg accctgagat tgcagagata      2760
tccctttttg ctgttcaccg ctcttccctg gagaacccag aacgggatga ttctggttcc      2820
ttggtgctgc cccgtgttct ggacaagctc acactgtgca tgtgcccgga gcgccccttt      2880
actgccaagg ccagtgagat tactggtttg agcagcgaaa gcctgatgca ctgcgggaag      2940
gctggtttca atggcgctgt ggtaaggaca ctgcagggct cctaagccg ccaggagggc       3000 cccatctgcc ttgtggccca caatggcttc gattatgact tcccactgct gtgcacggag      3060
ctacaacgtc tgggtgccca tctgccccaa gacactgtct gcctggacac actgcctgca      3120
ttgcggggcc tggaccgtgc tcacagccac ggcaccaggg ctcaaggccg caaaagctac      3180
agcctggcca gtctcttcca ccgctacttc caggctgaac ccagtgctgc ccattcagca      3240
gaaggtgatg tgcacaccct gcttctgatc ttcctgcatc gtgctcctga gctgctcgcc      3300
tgggcagatg agcaggcccg cagctgggct catattgagc ccatgtacgt gccacctgat      3360
ggtccaagcc tcgaagcc                                                    3378

<210> SEQ ID NO 46
<211> LENGTH: 830
<212> TYPE: DNA
<213> ORGANISM: Homo sapiens

<400> SEQUENCE: 46
ggtggaacaa gatggattat caagtgtcaa gtccaatcta tgacatcaat tattatacat        60
cggagccctg ccaaaaaatc aatgtgaagc aaatcgcagc ccgcctcctg cctccgctct       120
actcactggt gttcatcttt ggttttgtgg caacatgct ggtcatcctc atcctgataa        180
actgcaaaag gctgaagagc atgactgaca tctacctgct caacctggcc atctctgacc       240 tgttttcct tcttactgtc cccttctggg ctcactatgc tgccgcccag tgggactttg        300
gaaatacaat gtgtcaactc ttgacaggc tctattttat aggcttcttc tctggaatct        360
tcttcatcat cctcctgaca atcgataggt acctggctgt cgtccatgct gtgtttgctt       420
taaaagccag gacggtcacc tttggggtgg tgacaagtgt gatcacttgg gtggtggctg       480
tgtttgcgtc tctcccagga atcatcttta ccagatctca aaaagaaggt cttcattaca       540
cctgcagctc tcattttcca tacagtcagt atcaattctg gaagaatttc cagacattaa       600
agatagtcat cttggggctg gtcctgccgc tgcttgtcat ggtcatctgc tactcgggaa       660
tcctaaaaac tctgcttcgg tgtcgaaatg agaagaagag gcacagggct gtgaggctta       720
tcttcaccat catgattgtt tatttctct tctgggctcc ctacaacatt gtccttctcc        780 tgaacaccctt ccaggaattc tttggcctga ataattgcag tagctctaac                 830

<210> SEQ ID NO 47
<211> LENGTH: 827
<212> TYPE: DNA
<213> ORGANISM: Homo sapiens
```

```
<400> SEQUENCE: 47
ccaccttgtt ctacctaata gttcacagtt caggttagat actgtagtta ataatatgta    60
gcctcgggac ggttttttag ttacacttcg tttagcgtcg ggcggaggac ggaggcgaga   120
tgagtgacca gaagtagaaa ccaaaacacc cgttgtacga ccagtaggag taggactatt   180
tgacgttttc cgacttctcg tactgactgt agatggacga gttggaccgg tagagacgga   240
caaaaaggaa gaatgacagg ggaagacccg agtgatacga cggcgggtca ccctgaaacc   300
tttatgttac acagttgaga actgtcccga gataaaatat ccgaagaaga gaccttagaa   360
gaagtagtag gaggactgtt agctatccat ggaccgacag caggtacgac acaaacgaaa   420
ttttcggtcc tgcctgtgga aaccccacca ctgttcacac tagtgaaccc accaccgaca   480
caaacgcaga gagggtcctt agtagaaatg gtctagagtt tttcttccag aagtaatgtg   540
gacgtcgaga gtaaaaggta tgtcagtata gttaagacct tcttaaaggt ctgtaatttc   600
tatcagtaga accccgacca ggacggcgac gaacagtacc agtagacgat gagcccttag   660 gattttttgag acgaagccac agctttagtc ttcttctccg tgtcccgaca ctccgaatag   720
aagtggtagt actaacaaat aaaagagaag acccgaggga tgtgtaacag gaagaggact   780
tgtggaaggt ccttaagaaa ccggacttat taacgtcatc gagattg                 827

<210> SEQ ID NO 48
<211> LENGTH: 273
<212> TYPE: PRT
<213> ORGANISM: Homo sapiens

<400> SEQUENCE: 48

Met Asp Tyr Gln Val Ser Ser Pro Ile Tyr Asp Ile Asn Tyr Tyr Thr
1               5                   10                  15

Ser Glu Pro Cys Gln Lys Ile Asn Val Lys Gln Ile Ala Ala Arg Leu
            20                  25                  30

Leu Pro Pro Leu Tyr Ser Leu Val Phe Ile Phe Gly Phe Val Gly Asn
        35                  40                  45

Met Leu Val Ile Leu Ile Leu Ile Asn Cys Lys Arg Leu Lys Ser Met
    50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
            100                 105                 110

Phe Ser Gly Ile Phe Phe Ile Ile Leu Leu Thr Ile Asp Arg Tyr Leu
        115                 120                 125

Ala Val Val His Ala Val Phe Ala Leu Lys Ala Arg Thr Val Thr Phe
    130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
            180                 185                 190

Phe Gln Thr Leu Lys Ile Val Ile Leu Gly Leu Val Leu Pro Leu Leu
        195                 200                 205

Val Met Val Ile Cys Tyr Ser Gly Ile Leu Lys Thr Leu Leu Arg Cys
    210                 215                 220
```

-continued

```
Arg Asn Glu Lys Lys Arg His Arg Ala Val Arg Leu Ile Phe Thr Ile
225                 230                 235                 240

Met Ile Val Tyr Phe Leu Phe Trp Ala Pro Tyr Asn Ile Val Leu Leu
                245                 250                 255

Leu Asn Thr Phe Gln Glu Phe Phe Gly Leu Asn Asn Cys Ser Ser Ser
            260                 265                 270

Asn
```

SEQUENCE SPECIFIC REAGENTS TARGETING CCR5 IN PRIMARY HEMATOPOIETIC CELLS

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Feb. 28, 2023, is named 16604072_ST25.txt and is 149,331 bytes in size.

FIELD OF THE INVENTION

The present invention generally relates to the field of gene therapy, and more specifically to the treatment and prevention of HIV infection. In particular, the invention discloses methods for genetically modifying alleles of C—C chemokine receptor type 5 (CCR5) in primary hematopoietic stem cells involving endonuclease reagents, such as TALE-nucleases, that specifically target the N-terminal region of CCR5, in order to generate lymphoid cells actually resistant to HIV infection.

BACKGROUND OF THE INVENTION

Combination antiretroviral therapy (cART) (also known as Highly Active Antiretroviral Therapy or HAART) limits Human immunodeficiency virus-I (HIV-1) replication and retards disease progression. Although cART remains the "gold standard" for treatment of HIV infection, the requirement for lifelong treatment poses multiple challenges such as stigma, untenable pill burden, drug toxicities, and the threat of the emergence of drug-resistant viruses. Additionally, traditional antiretroviral therapy, while successful at delaying the onset of AIDS or death, has yet to provide a functional cure. Alternative treatment strategies are clearly needed.

HIV-1 entry into target cells is initiated by a high-affinity binding of HIV-1 envelope gp120 glycoprotein to the primary receptor CD4, and the subsequent interaction of CD4-bound gp120 with the appropriate chemokine receptor (co-receptor), either CXCR4 or CCR5 [Feng et al. (1996) *Science* 272:872-877; Deng et al. (1996) *Nature* 381:661-666]. Most HIV strains are dependent upon the CD4/CCR5 receptor/co-receptor combination to gain entry into a cell and are termed CCR5 (or R5) tropic. In addition, a patient, known as the Berlin Patient, suffering from acute myeloid leukemia and HIV-1 infection was given a donor cells, for its bone marrow transplant, from an individual homozygous for naturally occurring 32 base pair deletion in CCR5. Following the success of the transplant, the patient discontinued HIV-1 therapy and has no detectable viremia for over six years [Allers et al. (2011) Evidence for the cure of HIV infection by CCR5 Δ32/Δ32 stem cell transplantation, *Blood*, 117:2791-2799]. Disruption of CCR5 gene thus became a gene therapy target for curative HIV.

Gene disruption can be achieved through the use of site specific nucleases such as engineered zinc finger nucleases (ZFN), transcription-activator like effector nucleases (TALE-nucleases), meganucleases (including fusions of homing endonucleases with TALE so-called MegaTAL) or RNA-guided endonucleases (including Cas9 and/or Cpf1) [Waddington, S. N. (2016) A Broad Overview and Review of CRISPR-Cas Technology *Curr. Stem. Cell. Rep.* (2016) 2:9-20]. These site-specific nucleases introduce DNA double strand break at a targeted locus, whose subsequent repair is exploited to achieve different outcomes. In general, the non-homologous end joining (NHEJ) repair pathway is accessed and the end result is insertion/deletions (indels) at the break site resulting in gene disruption (U.S. Pat. No. 9,458,439). Alternatively repair pathway based on homologous recombination can be used to copy information from an introduced DNA homology template. Such homology directed repair (HDR) can promote a specific addition of exogenous or endogenous polynucleotide sequence that can be expressed at the same time that gene disruption is achieved (U.S. Pat. No. 8,921,332).

In 2009, a phase1 clinical trial NCT00842634 has evaluated safety of modifying autologous CD4+ T cells in HIV-1 infected patients using ZFN. The results were published in 2014 demonstrating the safe approach of this gene therapy strategy [Tebas et al. (2014) *N. Engl. J. Med.* 370(10):901-910]. The efficacy of ZFN at the genomic locus was however between 11 and 28%, and HIV resistance could be observed only in one patient who was heterozygous for CCR5 Δ32, suggesting that homozygous deletion of CCR5 is necessary to achieve HIV resistance. Engineering Hematopoietic Stem and Progenitor Cells (HSPC) instead of CD4+ T cells has the potential to provide a long-lasting source of modified cells and to additionally protect the CD4+ myeloid cells that are also susceptible to HIV-1 infection. In animal models, it has been showed that transplantation of CCR5 inactivated HSPC into NSG mice could give rise to CCR5 deficient CD4+ T cell progeny [Hofer et al. (2013) Pre-clinical modeling of CCR5 knockout in human hematopoietic stem cells by zinc finger nucleases using humanized mice. *J. Infect. Dis.* 208 Suppl 2:S160-4]. In clinical application, a major challenge of engineered nucleases is the potential of off-target genome modifications. For instance, the CCR5 ZFN pair in clinical development previously mentioned led to 5,39% disruption of the top predicted off-target site, the highly related CCR2 gene.

Various CCR5-specific TALE-nucleases have also been described in the art in an attempt to more efficiently cleave CCR5.

In WO2011146121 different TALE-nuclease scaffolds were tested for cleavage activity at the CCR5 locus located at 550 base pair from ATG start codon. The best scaffold approached 50% NHEJ events when tested in K562 cell line, but this was not tested in primary cells where it would probably account much less efficiency.

In WO2012093833, another TALE-nuclease targeting CCR5 was designed to cleave at approximatively 900 base pair from the CCR5 start codon. However, the same tested in HEK293T/17 cells was reported to provide a maximum of 3% NHEJ events.

Mussolino et al. [*Nucleic Acids Res.* (2014) 42(10):6762-73] describe different CCR5 TALE-nuclease, which were all designed to cleave the same region at approximatively 160 base pair from ATG start codon of CCR5. The best reported TALE-nuclease among them showed 24% of NHEJ activity when expressed in HEK293T, while most of them showed significant off-target activity at the CCR2 locus.

Ramalingam et al. [*Curr. Gene. Ther.* (2014) 14(6):461-72] describe another CCR5 TALE-nuclease designed to cleave at approximatively 550 base pair from CCR5 start codon. This CCR5 TALE-nuclease was used to generate human induced Pluripotent Stem Cells by inserting a Oct4/Sox2/Klf4/Lin28/Nanog/eGFP gene cassette at the CCR5 locus. However, this had not been tested for its efficacy in a bulk population of primary cells.

WO2015169314 describes further CCR5 TALE-nucleases, which were designed to cleave at approximatively 175 base pair from CCR5 start codon. These TALE-nucleases amounted 50% of NHEJ events when applied in primary T-cells. However, these TALE-nucleases showed between 1.13 and 6.24% off-target NHEJ events at the CCR2 locus [*Nucleic Acids Res.* (2015) 43(11):5560-7]. When considering CCR5 gene disruption in HSPC for stem cell transplantation, such levels of inactivation of CCR2 could be problematic. It has been demonstrated for instance that in mice CCR2 plays an important role for extravasation, adhesion, and transmigration of monocytes into inflamed tissue [review in Chu et al. (2014) Role of CCR2 in inflammatory conditions of the central nervous system. *J. Cereb. Blood Flow Metab.* 34(9):1425-9] and for dendritic cell activation [Chiu et al. (2004) Impaired lung dendritic cell activation in CCR2 knockout mice *Am. J. Pathol.* 165(4): 1199-209]. Since stem cell transplantation will give rise to all hematopoietic cells, concomitant disruption of CCR2 with CCR5 may impair immune response mechanisms. It is therefore critical, in view of the permanent engraftment of gene-edited HSC in patient's bone marrow, that only CCR5 be inactivated, while minimizing off-target effects and possible resulting chromosomal translocations.

Thus, the TALE-nucleases described in the art have been designed to cleave CCR5 alleles either close to the initial CCR5 Δ32 mutation (at 550 base pair from ATG start codon) or the cleavage site already used with respect to the ZFN pair developed in the clinic (at 160 base pair from the ATG start codon) or even further downstream in the C-terminal transmembrane region.

Given the above limitations of the available CCR5 reagents, there is still a need for highly active site-specific nuclease reagents targeting CCR5, that would reach high level of gene disruption, without cleaving CCR2 gene, and that would preferably disrupt the N-terminus part of the CCR5 protein, so as to remove efficiently almost all possible residual polypeptides that could have a critical function in HIV interaction.

SUMMARY OF THE INVENTION

Non-homologous end-joining (NHEJ) and homology-directed repair (HDR) are the two major pathways used to repair DNA breaks in living cells. The latter pathway repairs the break in a template-dependent manner (HDR naturally utilizes the sister chromatid as a DNA repair template). Homologous recombination has been used for decades to precisely edit genomes with targeted DNA modifications using exogenously supplied donor template. The artificial generation of a double strand break (DSB) at the target location using rare-cutting endonucleases considerably enhances the efficiency of homologous recombination (e.g. U.S. Pat. No. 8,921,332) or, in the absence of repair template, the rate of mutagenesis (e.g. U.S. Pat. No. 9,458,439).

Successful experiments have shown that it was possible to specifically inactivate CCR5 in T-cells, making same resistant to HIV. However, the sequence specific reagents in the art have not shown enough efficiency and specificity into primary cells to meet clinical needs.

The new sequence specific reagents of the present invention overcome most limitations of former reagents by targeting specific allelic sequences encoding the N-terminal region of CCR5.

These new reagents have unexpectedly shown improved cleavage efficiency and specificity over the previous available reagents.

The invention provides introducing the nucleic acid sequence(s) encoding said new CCR5 sequence specific reagents into hematopoietic primary cells, alone or in conjunction with exogenous coding sequences, to make those cells resistant to HIV infection, while optionally conferring to these cells higher immune activity, longer persistence and resistance to drugs.

The present application is more particularly drawn to the vectors, polynucleotides and polypeptides encoding the CCR5 specific reagents of the present invention and to the resulting primary cells, which are useful for anti-HIV therapy.

BRIEF DESCRIPTION OF THE FIGURES AND TABLES

FIG. 1: Localization of the target sequences of the various sequence specific reagents tested at the CCR5 locus. Top strand DNA (SEQ ID NO:45). Bottom strand DNA (SEQ ID NO:46), and encoded protein (SEQ ID NO:47). The left and right target sequences (binding sequences) for TALE-nucleases or ZFN nucleases, the guided RNA target sequences used for CRISPR/Cas nuclease, the TAL binding sequence (MT-T) and the I-OnuI cleavage sequence (MT-M) of the MegaTAL nuclease are shown with respect to the genomic sequence CCR5 sequence (SEQ ID NO:1) encoding the first 273 amino acids of the protein.

Figure 2:
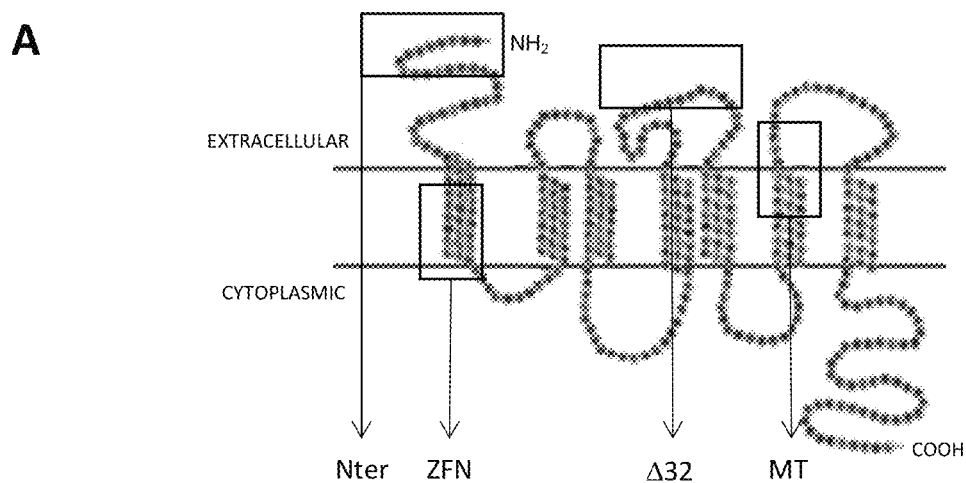
Figure 2:
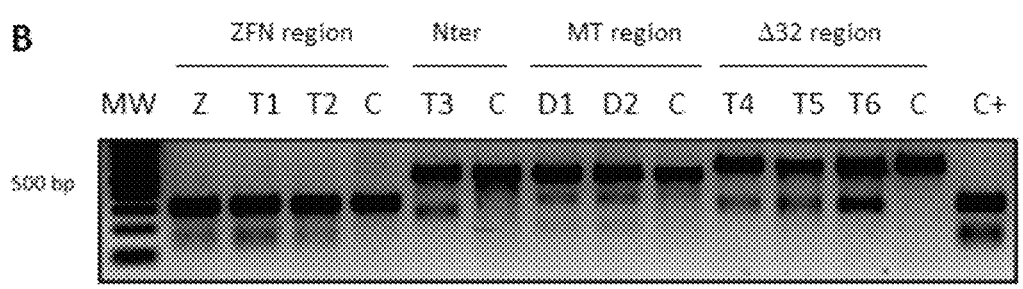
Figure 2:
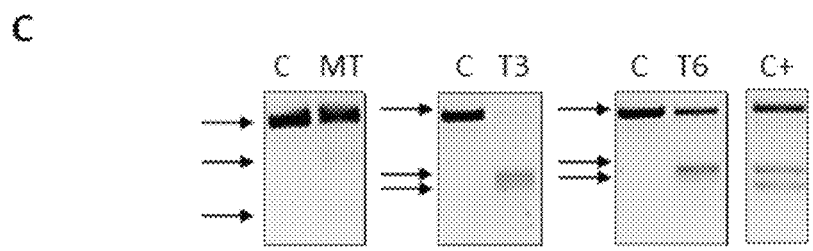

FIG. 2: Experimental design and results referred to in Example 1. 2A: Schematic representation of CCR5 protein at the cytoplasmic membrane, squares are highlighting the localization of the different specific nucleases target sites: according to the present invention (at CCR5 N-terminal region (Nter)), at the region of the ZFN used in the clinic (ZFN), at the Δ 32 region (Δ32) and at the MegaTAL target site (M-T). 2B: T7 endonuclease 1 assay results of the different nucleases tested in U20S cell line. 2C: nuclease activity of T3, T6 and MT delivered as mRNA in K562 cell line. Z: ZFN, T1-6: TALEN1-6, MT: MegaTAL, D: dose of MegaTAL, C: negative control (i.e. no nuclease) C+: positive control of T7 Endonuclease 1 assay.

Figure 3:
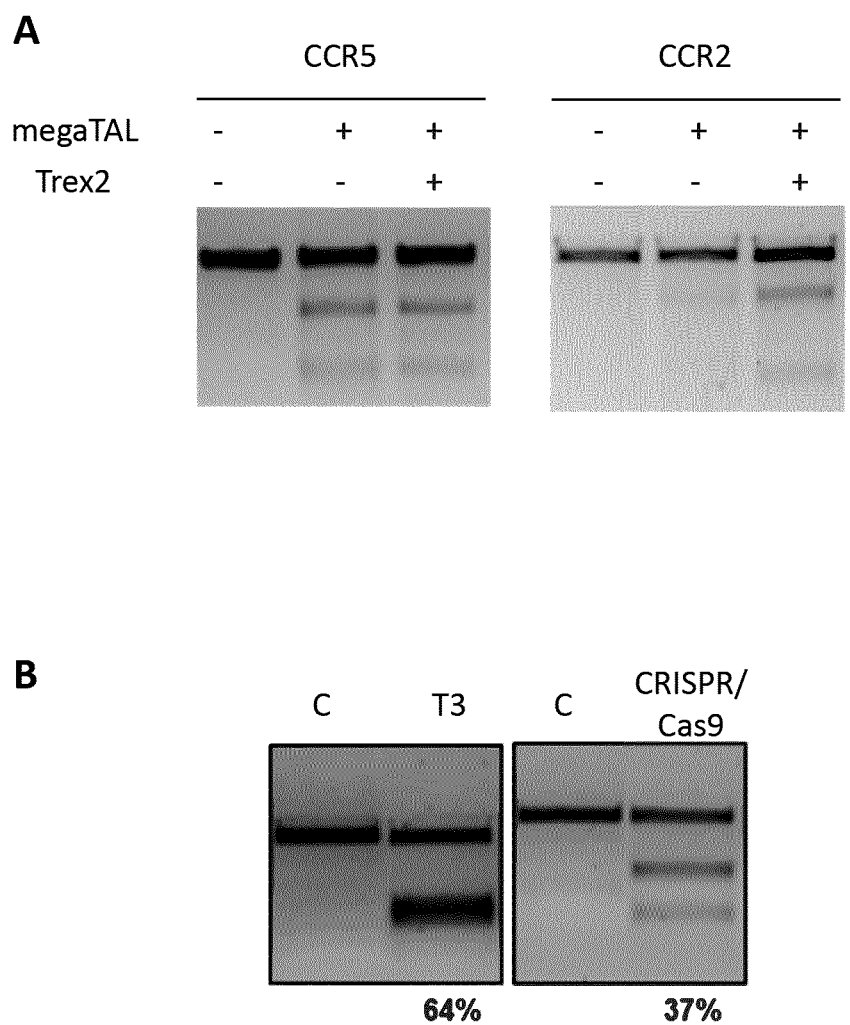
Figure 3:
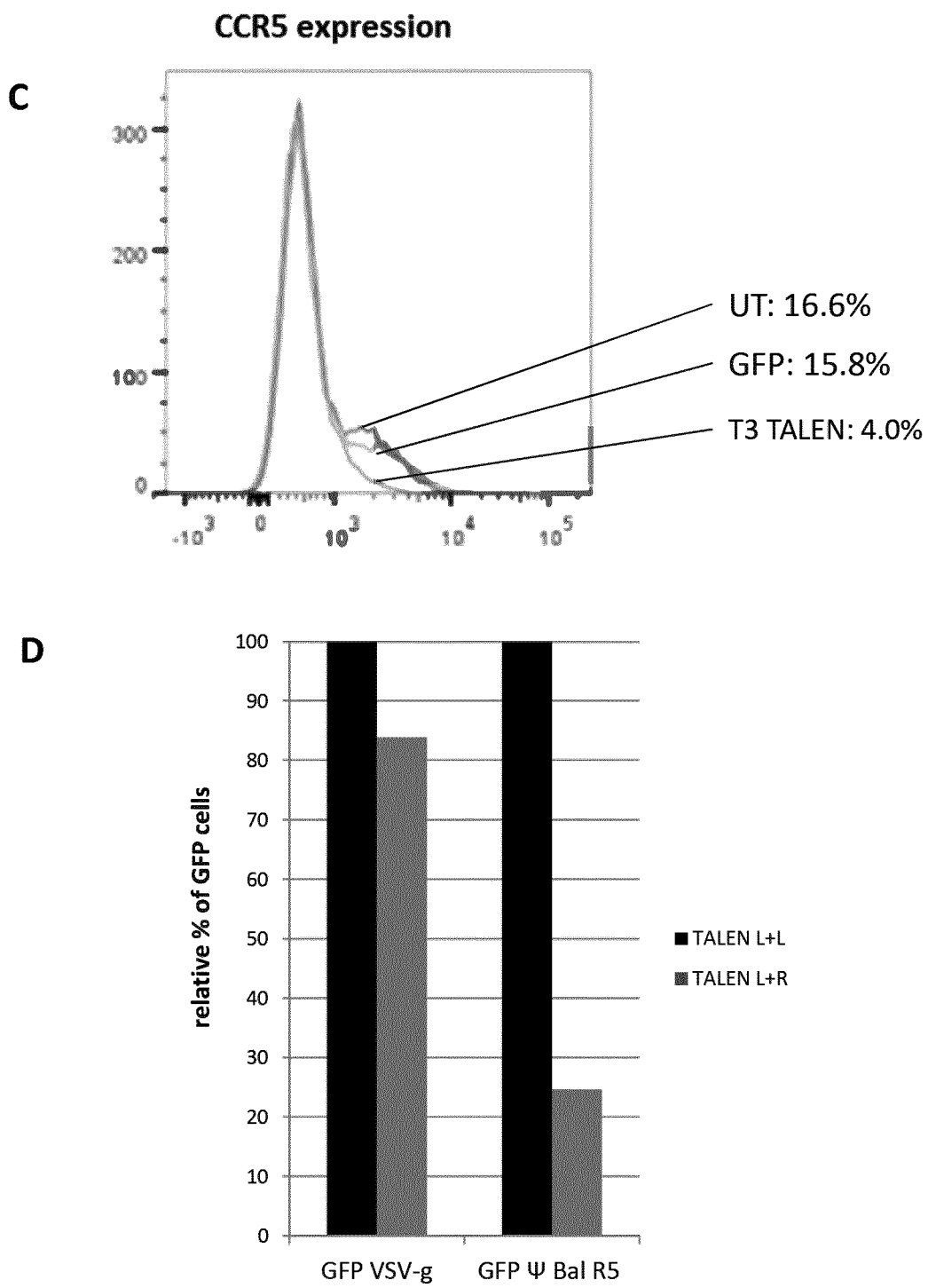

FIG. 3: Evaluation of CCR5 specific nucleases in CD4+ T-cells. 3A: Evaluation of megaTAL activity at the CCR5 (left panel) or CCR2 (right panel) loci by T7 Endonuclease 1 assay with or without co-expression of Trex2. 3B: T7 Endonuclease 1 assay results from TALEN® (T3) or CRISPR-Cas9 with gRNA #3 (CRISPR/Cas9) treated cells. 3C: CCR5 immuno-staining of TALEN® T3 treated (T3), GFP treated (GFP) or untreated (UT) cells. Percentage of CCR5 positive cells is provided on the right. 3D: Challenge assay results, percentage of GFP positive CD4+ T-cells that were electroporated with either TALEN® Left monomer only (black bars) or with TALEN® Left and Right monomers (grey bars) and transduced with pseudotyped lentiviral vectors either VSV-g (CCR5-independent) or tp bal R5 (CCR5-dependent) viral vectors as further detailed in Example 2.

Figure 4:
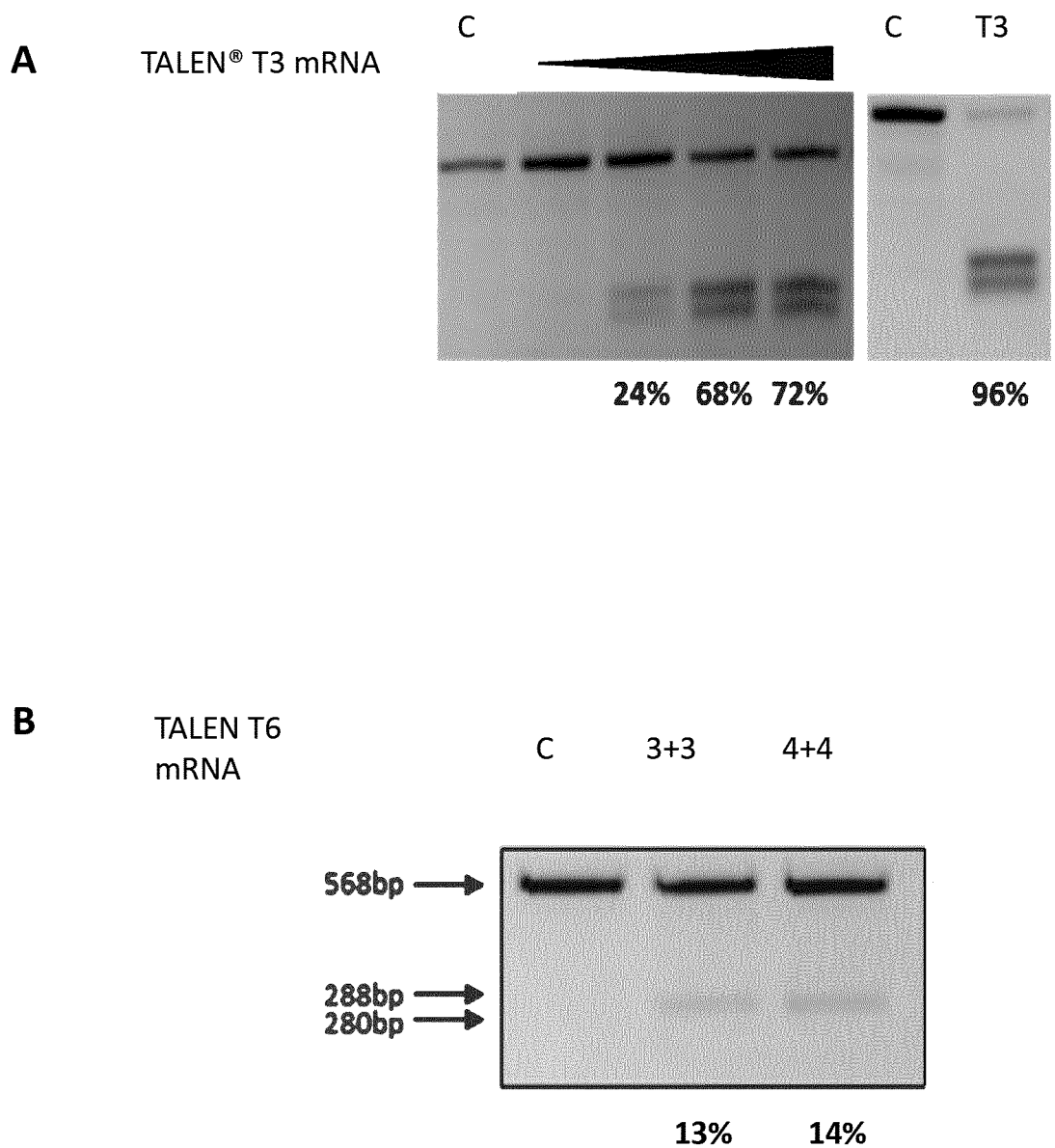
Figure 4:
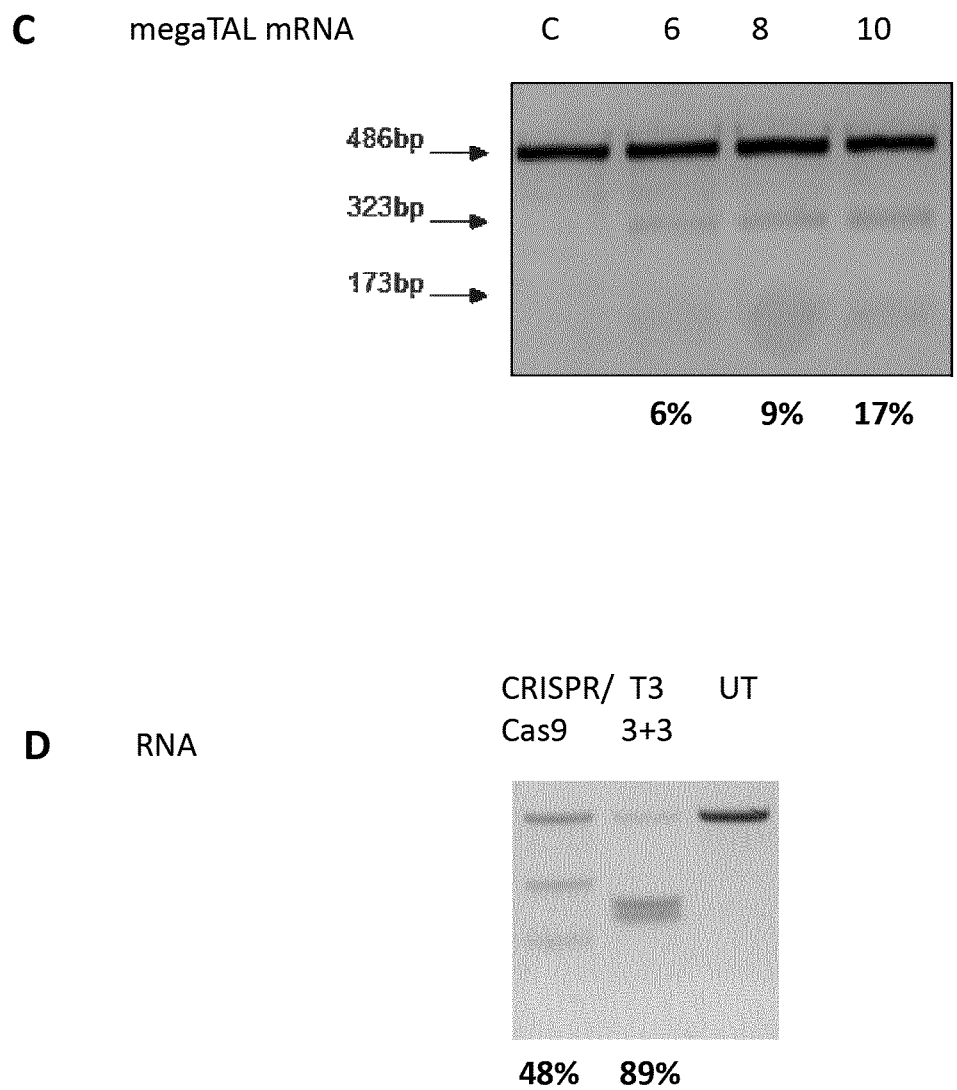

FIG. 4: Optimization of site specific nucleases targeting CCR5 locus in CD34+ Hematopoietic Stem and Progenitor Cells (HSPC). 4A: TALEN® T3 mRNA nucleofection. T7 Endonuclease 1 assay results of nucleofected mRNAs dose response (left panel). Optimized dose (3 µg of each mRNA encoding T3 TALEN® unit: T3) shown in right panel. Percentage of induced mutagenesis is provided. 4B: TALEN T6 mRNA nucleofection. T7 Endonuclease 1 assay results of 3 µg (3+3) and 4 µg (4+4) of each TALEN® T6 unit mRNA nucleofection. 4C: MegaTAL mRNA nucleofection. T7 Endonuclease 1 assay results of 6, 8, or 10 µg of nucleofected megaTAL mRNAs. 4D: Optimization of CRISPR/Cas9 nucleofection and comparison to TALEN® T3 (T3). T7 Endonuclease 1 assay results. Quantification of induced mutagenesis are provided. C: negative control (i.e. no nuclease).

Figure 5:
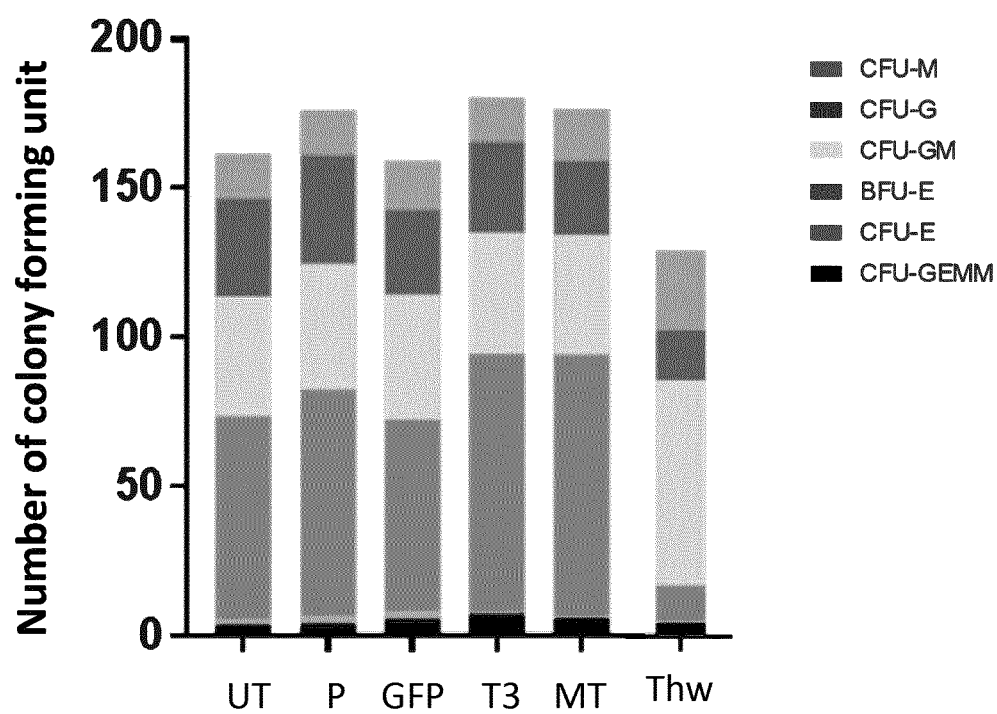

FIG. 5: In vitro functionality evaluation of edited HSPC cells. Numbers of colonies from HSPC obtained after no nucleofection (UT), nucleofection without mRNA (P), nucleofection with GFP encoding mRNA (GFP), nucleofection with TALEN® T3 encoding mRNAs (T3), nucleofection with megaTAL encoding mRNA (MT), or directly 2 days post thawing (Thw). CFU-M: Colony Forming Unit-Megakaryocyte; CFU-G: Colony Forming Unit-Granulocyte; CFU-GM: Colony Forming Unit-Granulocyte and Monocyte/Macrophage; BFU-E: Burst Forming Unit-Erythroid, CFU-E: Colony-Forming Units of Erythroid, CFU-EGMM: Colony-Forming Unit-Granulocyte, Erythrocyte, Monocyte/macrophage, Megakaryocyte.

Figure 6:
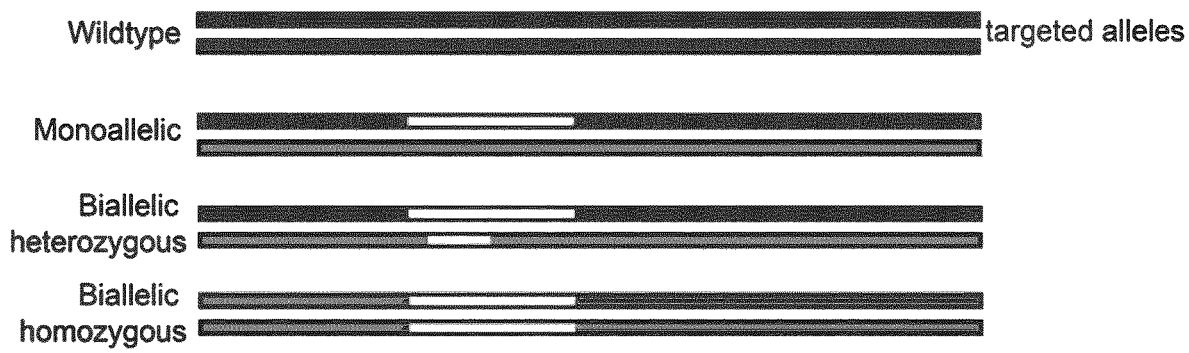
Figure 6:
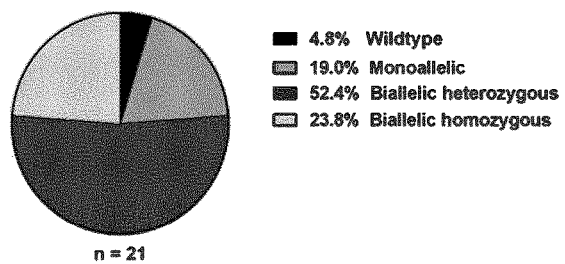
Figure 6:
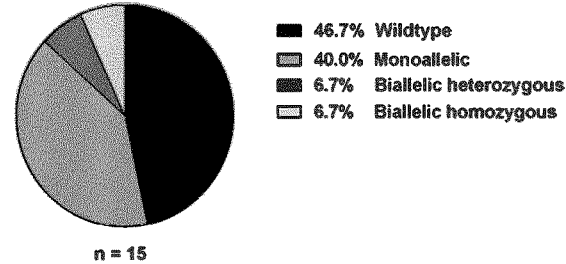

FIG. 6: allele sequence analysis 6A: Representation of the different mutation events that could have occurred in HSPC cells and that would be obtained in the derived colonies in the CFU assay. 6B: Mutation events distribution observed in 21 colonies derived from T3 TALEN® edited HSPC. 6C: Mutation events distribution observed in 15 colonies derived from megaTAL edited HSPC.

Figure 7:
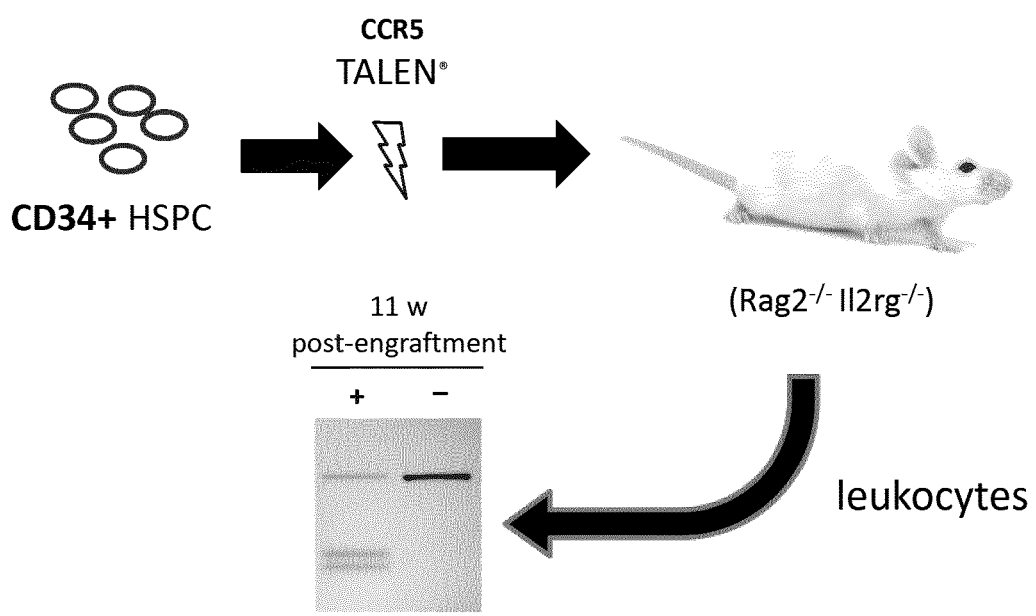

FIG. 7: Preclinical assay in mice. Representation of the preclinical experiment design and results. HSPC edited (+) or not (−) with CCCR5 T3 TALEN® mRNAs are transplanted into immune-deficient mice for reconstitution of an immune system. Leukocytes recovered 11 weeks after transplantation are analyzed by T7 endonuclease assay for validation of CCR5 genome modification.

Figure 8:
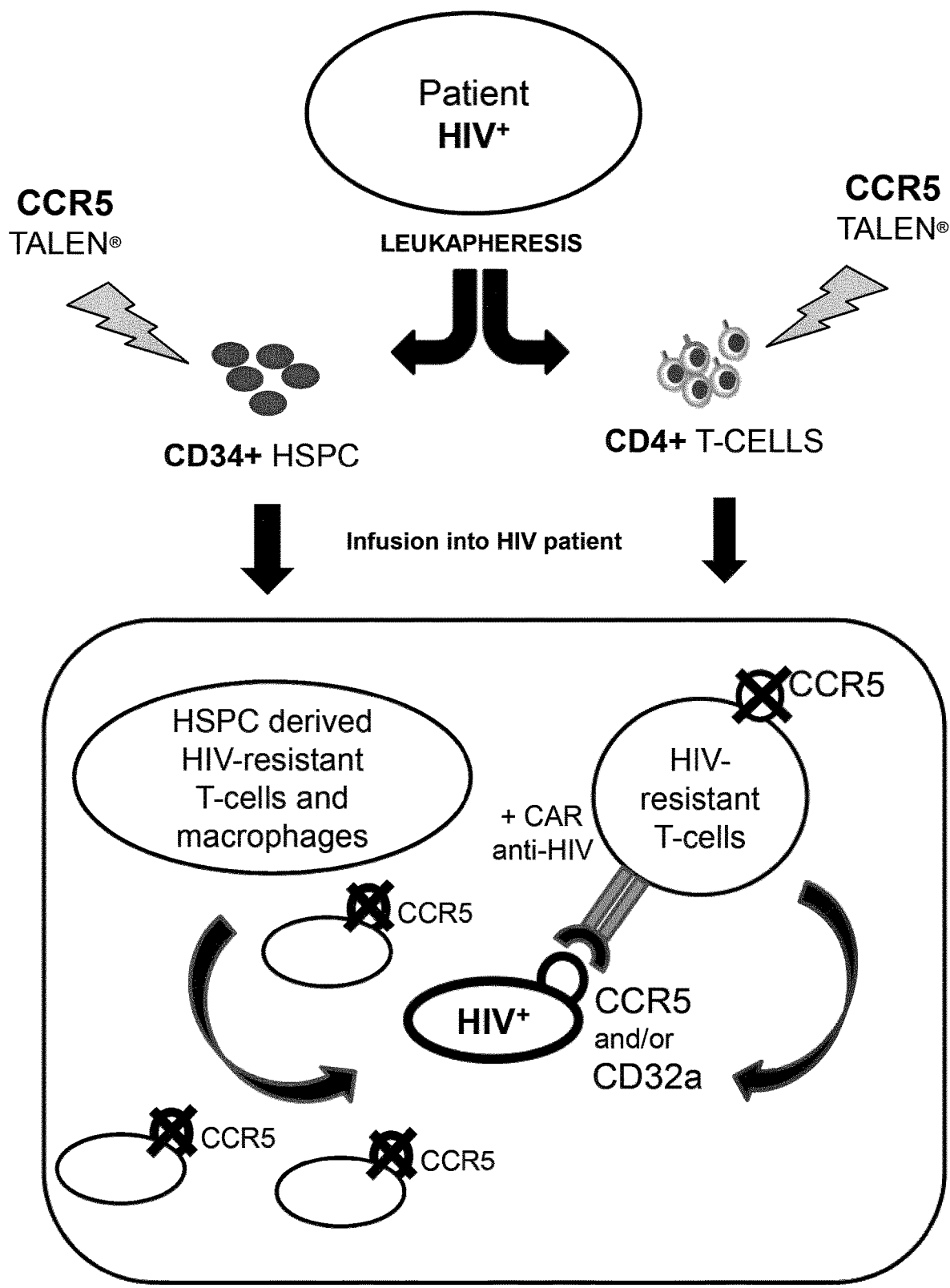

FIG. 8: Example of clinical scheme envisioned by the present invention, where population of CD34+ and CD4+ cells are drawn from a HIV patient, separately treated with CCR5 sequence specific reagents, optionally (not shown) further treated with specific endonucleases directed against HIV genome (HIV clipping) or any anti-HIV treatment, and re-infused into the patient. The re-implantation of the cells may be performed after lymphodepletion conditioning treatment (not shown). Then, the engineered HSPC get permanently engrafted and produce CCR5 negative HIV resistant T-cells and macrophages. On their own, the T-cells obtained from the patient can be activated and expanded over several days. They can be optionally further transfected with retroviral vectors encoding anti-HIV CARs, such as anti-CD32a CAR and/or anti-CCR5 CARs, to redirect their immune activity towards reservoir T-cells or CCR5 positive T-cells remaining into the patient. The T-cells can be infused back into the patient in an autologous fashion, concomitantly or after the HSPC's engraftment.

Figure 9:
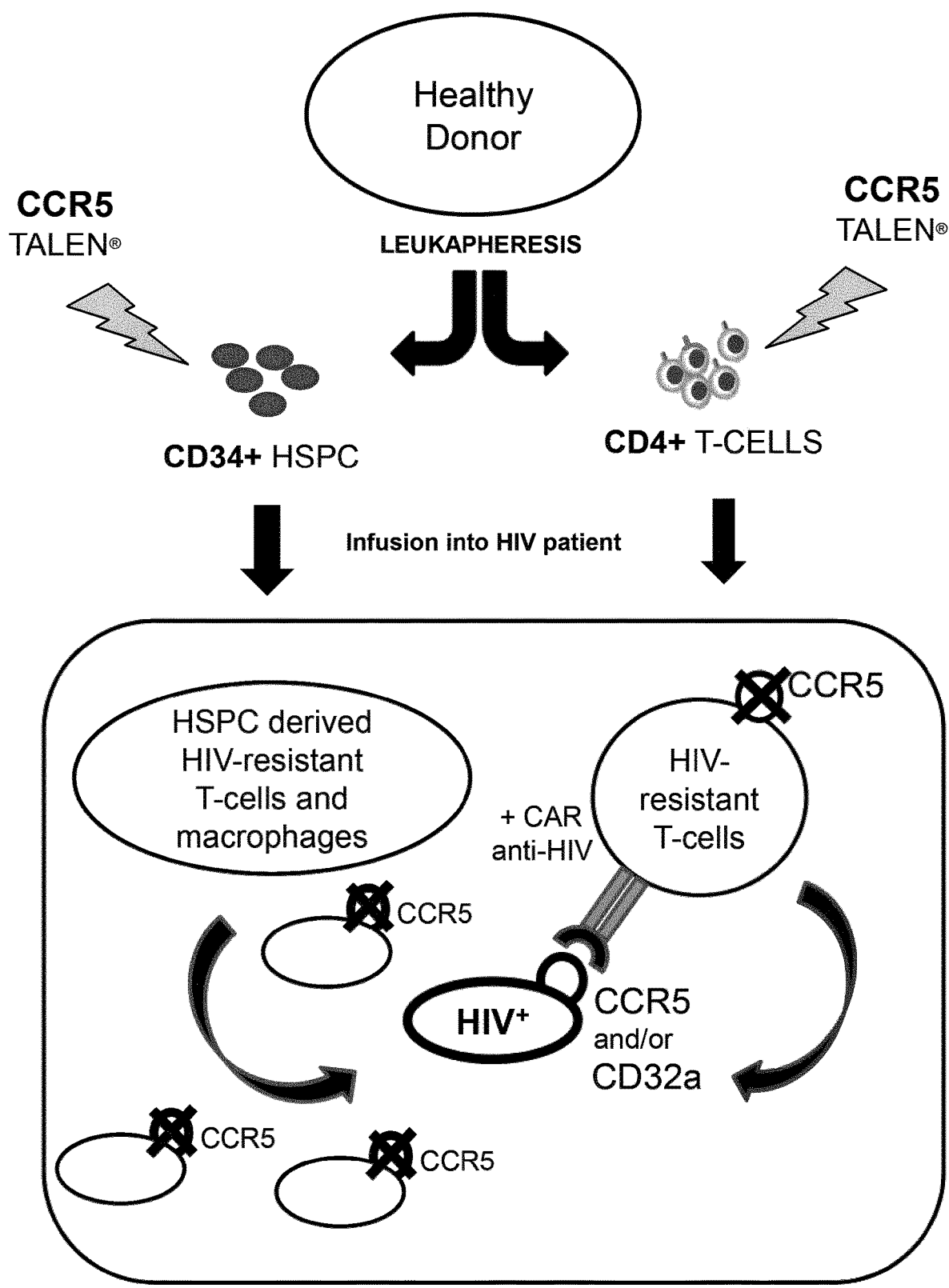

FIG. 9: Example of clinical scheme envisioned by the present invention, similar to FIG. 8, to the difference that population of CD34+ and CD4+ cells are drawn from a healthy donor. By contrast to FIG. 8, an additional step is performed with respect to the population of primary T-cells, in which the expression of TCR is reduced, modified or suppressed, to reduce GvHD alloreactivity prior to infusion into the patient.

Figure 10:
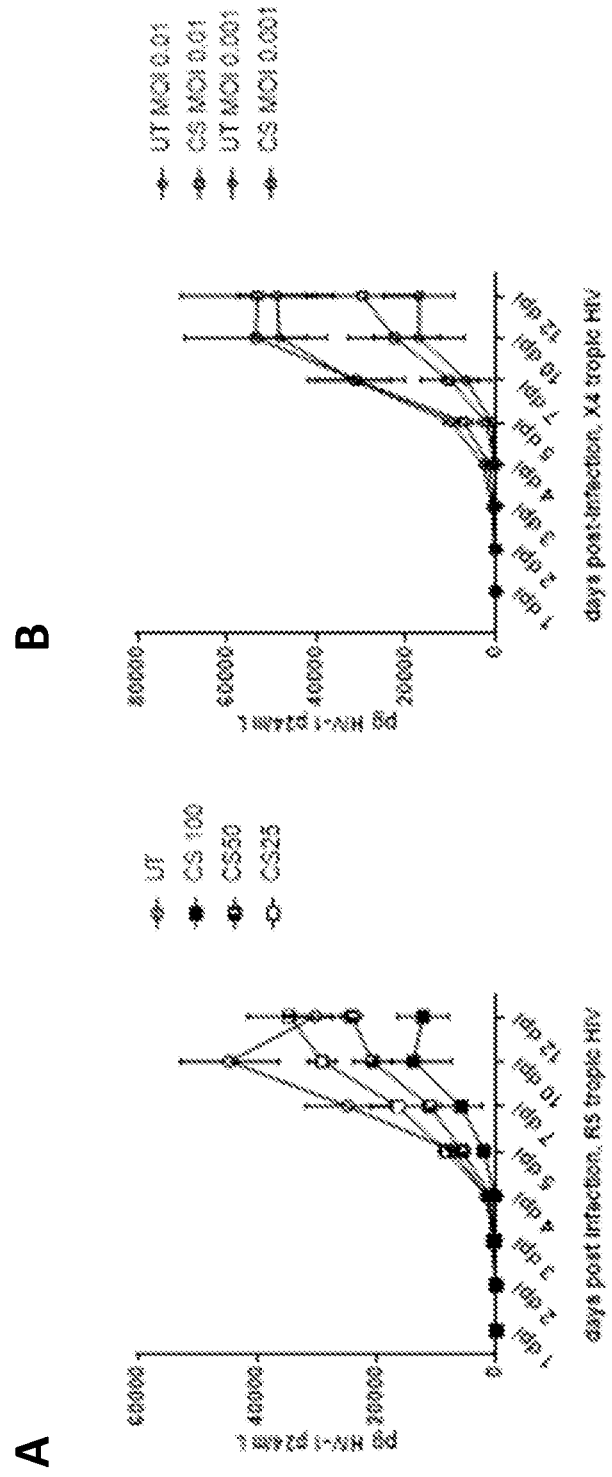

FIG. 10: (A) Challenge with R5 tropic HIV. Infection of TALEN® edited cells with R5 tropic HIV (strain JR-FL, MOI of 0.001). Levels of p24 in the supernatants of undiluted edited cells (CS100), CCR5 edited cells mixed 1:1 (CS50) or 1:3 (CS25) with unedited cells, respectively, and unedited cells (UT), were determined over time by a p24 ELISA. (B) Challenge with X4 tropic HIV. Supernatants of unedited (UT) and TALEN® edited (CS) cells were infected with X4 tropic HIV (strain NL4-3) at MOIs of 0.01 and 0.001, respectively. Levels of p24 in the supernatants were determined over time by a p24 ELISA.

Table 1: gRNA CCR5 target sequences according to the invention

Table 2: polynucleotide and polypeptide sequences used in the examples

Table 3: on and off-target results in K562, CD4+ T-cells and CD34+ HSC

Table 4: Selection of genes that are upregulated over more than 24 hours upon T-cell activation.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology [Frederick M. AUSUBEL (2000) Wiley and son Inc, Library of Congress, USA; Molecular Cloning: A Laboratory Manual, Third Edition] [Sambrook et al (2001) Cold Spring Harbor, N.Y.: Cold Spring Harbor Laboratory Press]; Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. 1. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

The present invention is thus drawn to a general method of preparing primary hematopoietic cells capable to resist HIV involving gene targeted inhibition or inactivation of CCR5 expression.

By "hematopoietic cells" is meant any cells constitutive of the myeloid or lymphoid cell lineages including hematopoietic stem cells (HSC or HSPC) themselves. Hematopoietic stem cells (HSCs) reside in the bone marrow and have the unique ability to give rise to all of the different mature blood cell types and tissues. HSCs are self-renewing cells: when they proliferate, at least some of their daughter cells remain as HSCs, so that the pool of stem cells is not depleted. The others cells get differentiated into common lymphoid progenitor cells that produce lymphocytes and into common myeloid progenitor cells that produce monocytes. Lymphocytes are the cornerstone of the adaptive immune system. The lymphoid lineage is primarily composed of T-cells and B-cells.

HIV is the cause of the spectrum of disease known as HIV/AIDS. HIV is a retrovirus that primarily infects components of the human immune system such as CD4+ T-cells, macrophages and dendritic cells. It directly and indirectly destroys CD4+ T-cells. Ultimately, HIV causes AIDS by depleting CD4+ T-cells. This weakens the immune system and allows opportunistic infections. T-cells are indeed essential to the immune response and without them, the immune system cannot fight infections or kill cancerous cells. HIV can infect a variety of immune cells such as CD4+ T-cells, macrophages, and microglial cells. HIV entry to macrophages and CD4+ T-cells is mediated through interaction of the virion envelope glycoprotein gp120 and the chemokine receptor CCR5.

According to one aspect, the method of the invention includes producing HIV resistant primary cells by reducing the expression of CCR5 in T-cells by at least one of the steps of:
  i). Providing a population of primary cells originating from a patient or a donor;
  ii). Introducing into said primary cells a sequence specific reagent targeting at least one genomic sequence encoding the N-terminal hydrophilic external region of the CCR5 protein; and
  iii). Expressing said sequence specific reagent in said cells, so that the expression of functional CCR5 is reduced.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO—S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Primary cells are generally used in cell therapy as they are deemed more functional and less tumorigenic.

In general, primary immune cells are provided from donors or patients through a variety of methods known in the art, as for instance by leukapheresis techniques as reviewed by Schwartz J. et al. [Guidelines on the use of therapeutic apheresis in clinical practice-evidence-based approach from the Writing Committee of the American Society for Apheresis: the sixth special issue (2013) *J. Clin. Apher.* 28(3):145-284]. Stem and progenitor cells can be taken from the pelvis, at the iliac crest, using a needle or syringe. Alternatively, stem cells may be harvested from the circulating peripheral blood, while blood donors are injected with a cytokine, such as granulocyte-colony stimulating factor (G-CSF) that induces cells to leave the bone marrow and circulate in the blood vessels.

The primary cells are usually provided as populations of cells that may comprise different types of immune cells. In general, the population of primary T-cells according to the present invention comprises at least 50%, preferably at least 70%, and more preferably at least 90% of CD4+ T-cells. Populations of HSC generally comprise at least 50%, preferably at least 70%, and more preferably at least 90% of CD34+ cells The primary immune cells according to the present invention can also be differentiated from pluripotent stem cells, such as cord blood stem cells or induced pluripotent stem cells (iPS).

The method of the invention is preferably performed ex-vivo to obtain stably engineered primary cells which are subsequently engrafted into patients infected with HIV. The primary cells can originate from the patient himself (autologous approach) or from a donor (allogeneic approach).

So far, HSC have been more commonly used in allogeneic approaches than differentiated T-cells because there is a lower risk of graft versus host disease (GvHD) using HSCs than using T-cells. Moreover, HCSs can settle in the bone marrow and produce immune cells, such as CD4+ T-cells on a permanent basis, which, as per the present invention, will be CCR5 defective and thus made resistant to HIV on the long term.

According to the invention engineered primary T-cells can also be used along allogeneic approaches as well, especially when the expression of their T-Cell Receptor (TCR) is suppressed or reduced. In this regard, the applicant has already developed means to genetically inactivate TCR beta and/or alpha subunits using rare cutting endonucleases, to provide "universal" primary T-cells as described in Poirot et al. [Multiplex Genome-Edited T-cell Manufacturing Platform for "Off-the-Shelf" Adoptive T-cell Immunotherapies. *Cancer Res*. (2015) 75(18):3853-64]. The step of inhibiting TCR expression may thus be applied as a further step of the invention to obtain allogeneic HIV-resistant primary T-cells, preferably of genotype $[TCR]^{neg}[CCR5]^{neg}[CD4+]^{pos}$.

As shown herein, the inventors have obtained higher and more specific cleavage efficiency of CCR5 alleles by targeting sequences encoding the N-terminal hydrophilic external region of the CCR5 protein. This was in sharp contrast with the previous attempts targeting other sequences of CCR5.

Beside the better efficiency of the reagents, it seems advantageous to target the N-terminus part of CCR5 as this region is reported to be the main site for interactions with the HIV-1 gp120 envelop proteins following upon binding to CD4 [for review see in Zaitseva et al. (2003) Biochim BiophysActa. 11; 1614(1):51-61). According to a preferred embodiment of the method of the present invention, the sequence specific reagent used to reduce or prevent the expression of CCR5 targets a polynucleotide sequence comprised in the allelic sequence encoding the first 30 amino acids of CCR5, which corresponds to the 90 base pairs of its coding sequence from the start codon (SEQ ID NO:2).

By "sequence-specific reagent" is meant any active molecule that has the ability to specifically recognize a selected polynucleotide sequence from a genomic locus, preferably of at least 9 bp, more preferably of at least 10 bp and even more preferably of at least 12 pb in length, in view of modifying the expression of said genomic locus. According to a preferred aspect of the invention, said sequence-specific reagent that induces a stable mutation, is preferably a reagent that has nickase or endonuclease activity. According to another aspect, said sequence specific reagent can be a polynucleotide that hybridizes a transcript from said specific locus to inhibit its translation into a functional protein (e.g. RNAi). According to another aspect, said sequence specific reagent can be a polynucleotide that hybridizes a specific sequence of said genomic locus or transcript in conjunction with another molecule to form a complex, which alters the genomic locus or transcript or prevents its transcriptional/translational activity (e.g.: RNA guide+ Cas9/Cpf1).

In general, said sequence specific reagent that binds a genomic sequence encoding the N-terminal hydrophilic external region of the CCR5 human protein is comprised into a sequence that has at least 80%, preferably at least 90%, more preferably at least 95% identity with SEQ ID NO:3 and more specifically with SEQ ID NO:4.

According to a preferred embodiment of the invention, a mutation is precisely induced into the polynucleotide sequence encoding amino acids 1 to 20 of CCR5 (SEQ ID NO:3).

The sequence-specific reagent can be a chimeric polypeptide comprising a DNA binding domain and another domain displaying catalytic activity. Such catalytic activity can be for instance a nuclease to perform gene inactivation, methylase to perform gene silencing, nickase or double nickase to preferentially perform gene insertion by creating cohesive ends to facilitate gene integration by homologous recombination, or to perform base editing as described in Komor et al. (2016) Nature 19; 533(7603):420-4.

For instance, it can be a nuclease reagent that induces NHEJ or homologous recombination mechanisms, which has the advantage of introducing stable and inheritable mutations into CCR5 alleles, but can also be reagents preventing expression, transcription or translation of CCR5, such as RNAi or TALE-repressors. In general, the sequence specific reagents of the present invention have the ability to bind the above nucleic acid sequences having identity with SEQ ID NO:2, SEQ ID NO:3 or SEQ ID NO:4 or their corresponding reverse sequences.

By "nuclease reagent" is meant a nucleic acid molecule that contributes to an nuclease catalytic reaction in the target cell, preferably an endonuclease reaction, by itself or as a subunit of a complex such as a guide RNA/Cas9, preferably leading to the cleavage of a nucleic acid sequence target.

The nuclease reagents of the invention are generally "sequence-specific nuclease reagents", meaning that they can induce DNA cleavage in the cells at predetermined loci, referred to by extension as "targeted gene". The nucleic acid sequence which is recognized by the sequence specific reagents is referred to as "target sequence". Said target sequence is usually selected to be rare or unique in the cell's genome, and more extensively in the human genome, as can be determined using software and data available from human genome databases, such as www ensembl .org/index html. Such "target sequences" are preferably spanned by those having identity with SEQ ID NO:2, SEQ ID NO:3 or SEQ ID NO:4 as referred to before.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, said sequence specific reagent of the present invention is a nucleic acid encoding an "engineered" or "programmable" rare-cutting endonuclease, such as a homing endonuclease as described for instance by Arnould S., et al. (WO2004067736), a zing finger nuclease (ZFN) as described, for instance, by Urnov F., et al. [Highly efficient endogenous human gene correction using designed zinc-finger nucleases (2005) Nature 435:646-651], a TALE-Nuclease as described, for instance, by Mussolino et al. [A novel TALE nuclease scaffold enables high genome editing activity in combination with low toxicity (2011) Nucl. Acids Res. 39(21):9283-9293], or a MegaTAL nuclease as described, for instance by Boissel et al. [MegaTALs: a rare-cleaving nuclease architecture for therapeutic genome engineering (2013) Nucleic Acids Research 42 (4):2591-2601].

According to another embodiment, the endonuclease reagent is a RNA-guide to be used in conjunction with a RNA guided endonuclease, such as Cas9 or Cpf1, as per, inter alia, the teaching by Doudna, J. et al., [The new frontier of genome engineering with CRISPR-Cas9 (2014) Science 346 (6213):1077)] and Zetsche, B. et al. [Cpf1 Is a Single RNA-Guided Endonuclease of a Class 2 CRISPR-Cas System (2015) Cell 163(3): 759-771] the teaching of which is incorporated herein by reference.

Examples of RNA guides binding to SEQ ID NO:2, SEQ ID NO:3 or SEQ ID NO:4 as per the present invention are provided in Table 1.

TABLE 1 gRNA CCR5 target sequences according to the invention

| Name | Target sequence | SEQ ID # |
|---|---|---|
| CLS_CCR5gRNA1 | TGACATCAATTATTATACATCGG | SEQ ID NO: 12 |
| CLS_CCR5gRNA2 | TTTGCTTCACATTGATTTTTTGG | SEQ ID NO: 13 |
| CLS_CCR5gRNA3 | CTTCACATTGATTTTTTGGCAGG | SEQ ID NO: 14 |
| CLS_CCR5gRNA4 | TTCACATTGATTTTTTGGCAGGG | SEQ ID NO: 15 |
| CLS_CCR5gRNA5 | TAATAATTGATGTCATAGATTGG | SEQ ID NO: 16 |

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins).

In general, 80% of the endonuclease reagent is degraded by 30 hours, preferably by 24, more preferably by 20 hours after transfection.

An endonuclease under mRNA form is preferably synthetized with a cap to enhance its stability according to techniques well known in the art, as described, for instance, by Kore A. L., et al. (Locked nucleic acid (LNA)-modified dinucleotide mRNA cap analogue: synthesis, enzymatic incorporation, and utilization (2009) J Am Chem Soc. 131 (18):6364-5).

In general, electroporation steps that are used to transfect immune cells are typically performed in closed chambers comprising parallel plate electrodes producing a pulse electric field between said parallel plate electrodes greater than 100 volts/cm and less than 5,000 volts/cm, substantially uniform throughout the treatment volume such as described in WO/2004/083379, which is incorporated by reference, especially from page 23, line 25 to page 29, line 11. One such electroporation chamber preferably has a geometric factor ($cm^{-1}$) defined by the quotient of the electrode gap squared (cm2) divided by the chamber volume ($cm^3$), wherein the geometric factor is less than or equal to 0.1 $cm^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

It has been observed that, according to the invention, culturing the cells at a lower temperature comprised between 25° C. and 37° C., preferably between 30 and 35° C., for more than 24 hours post transfection could enhance the endonuclease activity of the sequence-specific reagents introduced into the cells, especially when transfection is by electroporation of mRNA. A non-binding hypothesis would be that the transcripts would be degraded more slowly at lower temperature and thus would be better expressed into the cells during that step.

Due to their higher specificity, TALE-nuclease have proven to be particularly appropriate sequence specific nuclease reagents for therapeutic applications, especially under heterodimeric forms—i.e. working by pairs with a "right" monomer (also referred to as "5'" or "forward") and "left" monomer (also referred to as "3'" or "reverse") as reported for instance by Mussolino et al. [TALEN® facilitate targeted genome editing in human cells with high specificity and low cytotoxicity (2014) *Nucl. Acids Res.* 42(10): 6762-6773].

As previously stated, the sequence specific reagent is preferably under the form of nucleic acids, such as under DNA or RNA form encoding a rare cutting endonuclease a subunit thereof, but they can also be part of conjugates involving polynucleotide(s) and polypeptide(s) such as so-called "ribonucleoproteins". Such conjugates can be formed with reagents as Cas9 or Cpf1 (RNA-guided endonucleases), which involve RNA guides that can be complexed with their respective nucleases. Conjugates involving polynucleotide(s) and polypeptide(s) such as "ribonucleoproteins" can be packages into nanoparticles that can be used as transfection vectors ex-vivo or in-vivo.

Preferred nanoparticles according to the invention are coated with ligands, such as antibodies, having a specific affinity towards HSC surface proteins, such as CD105 (Uniprot #P17813). Preferred nanoparticles are biodegradable polymeric nanoparticles in which the sequence specific reagents under polynucleotide form are complexed with a polymer of polybeta amino ester and coated with polyglutamic acid (PGA).

According to one aspect of the invention, the hematopoietic stem cells are made resistant to HIV directly into the patient's body by in-vivo transfection of a CCR5 sequence specific reagent according to the present invention, preferably packaged into nanoparticles. The nanoparticles can be also coated with a ligand of CCR5, such as gp120, to drive the sequence specific reagent into the CCR5 positive cells.

As another aspect of the present invention, the CCR5 sequence specific reagent according to the invention is packaged into a viral particle, preferably a lentivirus particle displaying gp120 at its surface, as a mock HIV, which will introduce the CCR5 sequence specific reagent into CCR5 positive hematopoietic cells. Upon entry through CCR5, the expression of CCR5 can be inactivated or reduced so that the cell is locked to a subsequent HIV infection.

In particular, the present invention provides using lentiviral vector derived from HIV strains BalR5, which are CCR5 tropic, such as the Bal tp R5 vector shown in FIG. 3D, as specific vehicles for the delivery of CCR5 sequence-specific reagents into T-cells, preferably for the delivery of endonuclease reagents. Such lentiviral vectors are preferably characterized in that the sequence encoding the CCR5 sequence specific reagent is introduced into the genome of a HIV Bal R5 strain, which has generally been made non-replicative. [Schweighardt B, et al. (2004) R5 Human Immunodeficiency Virus Type 1 (HIV-1) Replicates More Efficiently in Primary CD4+ T-Cell Cultures Than X4 HIV-1. *Journal of Virology.* 78(17):9164-9173].

In the practice of the present invention, a pair of heterodimeric TALE-nuclease polypeptides T3 presented in Table 2 has unexpectedly shown higher specificity and efficiency towards inactivation of CCR5 alleles in primary CD34+ or CD4+ cells. The TALE-nuclease monomers are designed for providing cleavage within the preferred spacer sequence of SEQ ID NO:7.

According to certain embodiments, the present invention provides a pair of TALE-nuclease monomers having respectively a polypeptide sequence sharing at least 80%, preferably at least 85%, more preferably at least 90%, and most preferably at least 95% identity with SEQ ID NO:8 and SEQ ID NO:9.

The present application is more particularly drawn to said preferred monomers of dimeric TALEN polypeptides, as individual products or in combination. The polypeptide monomers preferably comprise respectively from 10 to 15 of the following variable di-residues (RVDs):

```
Left monomer CCR5 TALE-nuclease:
NI, NG, HD, NI, NI, NN, NG, NN, NG, HD, NI, NI,
NN, NG, HD Right monomer CCR5 TALE-nuclease:
HD, HD, NN, NI, NG, NN, NG, NI, NG, NI, NI, NG,
NI, NI, NG
```

These monomers are designed to bind their respective target polynucleotide sequences SEQ ID NO:5 and SEQ ID NO:6. The CCR5 endogenous sequence located between the target sequences is referred to as being the "spacer sequence", where cleavage occurs.

The preferred monomers of TAL nucleases according to the invention can comprise the optional features of comprising shorter C-terminal and N-terminal regions (extending their DNA binding domain), than the wild type AvrBs3 TALE protein. In a preferred embodiment, only the last 160 residues and preferably less (e.g.: N152 truncation) of the N-terminus of AvrBs3 are conserved. Meanwhile, only the first 60 residues and preferably less (e.g. C40 truncation) of the AvrBs3 TALE protein are conserved.

The present invention can also be defined as a method for producing hematopoietic primary cells by inducing cleavage into SEQ ID NO:7 of an allele encoding CCR5 using a rare-cutting endonuclease.

The invention is also drawn to the polynucleotides and vectors encoding the above referred CCR5 sequence specific reagents, which are preferably the preferred monomers of dimeric TALE-nuclease described above. The invention also extend to the RNA guides that can bind the target sequences listed in Table 1 to obtain cleavage of SEQ ID NO:2, preferably SEQ ID NO:3, more preferably SEQ ID NO:4 and even more preferably SEQ ID NO:7 when expressing or introducing or concomitantly into the cell a RNA guided endonuclease, such as Cas9 or Cpf1.

As a result of the present invention, the expression of CCR5 in T-cells or in HSC, as can be measured by deep sequencing, transcription analysis (PCR reverse) or immunostaining (immunoblot), is reduced by more than 50%, preferably more than 60%, more preferably more than 70%, and even more preferably more than 80%, in the resulting population of primary cells. According to a preferred aspect, a mutation is introduced into at least 50%, more preferably into at least 65%, and even more preferably at least 75%, of the CCR5 alleles present in the population of treated cells (% before any sorting or purification steps).

Expressing chimeric antigen receptors (CAR) in CCR5 deficient immune cells Expressing chimeric antigen receptors (CAR) have become the state of the art to direct or improve the specificity of primary immune cells, such as T-Cells and NK-cells towards tumors or infected cells. CARs expressed by these immune cells specifically target antigen markers at the surface of the pathological cells, which further help said immune cells to destroy these cells in-vivo [Sadelain M. et al. "The basic principles of chimeric antigen receptor design" (2013) Cancer Discov. 3(4):388-98]. CARs are usually designed to comprise activation domains that stimulate immune cells in response to binding to a specific antigen (so-called positive CAR), but they may also comprise an inhibitory domain with the opposite effect (so-called negative CAR) [Fedorov, V. D. (2014) "Novel Approaches to Enhance the Specificity and Safety of Engineered T Cells" Cancer Journal 20 (2):160-165]. Positive and negative CARs may be combined or co-expressed to finely tune the cells immune specificity depending of the various antigens present at the surface of the target cells.

The genetic sequences encoding CARs are generally introduced into the cells genome using retroviral vectors that have elevated transduction efficiency but integrate at random locations. As an alternative, components of chimeric antigen receptor (CAR) car be introduced at selected loci by targeted gene recombination, more particularly at selected endogenous loci under control of endogenous promoters.

According to one aspect of the present invention, chimeric antigen receptors (CAR) can be expressed into the primary hematopoietic cells, in which the expression of CCR5 has been reduced or inactivated as previously described. The polynucleotide sequences encoding said CARs can be inserted at the CCR5 locus using the sequence specific reagents of the present invention or at loci other than CCR5. The CARs can be selected to improve the affinity of CCR5 defective T-cells towards HIV infected cells or towards infected or malignant cells.

It is therefore an object of the present invention to provide CCR5 defective primary immune cells resistant to HIV obtainable by the method described herein, endowed with a CAR targeting infected or malignant cells.

CAR specifically directed against HIV infected cells has been described for instance in WO1995021528 or in US2017/0044240.

As a preferred embodiment of the present invention, the CCR5 defective cell is endowed with a CAR directed against CCR5, so as to eliminate all T-cells still expressing CCR5 from the patient.

According to another preferred embodiment, the CCR5 defective cell is endowed with a CAR directed against the surface protein FcγRlla that has been found to be present on CD4+ T-cell infected with HIV (reservoir T-cells) [Forthal, D. et al. (2007) FcγRlla Genotype Predicts Progression of HIV Infection. J. Immunol. 179(11):7916-7923].

According to another preferred embodiment, the CCR5 defective cell is endowed with a CAR directed against at least one epitope of the surface protein gp120 which is characteristic of CD4+ T-cell infected with HIV.

According to another preferred embodiment, the CCR5 defective cell is endowed with a CAR directed against at least one epitope of the surface protein CD32a which is characteristic of quiescent CD4+ T-cell infected with HIV [Descours et al. (2017), CD32a is a marker of a CD4 T-cell HIV reservoir harbouring replication-competent proviruses. Nature. 543:564-567].

According to one aspect, HIV resistant cells endowed with CARs specifically directed against cancer markers can be used for treating patients having both cancer and HIV. More specifically, CCR5 defective cells of the present invention endowed with CAR anti-CD19 can be used for treating patients with HIV and AML. An example of CAR anti-CD19 is described in WO2014184143.

CCR5 defective cells of the present invention endowed with CAR anti-CD22 can be used for treating patients with HIV and AML. An example of CAR anti-CD22 is described in WO2013059593.

CCR5 defective cells of the present invention endowed with CAR anti-CD123 can be used for treating Patients with HIV and BPDCN or with HIV and AML. An example of CAR anti-CD123 is described in WO2015140268.

CCR5 defective cells of the present invention endowed with CAR anti-CS1 can be used for treating patients with HIV and MM (multiple myeloma). An example of CAR anti-CS1 is described in WO2014179759.

Such therapy would have several advantages including preventing AIDS during immunotherapy cancer treatments. Production of HIV Resistant Immune Cells Through CCR5 Mutated Hematopoietic Stem Cells (HSCs)

One aspect of the present invention more particularly concerns the genetic modification of hematopoietic stem cells (HSCs) in such a way that they can produce, preferably continuously, in-vivo HIV-resistant immune cells, especially CCR5 defective T-cells.

CCR5 alleles can be mutated by expressing the CCR5 sequence specific reagent of the present invention directly in vivo into HIV patient's HSCs by using appropriate vectors, such as nanoparticles, which can be injected in the blood stream, or more commonly by extracting and treating the HSCs ex-vivo from the patient itself of from donors.

HSCs are commonly harvested from the peripheral blood after mobilization (patients receive recombinant human granulocyte-colony stimulating factor (G-CSF)). The patient's peripheral blood is collected and enriched for HSCs using the CD34+ marker. HSCs are then cultured ex vivo and exposed to viral vectors. The ex vivo culture period varies from 1 to 4 days. Prior to the infusion of gene-edited HSCs, patients may be treated with chemotherapy agents or irradiation to help enhance the engraftment efficiency. Gene-edited HSCs are re-infused into the patient intravenously. The cells migrate into the bone marrow before finally residing in the sinusoids and perivascular tissue. Both homing and hematopoiesis are integral aspects of engraftment. Cells that have reached the stem cell niche through homing will begin producing mature myeloid and lymphoid cells from each blood lineage. Hematopoiesis continues through the action of long-term HSCs, which are capable of self-renewal for life-long generation of the patient's mature blood cells, in particular the production of common lymphoid progenitor cells, such as T cells and NK cells, which are key immune cells for eliminating infected and malignant cells.

The present invention provides with performing gene inactivation of CCR5 in HSCs, and optionally, targeted gene insertion to introduce exogenous coding sequences under the control of endogenous or exogenous promoters. As developed further on, the exogenous coding sequences or transgenes can enhance the therapeutic potential of the immune cells, such as their persistence, activation, life span, resistance to drugs, cytotoxicity, in different ways. The exogenous sequences can also express chimeric antigen receptors or modified TCRs to enhance their affinity to specific cell types.

The HSCs can be transduced with a polynucleotide vector (donor template), such as an AAV vector, during an ex-vivo treatment as referred to in the previous paragraph, whereas a sequence specific nuclease reagent is expressed as to promote the insertion of the coding sequences at the selected locus. The resulting engineered HSCs can be then engrafted into a patient in need thereof for a long term in-vivo production of engineered immune cells that will comprise said exogenous coding sequences.

Depending on the activity of the selected endogenous promoter, the coding sequences will be selectively expressed in certain lineages or in response to the local environment of the immune cells in-vivo, thereby providing adoptive immunotherapy.

Endogenous promoters, which are specifically activated into NK and T-cells, especially during T-cell activation are particularly appropriate for the expression of the inserted exogenous sequence because HSC also produce other types of hematopoietic differentiated cells into which expression of the exogenous sequences could have undesirable and unexpected consequences. Table 4 lists a selection of promoters that are strongly induced upon T-cell activation.

The invention comprises as a preferred aspect the introduction of an exogenous sequence encoding a CAR, or a component thereof, into HSCs, preferably under the transcriptional control of a promoter of a gene that is not expressed in HSC, more preferably a gene that is only expressed in the hematopoietic cells produced by said HSC, and even more preferably of a gene that is only expressed in T-cells or NK cells.

Conditional CAR Expression in HSCs to Overpass the Thymus Barrier

A preferred aspect of the present invention concerns the in-vivo production by the above engineered HSCs of hematopoietic immune cells, such as T-cells or NK-cells, expressing exogenous coding sequences, in particular a CAR or a component thereof.

One major bar of the production of hematopoietic CAR positive cells by engineered HSCs, for instance, is the rejection of the CAR positive cells by the immune system itself, especially by the thymus.

The blood-thymus barrier regulates exchange of substances between the circulatory system and thymus, providing a sequestered environment for immature T cells to develop. The barrier also prevents the immature T cells from contacting foreign antigens (since contact with antigens at this stage will cause the T cells to die by apoptosis).

One solution provided by the present invention is to place the sequences encoding the CAR components in the HSCs under the transcriptional control of promoters which are not significantly transcribed into the hematopoietic cells when they pass through the thymus barrier. One example of a gene that offers a conditional expression of the CAR into the hematopoietic cells with reduced or no significant transcriptional activity in the thymus is LCK (Uniprot: P06239).

According to a preferred aspect of the invention the exogenous sequence encoding a CAR, or a component thereof, is introduced into the HSC under the transcriptional control of a gene that is described as being specifically expressed in T-cells or NK cells, preferably in these types of cells only.

The invention thereby provides with a method of producing HSCs comprising an exogenous coding sequences to be expressed exclusively in selected hematopoietic lineage(s), said coding sequences encoding preferably at least one component of a CAR or of an antigen in order to stimulate the immune system.

More broadly, the invention provides with a method of engineering HSCs by gene targeted insertion of an exogenous coding sequences to be selectively expressed in the hematopoietic cells produced by said HSCs. As a preferred embodiment, said hematopoietic cells produced by said engineered HSCs express said exogenous coding sequences in response to selected environmental factors or in-vivo stimuli to improve their therapeutic potential.

Improving the Therapeutic Potential of HIV Resistant Immune Cells by Gene Targeted Integration at the CCR5 Locus or at Locus Having T-Cell Dependent Transcriptional Activity According to one aspect of the present invention, the mutation introduced into the sequence encoding the N-terminal hydrophilic external region of the CCR5 as per the method previously described gives rise to, or results from, a targeted gene insertion.

By "targeted gene insertion" is meant that an exogenous polynucleotide coding sequence is introduced into an endogenous gene, such as CCR5, at a specified locus. Here, the sequence specific nuclease reagent used according to the invention, which specifically cleaves CCR5 can also be used to induce the integration of an exogenous template at the locus of SEQ ID NO:2, preferably SEQ ID NO:3 or SEQ ID NO:4. Said exogenous sequence can encode various polypeptides, such as a protein conferring resistance or sensitivity to a drug or useful as a selectable marker or receptor.

"Exogenous sequence" refers to any nucleotide or nucleic acid sequence that was not initially present at the selected locus. This sequence may be homologous to, or a copy of, a genomic sequence, or be a foreign sequence introduced into the cell. By opposition "endogenous sequence" means a cell genomic sequence initially present at a locus. The exogenous sequence preferably codes for a polypeptide which expression confers a therapeutic advantage over sister cells that have not integrated this exogenous sequence at the locus. An endogenous sequence that is gene edited by the insertion of a nucleotide or polynucleotide as per the method of the present invention, in order to express a different polypeptide is broadly referred to as an exogenous coding sequence.

For instance, said targeted gene insertion can comprise an exogenous sequence encoding a protein which expression contributes to inhibiting CXCR4 pathway, which would confer broader spectrum of HIV resistance.

According to one aspect of the invention, said targeted gene insertion comprises an exogenous sequence encoding a chimeric antigen receptor (CAR), such as a CAR targeting an HIV epitope or cancer marker antigens previously mentioned.

According to another aspect of the invention, said targeted insertion comprises an exogenous sequence encoding siRNA, shRNA or miRNA, directed against the expression of viral or endogenous genes involved into HIV propagation, such as nef, vpr, vif, and vpu accessory genes of HIV-1 as described for instance by Vlachakis D. et al. [Antiviral Stratagems Against HIV-1 Using RNA Interference (RNAi) Technology (2013) *Evol Bioinform Online.* 9: 203-213]

More examples of gene insertion are provided with the following embodiments:

Conferring Hematopoietic Cells Resistance to Drugs or Immune Depletion Agents

According to one aspect of the present method, the exogenous sequence that is integrated into the primary hematopoietic cells genomic locus encodes a molecule that confers resistance of said hematopoietic cells or progeny thereof to a drug.

Examples of preferred exogenous sequences are variants of dihydrofolate reductase (DHFR) conferring resistance to folate analogs such as methotrexate, variants of inosine monophosphate dehydrogenase 2 (IMPDH2) conferring resistance to IMPDH inhibitors such as mycophenolic acid (MPA) or its prodrug mycophenolate mofetil (MMF), variants of calcineurin or methylguanine transferase (MGMT) conferring resistance to calcineurin inhibitor such as FK506 and/or CsA, variants of mTOR such as mTORmut conferring resistance to rapamycin and variants of Lck, such as Lckmut conferring resistance to Imatinib and Gleevec.

The term "drug" is used herein as referring to a compound or a derivative thereof, preferably a standard chemotherapy agent that is generally used for interacting with a cancer cell, thereby reducing the proliferative or living status of the cell. Examples of chemotherapeutic agents include, but are not limited to, alkylating agents (e.g., cyclophosphamide, ifosamide), metabolic antagonists (e.g., purine nucleoside antimetabolite such as clofarabine, fludarabine or 2'-deoxyadenosine, methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents TRIMETHOTRIXATE™ (TMTX), TEMOZOLOMIDE™ RALTRITREXED™, S-(4-Nitrobenzyl)-6-thioinosine (NBMPR), 6-benzyguanidine (6-BG), bis-chloronitrosourea (BCNU) and CAMPTOTHECIN™, or a therapeutic derivative of any thereof.

As used herein, an immune cell is made "resistant or tolerant" to a drug when said cell, or population of cells is modified so that it can proliferate, at least in-vitro, in a culture medium containing half maximal inhibitory concentration (IC50) of said drug (said IC50 being determined with respect to an unmodified cell(s) or population of cells).

In a particular embodiment, said drug resistance can be conferred to the immune cells by the expression of at least one "drug resistance coding sequence". Said drug resistance coding sequence refers to a nucleic acid sequence that confers "resistance" to an agent, such as one of the chemotherapeutic agents referred to above. A drug resistance coding sequence of the invention can encode resistance to anti-metabolite, methotrexate, vinblastine, cisplatin, alkylating agents, anthracyclines, cytotoxic antibiotics, anti-immunophilins, their analogs or derivatives, and the like (Takebe, N., S. C. Zhao, et al. (2001) "Generation of dual resistance to 4-hydroperoxycyclophosphamide and methotrexate by retroviral transfer of the human aldehyde dehydrogenase class 1 gene and a mutated dihydrofolate reductase gene". Mol. Ther. 3(1): 88-96), (Zielske, S. P., J. S. Reese, et al. (2003) "In vivo selection of MGMT(P140K) lentivirus-transduced human NOD/SCID repopulating cells without pretransplant irradiation conditioning." J. Clin. Invest. 112 (10): 1561-70) (Nivens, M. C., T. Felder, et al. (2004) "Engineered resistance to camptothecin and antifolates by retroviral coexpression of tyrosyl DNA phosphodiesterase-I and thymidylate synthase" Cancer Chemother Pharmacol 53(2): 107-15), (Bardenheuer, W., K. Lehmberg, et al. (2005). "Resistance to cytarabine and gemcitabine and in vitro selection of transduced cells after retroviral expression of cytidine deaminase in human hematopoietic progenitor cells". Leukemia 19(12): 2281-8), (Kushman, M. E., S. L. Kabler, et al. (2007) "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1" Carcinogenesis 28(1): 207-14).

The expression of such drug resistance exogenous sequences in the primary hematopoietic cell as per the present invention more particularly allows the use of said immune cells in cell therapy treatment schemes where cell therapy is combined with chemotherapy or into patients previously treated with these drugs.

Several drug resistance coding sequences have been identified that can potentially be used to confer drug resistance according to the invention. One example of drug resistance coding sequence can be for instance a mutant or modified form of Dihydrofolate reductase (DHFR). DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by antifolates used in therapy have been described. In a particular embodiment, the drug resistance coding sequence according to the present invention can be a nucleic acid sequence encoding a mutant form of human wild type DHFR (GenBank: AAH71996.1), which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 (Schweitzer et al. (1990) "Dihydrofolate reductase as a therapeutic target" Faseb J 4(8): 2441-52; International application WO94/24277; and U.S. Pat. No. 6,642,043). In a particular embodiment, said DHFR mutant form comprises two mutated amino acids at position L22 and F31. Correspondence of amino acid positions described herein is frequently expressed in terms of the positions of the amino acids of the form of wild-type DHFR polypeptide. In a particular embodiment, the serine residue at position 15 is preferably replaced with a tryptophan residue. In another particular embodiment, the leucine residue at position 22 is preferably replaced with an amino acid which will disrupt binding of the mutant DHFR to antifolates, preferably with uncharged amino acid residues such as phenylalanine or tyrosine. In another particular embodiment, the phenylalanine residue at positions 31 or 34 is preferably replaced with a small hydrophilic amino acid such as alanine, serine or glycine.

Another example of drug resistance coding sequence can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (Genebank: NP_000875.2) leading to a significantly increased resistance to IMPDH inhibitor. Mutations in these variants are preferably at positions T333 and/or S351 (Yam, P., M. Jensen, et al. (2006) "Ex vivo selection and expansion of cells based on expression of a mutated inosine monophosphate dehydrogenase 2 after HIV vector transduction: effects on lymphocytes, monocytes, and CD34+ stem cells" Mol. Ther. 14(2): 236-44)(Jonnalagadda, M., et al. (2013) "Engineering human T cells for resistance to methotrexate and mycophenolate mofetil as an in vivo cell selection strategy." PLoS One 8(6): e65519).

Another drug resistance coding sequence is the mutant form of calcineurin. Calcineurin (PP2B-NCBI: ACX34092.1) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin et al. (2009) "Generation of EBV-specific cytotoxic T cells that are resistant to calcineurin inhibitors for the treatment of post-transplantation lymphoproliferative disease" Blood 114(23): 4792-803). In a particular embodiment, said mutant form can comprise at least one mutated amino acid of the wild type calcineurin heterodimer at positions: V314, Y341, M347, T351, W352, L354, K360, preferably double mutations at positions T351 and L354 or V314 and Y341. In a particular embodiment, the valine residue at position 341 can be replaced with a lysine or an arginine residue, the tyrosine residue at position 341 can be replaced with a phenylalanine residue; the methionine at position 347 can be replaced with the glutamic acid, arginine or tryptophane residue; the threonine at position 351 can be replaced with the glutamic acid residue; the tryptophane residue at position 352 can be replaced with a cysteine, glutamic acid or alanine residue, the serine at position 353 can be replaced with the histidine or asparagines residue, the leucine at position 354 can be replaced with an alanine residue; the lysine at position 360 can be replaced with an alanine or phenylalanine residue. In another particular embodiment, said mutant form can comprise at least one mutated amino acid of the wild type calcineurin heterodimer b at positions: V120, N123, L124 or K125, preferably double mutations at positions L124 and K125. In a particular embodiment, the valine at position 120 can be replaced with a serine, an aspartic acid, phenylalanine or leucine residue; the asparagine at position 123 can be replaced with a tryptophan, lysine, phenylalanine, arginine, histidine or serine; the leucine at position 124 can be replaced with a threonine residue; the lysine at position 125 can be replaced with an alanine, a glutamic acid, tryptophan, or two residues such as leucine-arginine or isoleucine-glutamic acid can be added after the lysine at position 125 in the amino acid sequence. Correspondence of amino acid positions described herein is frequently expressed in terms of the positions of the amino acids of the form of wild-type human calcineurin heterodimer b polypeptide (NCBI: ACX34095.1).

Another drug resistance coding sequence is 0(6)-methylguanine methyltransferase (MGMT-UniProtKB: P16455) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, R. et al. (1999) "Retroviral-mediated expression of the P140A, but not P140A/G156A, mutant form of 06-methylguanine DNA methyltransferase protects hematopoietic cells against 06-benzylguanine sensitization to chloroethylnitrosourea treatment" J. Pharmacol. Exp. Ther. 290(3): 1467-74). In a particular embodiment, AGT mutant form can comprise a mutated amino acid of the wild type AGT position P140. In a preferred embodiment, said proline at position 140 is replaced with a lysine residue.

Another drug resistance coding sequence can be multidrug resistance protein (MDR1) gene. This gene encodes a membrane glycoprotein, known as P-glycoprotein (P-GP) involved in the transport of metabolic byproducts across the cell membrane. The P-GP protein displays broad specificity towards several structurally unrelated chemotherapy agents. Thus, drug resistance can be conferred to cells by the expression of nucleic acid sequence that encodes MDR-1 (Genebank NP_000918).

Another drug resistance coding sequence can contribute to the production of cytotoxic antibiotics, such as those from ble or mcrA genes. Ectopic expression of ble gene or mcrA in an immune cell gives a selective advantage when exposed to the respective chemotherapeutic agents bleomycine and mitomycin C (Belcourt, M. F. (1999) "Mitomycin resistance in mammalian cells expressing the bacterial mitomycin C resistance protein MCRA". PNAS. 96(18):10489-94).

Another drug resistance coding sequence can come from genes encoded mutated version of drug targets, such as mutated variants of mTOR (mTOR mut) conferring resistance to rapamycin such as described by Lorenz M. C. et al. (1995) "TOR Mutations Confer Rapamycin Resistance by Preventing Interaction with FKBP12-Rapamycin" The Journal of Biological Chemistry 270, 27531-27537, or certain mutated variants of Lck (Lckmut) conferring resistance to Gleevec as described by Lee K. C. et al. (2010) "Lck is a key target of imatinib and dasatinib in T-cell activation", Leukemia, 24: 896-900.

As described above, the genetic modification step of the method can comprise a step of introduction into cells of an exogenous nucleic acid comprising at least a sequence encoding the drug resistance coding sequence and a portion of an endogenous gene such that homologous recombination occurs between the endogenous gene and the exogenous nucleic acid. In a particular embodiment, said endogenous gene can be the wild type "drug resistance" gene, such that after homologous recombination, the wild type gene is replaced by the mutant form of the gene which confers resistance to the drug.

Enhancing the Therapeutic Activity of Immune Cells

According to one aspect of the present method, the exogenous sequence that is integrated into the immune cells genomic locus encodes a molecule that enhances the therapeutic activity of the immune cells.

By "enhancing the therapeutic activity" is meant that the immune cells, or population of cells, engineered according to the present invention, become more aggressive than non-engineered cells or population of cells with respect to a selected type of target cells. Said target cells consists of a defined type of cells, or population of cells, preferably characterized by common surface marker(s). In the present specification, "therapeutic potential" reflects the therapeutic activity, as measured through in-vitro experiments. In general, sensitive cancer cell lines, such as Daudi cells, are used to assess whether the immune cells are more or less active towards said cells by performing cell lysis or growth reduction measurements. This can also be assessed by measuring levels of degranulation of immune cells or chemokines and cytokines production. Experiments can also be performed in mice with injection of tumor cells, and by monitoring the resulting tumor expansion. Enhancement of activity is deemed significant when the number of developing cells in these experiments is reduced by the immune cells by more than 10%, preferably more than 20%, more preferably more than 30%, even more preferably by more than 50%.

According to one aspect of the invention, said exogenous sequence encodes a chemokine or a cytokine, such as IL-12. It is particularly advantageous to express IL-12 as this cytokine is extensively referred to in the literature as promoting immune cell activation (Colombo M. P. et al. (2002) "Interleukin-12 in anti-tumor immunity and immunotherapy" *Cytokine Growth Factor Rev.* 13(2):155-68).

According to a preferred aspect of the invention the exogenous coding sequence encodes or promotes secreted factors that act on other populations of immune cells, such as T-regulatory cells, to alleviate their inhibitory effect on said immune cells.

According to one aspect of the invention, said exogenous sequence encodes an inhibitor of regulatory T-cell activity is a polypeptide inhibitor of forkhead/winged helix transcription factor 3 (FoxP3), and more preferably is a cell-penetrating peptide inhibitor of FoxP3, such as that referred as P60 (Casares N. et al. (2010) "A peptide inhibitor of FoxP3 impairs regulatory T cell activity and improves vaccine efficacy in mice." *J Immunol* 185(9):5150-9).

By "inhibitor of regulatory T-cells activity" is meant a molecule or precursor of said molecule secreted by the T-cells and which allow T-cells to escape the down regulation activity exercised by the regulatory T-cells thereon. In general, such inhibitor of regulatory T-cell activity has the effect of reducing FoxP3 transcriptional activity in said cells.

Enhancing Specificity and Safety of Immune Cells

According to one aspect, while a positive CAR is introduced into the immune cell by a viral vector, a negative CAR can be introduced by targeted gene insertion and vice-versa, and be active preferably only during immune cells activation. Accordingly, the inhibitory (i.e. negative) CAR contributes to an improved specificity by preventing the immune cells to attack a given cell type that needs to be preserved. Still according to this aspect, said negative CAR can be an apoptosis CAR, meaning that said CAR comprise an apoptosis domain, such as FasL (CD95-NCBI: NP_000034.1) or a functional variant thereof, that transduces a signal inducing cell death (Eberstadt M; et al. "NMR structure and mutagenesis of the FADD (Mort1) death-effector domain" (1998) *Nature.* 392 (6679): 941-5).

Accordingly, the exogenous coding sequence inserted according to the invention can encode a factor that has the capability to induce cell death, directly, in combination with, or by activating other compound(s).

As another way to enhance the safety of the primary immune cells, the exogenous coding sequence can encodes molecules that confer sensitivity of the immune cells to drugs or other exogenous substrates. Such molecules can be cytochrome(s), such as from the P450 family (Preissner S et al. (2010) "SuperCYP: a comprehensive database on Cytochrome P450 enzymes including a tool for analysis of CYP-drug interactions". *Nucleic Acids Res* 38 (Database issue): D237-43), such as CYP2D6-1 (NCBI-NP_000097.3), CYP2D6-2 (NCBI-NP_001020332.2), CYP2C9 ( ) CYP3A4 (NCBI-NP_000762.2), CYP2C19 (NCBI-NP_000760.1) or CYP1A2 (NCBI-NP_000752.2.), conferring hypersensitivity of the immune cells to a drug, such as cyclophosphamide and/or isophosphamide.

Further Gene Editing CCR5 Defective Primary Hematopoietic Cells

According to a further aspect, further alleles are inactivated in the primary hematopoietic cells of the present invention, in addition to, or in combination with CCR5, in view of improving the therapeutic potential of said engineered cells. Here below are presented endogenous gene, which expression is reduced in combination with that of CCR5 and the advantages associated with such combination.

CCR5 is implicated in susceptibility to HIV infection and disease, and acts as a primary co-receptor for HIV. However, CCR5 is not the only member of the CCR family that can facilitate HIV entry and infection. It has structural similarities to other proteins of the CCR family in structure and in ligand binding, in which the similar ligand binding can be due to conserved structural domains in the family. As such, CCR2b, CCR3, and CCR8 can be also utilized by some HIV strains as co-receptors for viral entry. Thus, the invention can comprise an additional step of reducing or preventing the expression of the genes encoding these proteins, in order to make the immune cells even more resistant to HIV.

As another embodiment, the expression of genes involved into self and non-self recognition can be reduced or suppressed in order to prevent graft versus host disease (GVHD) reaction or immune rejection when introducing the allogeneic CCR5 deficient cells into a recipient patient. This approach is particularly relevant with allogeneic T-cells, which possess T-cells receptor (TCR) that are prompt to activate their immune activity against the recipient hosts cells. To reduce the alloreactivity of the allogeneic T-cells, the method provides an optional step of reducing, preventing or modifying the expression of genes encoding TCR, such as the genes encoding TCR-alpha or TCR-beta subunits. This can be performed by using sequence specific reagents such as TALE-nucleases as described for instance in WO2013176915 or by expressing recombinant TCR into the primary cells as described in WO2014160030.

As another embodiment, one gene editing step can be performed to reduce or prevent the expression of the B2m protein and/or another protein involved in its regulation such as C2TA (Uniprot P33076) or in MHC recognition, such as HLA proteins. This, like the previous TCR modification, permits the engineered primary immune cells originating from donors or the immune cells produced by the engineered HSC originating from donors, to be less alloreactive when infused into patients.

Examples follow of further loci that may be edited in view of improving the activity, the persistence and the therapeutic activity of the engineered primary cells:

Inducing Resistance to Chemotherapy Drugs

According to another embodiment, the present method may include a gene edited step to reduce or prevent the expression of a gene responsible for the sensitivity of the immune cells to compounds used in standard of care treatments for cancer or infection, such as drugs purine nucleotide analogs (PNA) or 6-Mercaptopurine (6MP) and 6 thio-guanine (6TG) commonly used in chemotherapy. Reducing or inactivating the genes involved into the mode of action of such compounds (referred to as "drug sensitizing genes") improves the resistance of the immune cells to same.

Examples of drug sensitizing gene are those encoding DCK (Uniprot P27707) with respect to the activity of PNA, such a clorofarabine et fludarabine, HPRT (Uniprot P00492) with respect to the activity of purine antimetabolites such as 6MP and 6TG, and GGH (Uniprot Q92820) with respect to the activity of antifolate drugs, in particular methotrexate.

This enables the cells to be used after or in combination with conventional anti-cancer chemotherapies.

Resistance to Immune-Suppressive Treatments

According to another embodiment, the present method may comprise a gene editing step to reduce or prevent the expression of receptors or proteins, which are known drug targets, making said cells resistant to said drugs. Such target can be glucocorticoids receptors or antigens for antibodies used in immune-depletion drug treatments. For example, the engineered immune cells can be made resistant to glucocorticoids or to therapeutic antibodies, such as Alemtuzumab, an antibody commonly used to deplete CD52 positive immune cells in various blood cancers.

Also, the method of the invention can comprise the step of reducing or preventing the expression of CD52 and/or GR (Glucocorticoids receptor also referred to as NR3C1 Uniprot P04150) in addition to that of CCR5.

Engineered Hematopoietic Cells and Populations of Hematopoietic Cells

The present invention is also drawn to the variety of engineered hematopoietic cells obtainable according to one of the embodiments of the method described previously. The cells can be treated under the form of isolated cells or as part of populations of cells.

According to a preferred embodiment the engineered cells of the present invention are primary immune cells, such as NK cells or T-cells, which are generally part of populations of PBMC (peripheral blood mononuclear cells) isolated from donors or patients by leukapheresis. In general, the present method results into a population of cells comprising more than 40%, preferably more than 50%, even more preferably more than 60% of the immune cells, and ideally more than 75% of CCR5 negative T-cells.

These populations of cells, preferably originate from one single donor. The cells comprised into these populations can be purified, sorted and/or pooled into sub populations depending on their specific therapeutic use, The present invention encompasses immune cells comprising any combinations of the different exogenous coding sequences and gene inactivation, which have been respectively and independently described above. Among these combinations are particularly preferred those combining the expression of a CAR under the transcriptional control of an endogenous promoter that is steadily active during immune cell activation and preferably independently from said activation, and the expression of an exogenous sequence encoding a cytokine, such as IL-2, IL-12 or IL-15, under the transcriptional control of a promoter that is up-regulated during the immune cell activation.

The invention is also drawn to a pharmaceutical composition comprising an engineered primary immune cell or immune cell population as previously described for the treatment of HIV infection or cancer, and to a method for treating a patient in need thereof, wherein said method comprises:

preparing a population of engineered primary hematopoietic cells according to the method of the invention as previously described;
optionally, purifying or sorting said engineered hematopoietic cells;
activating said population of engineered primary cells upon or after infusion of said cells into said patient.

Activation and Transformation of HSPC

For mobilised PB (MPB) leukapheresis CD34+, cells are generally processed and enriched using immunomagnetic beads such as CliniMACS, Purified CD34+ cells are seeded on culture bags at $1 \times 10^6$ cells/ml in serum-free medium in the presence of cells culture grade Stem Cell Factor (SCF), preferably 300 ng/ml (Amgen Inc., Thousand Oaks, Calif., USA), preferably with FMS-like tyrosine kinase 3 ligand (FLT3L) 300 ng/ml, and Thrombopoietin (TPO), preferably around 100 ng/ml and further interleukline IL-3, preferably more than 60 ng/ml (all from Cell Genix Technologies) during between preferably 12 and 24 hours before being transferred to an electroporation buffer comprising mRNA encoding the sequence specific reagent. Upon electroporation, the cells are transferred back to the culture medium for usually less than 24 hours prior to being resuspended in saline and transferred in a syringe for infusion.

Allogeneic HSPC transplant requires usually treating the patient with high dose myeloablative and immune suppressive regimen to deplete host bone marrow stem cells and prevent rejection versus graft versus host disease (GvHD). Reduced dose chemotherapy regimen with busulfan at 25% of standard dose is although generally sufficient to achieve significant engraftment of gene corrected cells while reducing conditioning-related toxicity [Aiuti A. et al. (2013) Lentivirus-based Gene Therapy of Hematopoietic Stem Cells in Wiskott-Aldrich Syndrome. Science. 23; 341 (6148)]. Stronger chemotherapy regimen can be based on administration of both busulfan and fludarabine as depleting agents for endogenous HSPC. The dose of busulfan and fludarabine are approximately 50% and 30% of the ones employed in standard allogeneic transplantation. Fludarabine is also useful to break the homeostasis in the compartment of early lymphoid progenitors and to favor the establishment of a pool of corrected naïve T cells in the periphery.

Activation and Expansion of T Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. T cells are generally expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Compositions and Indications

The method of the present invention described above allows producing engineered hematopoietic cells within a limited time frame of about 15 to 30 days, preferably between 15 and 20 days, and most preferably between 18 and 20 days so that they keep their full engraftment potential, especially with respect to their cytotoxic activity.

These cells form a population of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells.

The invention is thus more particularly drawn to a therapeutically effective population of primary T-cells, wherein at least 30%, preferably 50%, more preferably 80% of the cells in said population have been modified according to any one the methods described herein. Said therapeutically effective population of primary immune cells, as per the present invention, comprises immune cells that have reduced or none CCR5 expression.

Such compositions or populations of cells can thus be used as medicaments; especially for treating HIV, particularly for making patients resistant to HIV infection. This treatment may be combined with the treatment of lymphoma, but also for solid tumors such as melanomas, neuroblastomas, gliomas or carcinomas such as lung, breast, colon, prostate or ovary tumors in a patient in need thereof, especially by heterologous expression of CARs.

The treatments involving the engineered primary hematopoietic cells according to the present invention can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

When T-cells are directly used for allogenic purposes, the engineered CCR5 negative cells of the invention are also preferably TCR negative. In such case, the present method allows to produce from one donor a population of cells, wherein at least 40%, preferably 50%, more preferably 60% of the cells in said population have at least one CCR5 allele and one TCR allele being inactivated.

With respect to cancer treatment, the present invention may comprise one of the following steps:

Determining specific antigen markers present at the surface of patients tumors biopsies;

providing a population of engineered CCR5 negative primary immune cells engineered by one of the methods of the present invention previously described further expressing a CAR directed against said specific antigen markers;

Administrating said engineered population of engineered primary immune cells to said patient, Generally, said populations of cells mainly comprises CD4 and CD8 positive hematopoietic cells, such as T-cells, which can undergo robust in vivo T cell expansion and can persist for an extended amount of time in-vitro and in-vivo. Said isolated cell according to the invention or cell line derived from said isolated cell can be used for the treatment of liquid tumors, and preferably of T-cell acute lymphoblastic leukemia.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention the CCR5 defective primary cells of the invention can be used in combination with anti HIV drugs. HIV management can include the use of antiretroviral drugs in order to control HIV infection. By way of example and not of limitation, classes of drugs for the treatment or management of HIV can include entry or fusion inhibitors (e.g., maraviroc and enfuvirtide), nucleoside reverse transcriptase inhibitors (e.g., zidovudine, abicavir, lamivudine, emtricitabine, and tenofovir), Non-nucleoside reverse transcriptase inhibitors (e.g., nevirapine, efavirenz, etravirine, and rilpivirine), integrase inhibitors (e.g., elvitegravir and dolutegravir), and/or protease inhibitors (e.g., Lopinavir, Indinavir, Nelfinavir, Amprenavir, Ritonavir, Darunavir, and Atazanavir).

According to another preferred embodiment of the invention, said treatment can be administrated into patients undergoing an immunosuppressive treatment. Indeed, the present invention preferably relies on cells or population of cells, which have been made resistant to at least one immunosuppressive agent such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The present invention thus can provide more than 10, generally more than 50, more generally more than 100 and usually more than 1000 doses comprising between $10^6$ to $10^8$ gene edited cells originating from a single donor's or patient's sampling.

The cells or population of cells can be administrated in one or more doses. In another embodiment, said effective amount of cells are administrated as a single dose.

In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 10 base pairs (bp) in length, more preferably of 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). Precision genome surgery. *Nat. Biotechnol.* 25(7): 743-4.).

By "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

By "mutation" is intended the substitution, deletion, insertion of up to one, two, three, four, five, six, seven, eight, nine, ten, eleven, twelve, thirteen, fourteen, fifteen, twenty, twenty five, thirty, fourty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

By "vector" is meant a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non-chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g. adeno-associated viruses (AAV), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

As used herein, the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Example 1: Comparison of Site Specific Nuclease Targeting CCR5 Locus in Cell Lines Six different TALEN® pairs (T), a ZFN pair (Z) and a MegaTAL nuclease (MT) were compared for their cleavage activity in human U2OS cells. Among the six TALEN pairs, one was designed to cleave the N-terminal region (SEQ ID NO:2) of CCR5 gene (T3), two were designed to cleave at the target site of the ZFN used in the clinic (T1 and T2), three were designed to cleave close to the delta32 (CCR5 Δ32) mutation (T4 to T6, respectively). The MegaTAL cleaves downstream of the Δ32 encoding region. The ZFN pair is replicating the ZFN used in the clinic. Their localization on CCR5 sequence is presented in FIGS. 1 and 2A.

TALEN® is a trademark owned by the applicant (Cellectis SA, 8 rue de la Croix Jarry, 75013 PARIS) to designate heterodimeric TALE-nucleases of commercial grade using the nuclease domain of Fok-1. 450 ng of plasmid encoding left or right unit of the TALEN T1 (SEQ ID NO:18 and SEQ ID NO:20), T2 (SEQ ID NO:22 and SEQ ID NO:24) T3 (SEQ ID NO:10 and SEQ ID NO:11) T4 (SEQ ID NO:26 and SEQ ID NO:28) T5 (SEQ ID NO:26 and SEQ ID NO:30) T6 (SEQ ID NO:32 and SEQ ID NO:34) or encoding ZFN pair (SEQ ID NO:36 and SEQ ID NO:38) were co-transfected on 1×10$^5$ U20S cells using ViaFect Transfection Reagent (Promega) according to manufacturer's protocol. For the megaTAL nuclease two different doses (D1, D2) of the single plasmid (SEQ ID NO:43) was transfected at either 450 or 900 ng. Control experiments without the transfection of any custom-made nuclease are denoted as (C).

Cells were harvested 2 days post transfection and the genomic DNA extracted. Polymerase Chain Reaction (PCR) were performed to amplify the different targeted loci, these PCR were submitted to the T7 Endonuclease 1 assay [New England Biolabs, see Vouillot et al. (2015) Comparison of T7E1 and Surveyor Mismatch Cleavage Assays to Detect Mutations Triggered by Engineered Nucleases. G3. 5(3): 407-415.] allowing the quantification of nucleases activity.

As shown in FIG. 2B all nucleases were active and the nuclease pairs that had superior performances were the TALEN® T3, the TALEN® T6 and the MegaTAL. Messenger RNAs from these nucleases were produced using mMACHINE@ T7 ULTRA Transcription Kit (Thermo Fisher) according to manufacturer's protocol and nucleofected in K562 cell line using the 4D-Nucleofector™ System (Lonza), according to manufacturer's protocol. T7 endonuclease 1 assay was performed to measure each nuclease activity 3 days post nucleofection T3 TALEN® targeting CCR5 N-terminal region had the highest cleavage activity compared to the T6 TALEN® and MegaTAL (FIG. 2C).

Example 2: Site Specific Nucleases Evaluation in Primary CD4+ T-Cells

Primary CD4+ T-cells were used to further evaluate nuclease activity of different site-specific nucleases targeting CCR5 locus. Primary CD4+ T-cells were isolated from healthy donors using magnetic beads (Miltenyi) and cultured in serum free X-Vivo15 (Lonza). CD4+ T cells were electroporated using the Agile Pulse MAX™ (BTX, Harvard apparatus) as described in Poirot et al. [Multiplex Genome-Edited T-cell Manufacturing Platform for "Off-the-Shelf" Adoptive T-cell Immunotherapies. *Cancer Res.* (2015) 75(18):3853-64]. The cells were cultured at a temperature of about 32° C. for 24 hours post electroporation, and then cultivated at 37° C. during 3 days.

It has been shown that Trex2 could increase the cleavage activity due to its 3' to 5' exonuclease activity (as described in WO2012058458). This exonuclease is well suited to increase, mutation rate induced by nuclease generating 3' overhangs, such as I-OnuI (as described in WO2014191525 or WO2014191527). To test this potential stimulation, 10 µg of mRNAs encoding megaTAL were co-electroporated with 10 µg or without mRNA encoding Trex2 (SEQ ID NO:44) in CD4+ T-cells, and their activity were evaluated 12 days post electroporation by T7 endonuclease 1 assay on CCR5 locus and on the closely related CCR2 locus.

As shown in FIG. 3A, at the CCR5 locus addition of Trex2 did not improve cleavage activity which remained around 20% independently of the addition of Trex2 (left panel). However, when analyzing the CCR2 locus (right panel), a weak cleavage activity could be detected in absence of the Trex2 but the indel frequency at this off-target site was more pronounced when Trex2 was added, revealing that megaTAL could generate off-target events at CCR2 locus and suggesting that weak activity is revealed by Trex2.

TALEN® targeting the N terminal region of CCR5 (T3) was compared to the CRISPR-Cas9 system using gRNA #3 localized close to the N terminal region of CCR5 in CD4+ T-cells (see FIG. 1). CD4+ T-cells were electroporated in parallel with either 10 µg of mRNA encoding T3 TALEN® left and right unit or 5 µg of mRNA encoding Cas9 with 5 µg of synthetic gRNA #3 (SEQ ID NO:39). Nuclease activity was evaluated by T7 Endonuclease 1 assay, T3 TALEN® and CRISPR-Cas9 with gRNA #3 showed 64% and 37% of induced mutagenesis, respectively (FIG. 3B).

These results suggested that T3 TALEN® targeting CCR5 N-terminal region was the best suited for clinical application due to its high efficacy in primary T cells.

In order to further demonstrate TALEN® activity and evaluate its functional efficacy on CD4+ T-cells, 10 µg of mRNAs encoding either left (SEQ ID NO:8) and right (SEQ ID NO:9) CCR5 N-terminal specific TALEN® (T3) unit or, 10 µg of mRNA encoding GFP were electroporated into CD4+ T-cells. 4 days post electroporation, cells were tested for CCR5 cell surface by immunostaining using, clone 3A9 (BD Biosciences, cat #560748). Cells were stained 20 min at room temperature, washed and resuspended in FACS buffer (PBS, 5% FCS). Untreated or GFP-treated cells exhibit 16% of CCR5 positive staining. In contrast T3 TALEN® treated cells had only 4% CCR5 positive staining, confirming TALEN® high efficacy in CD4+ T-cells (FIG. 3C).

In order to demonstrate anti-HIV infection functionality of T3 TALEN®, an HIV resistance test was used in CD4+ T-cells using a surrogate HIV test. A GFP expressing lentiviral vector, which was pseudotyped with gp160 from a CCR5 tropic strain was produced. This vector can only transduce CD4+ cells who express CCR5 on their surface (GFP Ψ Bal R5). As control in a parallel challenge an LV vector expressing GFP and pseudotyped with VSV-G was used (GFP VSV-g). This vector transduces every cell independently of the CCR5 status. CD4+ T-cells were electroporated with either left and right T3 TALEN® units mRNAs (TALEN L+R) or with left T3 TALEN® unit mRNA only (TALEN L+L) as negative control. Cells were further challenged with the two viral vectors at MOI of 3. Spinoculation was performed with 4 ng/mL of polybrene, spun 1 h at 200 g at 32° C. The control challenge with VSVG pseudotyped vectors showed similar transduction efficiencies independently of the fact that the cells have been edited or not. In contrast, CCR5 edited CD4+ T-cells (TALEN L+R) were less permissive (70% reduction) to the transduction with gp160 pseudotyped vectors than their unedited counterpart (TALEN L+L), thus confirming resistance to R5 tropic vector (FIG. 3D).

Example 3: CCR5 Site Specific Nucleases in Hematopoietic Stem and Progenitor Cells (HSPC)

First best conditions to achieve high disruptions in CD34+ cells by nucleofection of TALEN® mRNAs into the cells were established. HSPC cells were pre-cultured for 2 days in serum free CellGro Media (CellGenix, Germany) supplemented with 60 ng/mL FLt3, 20 ng/mL TPO and 60 ng/mL SCF (ImmunoTools, Germany) and afterwards 100,000 cells were nucleofected with the P3 Kit (Lonza, Switzerland). A titration nucleofection with an increasing amount from 1+1 µg to 4+4 µg of T3 TALEN® mRNAs in CD34+ cells was performed. The T7 Endonuclease 1 assay demonstrates that the disruption increases concomitantly with increasing amounts of delivered mRNA (FIG. 4A, left panel). An optimum was reached when 3 µg of each TALEN® mRNA unit were co-delivered into CD34+ cells allowing 96% of KO efficiency (FIG. 4A, right panel). The same strategy was applied to identify optimal dose of megaTAL, T6 TALEN® (targeting the Δ32 region) or CRISPR-Cas. For T6 TALEN®, 3 and 4 µg of each unit were tested (FIG. 4B). For MegaTAL the dose response ranged from 6 to 10 µg of mRNA (FIG. 4C) and for CRISPR/Cas9 5 µg of mRNA encoding Cas9 were co transfected with 2 µg of synthetic gRNA #3 (FIG. 4D). T7 Endonuclease 1 assay reveals that none of these site-specific nucleases could reach a high mutation rate (above 50%, FIG. 4B-D), despite high activities in other cells (U20S and/or K562 and/or T cells).

In order to insure the clinical use of edited HSPC, their differentiation potential was evaluated using a Colony Forming Unit (CFU) assay on methylcellulose (according to manufacturer, STEMCELL Technologies). HSPC cells were seeded either right after thawing (Thw) or 2 days after nucleofection with either no mRNA (P), 2 µg of GFP mRNA (GFP), 3+3 µg of T3 TALEN® mRNAs unit (T3), 10 µg of megaTAL mRNA (MT) or without nucleofection (UT). The methylcellulose differentiation assay showed no significant difference between samples demonstrating that edited HSPC can differentiate efficiently in every colony type (FIG. 5).

CFU assay was also used to assess allelic disruption, colonies were picked, their genomic DNA extracted and nucleases target sites were PCR amplified and sequenced. In 21 representative samples treated with TALEN® targeting CCR5 N-terminal region (T3), high disruption rates of >90% that was observed in T7 Endonuclease 1 assay was confirmed by sequencing. Importantly 76% of the disruptions were bi-allelic (addition of homozygous or heterozygous mutated as shown in FIG. 6A) demonstrating a high rate of CCR5 knock-out (FIG. 6B). In the 15 samples treated with MegaTAL cleavage activity was evaluated at 53% (FIG. 6C), although the quantification of the T7 Endonuclease 1 assay showed disruptions levels around 20%. This discrepancy could be due to the sensitivity of the T7 Endonuclease 1 assay or to the low number of colonies analyzed. In these samples only 13% of the colonies showed bi-allelic disruption, corresponding to 35% of the edited colonies.

Example 4: On and Off-Target Analysis by Deep-Sequencing

A major concern of site specific nucleases is their potential of off-target genome modifications. In particular for HSPC transplantation, the off-target modifications that could occur in HSPC would be transmitted to the differentiated progeny cells. The off-target sites of the TALEN® targeting the CCR5 N-terminal region (T3) was thus predicted using PROGNOS (Predicted Report Of Genome-wide Nuclease Off-target Sites) software publically available [Fine et al., (2014) *Nucleic Acids Res* 42 (6): e42]. Surprisingly, the predicted off-target sites did not include CCR2 gene demonstrating that this TALEN® would not lead to concomitant CCR2 genome modification. The top 20 predicted off-target sites and CCR5 target site were PCR amplified and analyzed by deep-sequencing using Illumina MiSeq 2, 7, 3 days post mock or T3 TALEN® delivery in either K562, CD34+ or CD4+ T-cells, respectively. Table 3 shows the percentage of mutation detected at each locus and statistical analysis. The experiment was performed to validate the difference between mock (w/o nuclease) and TALEN® treated (+ nuclease) samples. Table 3 first confirmed data obtained by T7 Endonuclease 1 at CCR5 locus in the different cell type. For the statistical analysis, a so-called z-statistics was performed. The p-values were calculated for the one-sided alternative hypothesis that the modification frequency at the analyzed site (insertion/deletion) is greater for the nuclease treated cells compared to cells transfected with the empty vector. Cleavage rates are different depending on cell type and highest rates (92%) are obtained in CD34+ cells. In CD34+ cells, two off-targets were detected at CNOT10 and FAM5C loci but at very low level, 0.25% and 0.05% respectively. Interestingly, the off target CNOT10 is common to all cell types, while FAM5C is detected only in CD34+ cells. Although off-target analysis is not transferrable from one cell type to another and these differences could be due to different accessibilities of the genome in the different cell types, all off-targets (and therefore CNOT10 and FAM5C) have been found to be located in introns or intergenic regions, minimizing the risk to induce a mutation in the coding sequence and potentially inactivating the gene.

Example 5: Preclinical Approach

Hematopoietic stem and progenitor cells (HSPC), edited with TALEN® CCR5 targeting N-terminal region, were further evaluate to determine their capacity to reconstitute an immune system in vivo.

HSPC were cultured and nucleofected as described above. 2 days post nucleofection with TALEN® T3 mRNAs, GFP mRNA or without mRNA, 400,000 HSPC were transplanted into Rag2$^{-/-}$Il2rg−/− mice. Cells were harvested from bone marrow, spleen and liver, human cells were sorted into CD19, CD3, CD33, pooled, and T7 was performed (FIG. 7).

These results demonstrate that HSPC edited with TALEN® T3 are able to restore an immune system in vivo with leukocytes mutated at CCR5 locus therefore susceptible to HIV resistance.

Example 6: Challenge of CCR5 Edited T Cells with HIV

TALEN® T3-edited CD4$^+$ T cells were infected with X4 and R5 tropic HIV-1, respectively. The extent of HIV replication was determined by monitoring the levels of p24 in the cell supernatant at the indicated days. To assess the potency of the TALEN®T3-edited CD4$^+$ T cells, CCR5 edited cells (CS100) were diluted to 50% (CS50) and 25% (CS25), respectively, with unedited cells.

As shown in FIG. 10 (panel A), unedited cells (UT) allow for HIV replication whereas TALEN® T3-edited CD4+ T cells show reduced viral replication in a dose dependent manner. Undiluted samples (about 88% indels at CCR5) showed the lowest HIV replication, thus providing proof that editing of the CCR5 gene with TALEN® confers resistance to R5 tropic HIV. In a control experiment, cells were challenged with 2 different MOIs of X4 tropic HIV (panel B). Viral replication was monitored by determining p24 levels in the supernatant. As shown, edited and unedited cells were equally susceptible to infection with X4 tropic HIV.

These results demonstrate that TALEN® T3-edited immune cells are less susceptible to HIV infection, and hence show an improved resistance towards R5-tropic HIV.

TABLE 2

| | polynucleotide and polypeptide sequences used in the examples | |
|---|---|---|
| SEQ ID NO: 1 | CCR5 locus (gene ID 1234) | See sequence listing |
| SEQ ID NO: 2 | 30 first CCR5 amino acids (polynucleotide sequence) | ATGGATTATCAAGTGTCAAGTCCAATCTAT GACATCAATTATTATACATCGGAGCCCTGC CAAAAAATCAATGTGAAGCAAATCGCAGCC CGCCTCCTG |
| SEQ ID NO: 3 | 20 first CCR5 amino acids (polynucleotide sequence) | ATGGATTATCAAGTGTCAAGTCCAATCTAT GACATCAATTATTATACATCGGAGCCCTGC |
| SEQ ID NO: 4 | 2-18 CCR5 amino acids (polynucleotide sequence) | TATCAAGTGTCAAGTCCAATCTATGACATC AATTATTATACATCGGAG |
| SEQ ID NO: 5 | TALEN® T3L target sequence | TATCAAGTGTCAAGTC |
| SEQ ID NO: 6 | TALEN® T3R target sequence | ATTATTATACATCGGA |
| SEQ ID NO: 7 | TALEN® T3 spacer sequence | CAATCTATGACATCA |
| | TALEN® T3L-RVDs | NI, NG, HD, NI, NI, NN, NG, NN, NG, HD, NI, NI, NN, NG, HD |
| | TALEN® T3R-RVDs | HD, HD, NN, NI, NG, NN, NG, NI, NG, NI, NI, NG, NI, NI, NG |
| SEQ ID NO: 8 | TALEN® T3L polypeptide sequence | MGDPKKKRKVIDIADLRTLGYSQQQQEKIKP KVRSTVAQHHEALVGHGFTHAHIVALSQHPA ALGTVAVKYQDMIAALPEATHEAIVGVGKQW SGARALEALLTVAGELRGPPLQLDTGQLLKI AKRGGVTAVEAVHAWRNALTGAPLNLTPEQ VVAIASNIGGKQALETVQALLPVLCQAHGLTP QQVVAIASNGGGKQALETVQRLLPVLCQAH GLTPEQVVAIASHDGGKQALETVQRLLPVLC QAHGLTPEQVVAIASNIGGKQALETVQALLP VLCQAHGLTPEQVVAIASNIGGKQALETVQA LLPVLCQAHGLTPQQVVAIASNNGGKQALET VQRLLPVLCQAHGLTPQQVVAIASNGGGKQ ALETVQRLLPVLCQAHGLTPQQVVAIASNNG GKQALETVQRLLPVLCQAHGLTPQQVVAIAS NGGGKQALETVQRLLPVLCQAHGLTPEQVV AIASHDGGKQALETVQRLLPVLCQAHGLTPE QVVAIASNIGGKQALETVQALLPVLCQAHGL TPEQVVAIASNIGGKQALETVQALLPVLCQA HGLTPQQVVAIASNNGGKQALETVQRLLPVL CQAHGLTPQQVVAIASNGGGKQALETVQRL LPVLCQAHGLTPEQVVAIASHDGGKQALETV QRLLPVLCQAHGLTPQQVVAIASNGGGRPA LESIVAQLSRPDPALAALTNDHLVALACLGG RPALDAVKKGLGDPISRSQLVKSELEEKKSE LRHKLKYVPHEYIELIEIARNSTQDRILEMKV MEFFMKVYGYRGKHLGGSRKPDGAIYTVGS PIDYGVIVDTKAYSGGYNLPIGQADEMQRYV EENQTRNKHINPNEWWKVYPSSVTEFKFLF VSGHFKGNYKAQLTRLNHITNCNGAVLSVEE LLIGGEMIKAGTLTLEEVRRKFNNGEINFAAD |
| SEQ ID NO: 9 | TALEN® T3R polypeptide sequence | MGDPKKKRKVIDIADLRTLGYSQQQQEKIKP KVRSTVAQHHEALVGHGFTHAHIVALSQHPA ALGTVAVKYQDMIAALPEATHEAIVGVGKQW SGARALEALLTVAGELRGPPLQLDTGQLLKI AKRGGVTAVEAVHAWRNALTGAPLNLTPEQ VVAIASHDGGKQALETVQRLLPVLCQAHGLT PEQVVAIASHDGGKQALETVQRLLPVLCQAH GLTPQQVVAIASNNGGKQALETVQRLLPVLC QAHGLTPEQVVAIASNIGGKQALETVQALLP VLCQAHGLTPQQVVAIASNGGGKQALETVQ RLLPVLCQAHGLTPQQVVAIASNNGGKQALE TVQRLLPVLCQAHGLTPQQVVAIASNGGGK QALETVQRLLPVLCQAHGLTPEQVVAIASNI GGKQALETVQALLPVLCQAHGLTPQQVVAIA SNGGGKQALETVQRLLPVLCQAHGLTPEQV VAIASNIGGKQALETVQALLPVLCQAHGLTPE |

TABLE 2-continued polynucleotide and polypeptide sequences used in the examples

|  |  |
|---|---|
| | QVVAIASNIGGKQALETVQALLPVLCQAHGL<br>TPQQVVAIASNGGGKQALETVQRLLPVLCQ<br>AHGLTPEQVVAIASNIGGKQALETVQALLPVL<br>CQAHGLTPEQVVAIASNIGGKQALETVQALL<br>PVLCQAHGLTPQQVVAIASNGGGKQALETV<br>QRLLPVLCQAHGLTPQQVVAIASNGGGRPA<br>LESIVAQLSRPDPALAALTNDHLVALACLGG<br>RPALDAVKKGLGDPISRSQLVKSELEEKKSE<br>LRHKLKYVPHEYIELIEIARNSTQDRILEMKV<br>MEFFMKVYGYRGKHLGGSRKPDGAIYTVGS<br>PIDYGVIVDTKAYSGGYNLPIGQADEMQRYV<br>EENQTRNKHINPNEWWKVYPSSVTEFKFLF<br>VSGHFKGNYKAQLTRLNHITNCNGAVLSVEE<br>LLIGGEMIKAGTLTLEEVRRKFNNGEINFAAD |
| SEQ ID NO: 10 TALEN® T3L plasmid sequence | See sequence listing |
| SEQ ID NO: 11 TALEN® T3R plasmid sequence | See sequence listing |
| SEQ ID NO: 17 TALEN® T1L target sequence | TGTGGGCAACATGCTGGTC |
| SEQ ID NO: 18 TALEN® T1L plasmid sequence | See sequence listing |
| SEQ ID NO: 19 TALEN® T1R target sequence | TCTTCAGCCTTTTGCAGTT |
| SEQ ID NO: 20 TALEN® T1R plasmid sequence | See sequence listing |
| SEQ ID NO: 21 TALEN® T2L target sequence | TTTGTGGGCAACATGCTGG |
| SEQ ID NO: 22 TALEN® T2L plasmid sequence | See sequence listing |
| SEQ ID NO: 23 TALEN® T2R target sequence | TCGAGCCTTTTGCAGTTTAT |
| SEQ ID NO: 24 TALEN® T2R plasmid sequence | See sequence listing |
| SEQ ID NO: 25 TALEN® T4/5L target sequence | TCTCATTTTCCATACAGTC |
| SEQ ID NO: 26 TALEN® T4/5L plasmid sequence | See sequence listing |
| SEQ ID NO: 27 TALEN® T4R target sequence | TTTAATGTCTGGAAATTCT |
| SEQ ID NO: 28 TALEN® T4R plasmid sequence | See sequence listing |
| SEQ ID NO: 29 TALEN® T5R target sequence | TAATGTCTGGAAATTCTTC |
| SEQ ID NO: 30 TALEN® T5R plasmid sequence | See sequence listing |
| SEQ ID NO: 31 TALEN® T6L target sequence | TTCATTACACCTGCAGCTC |
| SEQ ID NO: 32 TALEN® T6L plasmid sequence | See sequence listing |
| SEQ ID NO: 33 TALEN® T6R target sequence | TTCCAGAATTGATACTGAC |
| SEQ ID NO: 34 TALEN® T6R plasmid sequence | See sequence listing |
| SEQ ID NO: 35 ZFN L target sequence | GTCATCCTCATC |
| SEQ ID NO: 36 ZFN L plasmid sequence | See sequence listing |

TABLE 2-continued polynucleotide and polypeptide sequences used in the examples

| SEQ ID NO: 37 | ZFN R target sequence | CTTTTGCAGTTT |
|---|---|---|
| SEQ ID NO: 38 | ZFN R plasmid sequence | See sequence listing |
| SEQ ID NO: 39 | gRNA#3 | CCTGCCTCCGCTCTACTCAC |
| SEQ ID NO: 40 | Delta32 | GTCAGTATCAATTCTGGAAGAATTTCCAGACA |
| SEQ ID NO: 41 | MegaTAL-T target sequence | GTCCTTCTCCT |
| SEQ ID NO: 42 | MegaTAL-M cleavage sequence | CTTCCAGGAATTCTTTGGCCTG |
| SEQ ID NO: 43 | MegaTAL polynucleotide sequence | See sequence listing |
| SEQ ID NO: 44 | MegaTAL+ Trex2 polynucleotide sequence | See sequence listing |

TABLE 3 on and off-target results in K562, CD4+ T-cells and CD34+ HSC

| | In/dels frequency | | | | | | | | |
|---|---|---|---|---|---|---|---|---|---|
| | K562 | | | CD34+ | | | CD4+ T-cell | | |
| Locus analyzed | +nuclease | w/o nuclease | p value | +nuclease | w/o nuclease | p value | +nuclease | w/o nuclease | p value |
| CCR5 | 73.87% | 0.14% | <0.0001 | 92.23% | 0.19% | <0.0001 | 60.24% | 0.05% | <0.0001 |
| CNOT10 | 0.05% | 0.03% | 0.0037 | 0.25% | 0.03% | <0.0001 | 0.05% | 0.03% | 0.0005 |
| FAM5C | 0.02% | 0.02% | 0.1846 | 0.05% | 0.02% | 0.0015 | 0.02% | 0.02% | 0.1609 |
| CACNA1F | 0.05% | 0.06% | 0.9696 | 0.05% | 0.06% | 0.7622 | 0.06% | 0.05% | 0.041 |
| CEP112 | 0.01% | 0.02% | 0.6008 | 0.03% | 0.02% | 0.0851 | 0.02% | 0.01% | 0.3107 |
| GPR151 | 0.08% | 0.07% | 0.2414 | 0.07% | 0.06% | 0.1305 | 0.07% | 0.06% | 0.1702 |
| IQCJ-SCHIIP1 | 0.22% | 0.21% | 0.2595 | 0.27% | 0.24% | 0.1453 | 0.23% | 0.23% | 0.5163 |
| LINC00308 | 0.03% | 0.04% | 0.7945 | 0.04% | 0.04% | 0.3867 | 0.02% | 0.05% | 0.9974 |
| LOC401494 | 0.03% | 0.02% | 0.1014 | 0.02% | 0.02% | 0.5267 | 0.02% | 0.02% | 0.6705 |
| LOC440040 | 0.01% | 0.01% | 0.456 | 0.02% | 0.02% | 0.4717 | 0.01% | 0.02% | 0.9097 |
| LOC442459 | 0.06% | 0.04% | 0.2664 | 0.06% | 0.07% | 0.5948 | 0.07% | 0.06% | 0.4224 |
| LRRK2 | 0.05% | 0.04% | 0.1768 | 0.04% | 0.03% | 0.1279 | 0.04% | 0.03% | 0.1893 |
| MIR944 | 0.09% | 0.05% | 0.0145 | 0.05% | 0.07% | 0.8524 | 0.04% | 0.03% | 0.105 |
| ORC5 | 0.06% | 0.05% | 0.3786 | 0.1% | 0.09% | 0.2947 | 0.04% | 0.08% | 0.9973 |
| PCDH7 | 0.04% | 0.03% | 0.1221 | 0.03% | 0.03% | 0.4944 | 0.03% | 0.04% | 0.7626 |
| R3HCC1L | 0.05% | 0.05% | 0.4985 | 0.09% | 0.06% | 0.0261 | 0.04% | 0.04% | 0.5458 |
| RASSF3 | 0.01% | 0.01% | 0.3934 | 0.02% | 0.01% | 0.0447 | 0.01% | 0.01% | 0.9039 |
| SLC24A2 | 0.02% | 0.02% | 0.4247 | 0.02% | 0.02% | 0.5932 | 0.02% | 0.02% | 0.1725 |
| SMYD3 | 0.04% | 0.03% | 0.0766 | 0.03% | 0.03% | 0.9066 | 0.05% | 0.02% | 0.0041 |
| TIAM1 | 0.08% | 0.07% | 0.4507 | 0.08% | 0.06% | 0.157 | 0.06% | 0.07% | 0.5574 |
| TYR | 0.02% | 0.01% | 0.4415 | 0.02% | 0.01% | 0.0731 | 0.02% | 0.03% | 0.8937 |

TABLE 4

Selection of genes that are upregulated over more than 24 hours upon T-cell activation.

| Symbol | Description |
|---|---|
| Gzmb | granzyme B |
| Tbx21 | T-box 21 |
| Pdcd1 | programmed cell death 1 |
| Plek | pleckstrin |
| Chek1 | checkpoint kinase 1 |
| Slamf7 | SLAM family member 7 |
| Zbtb32 | zinc finger and BTB domain containing 32 |
| Tigit | T cell immunoreceptor with Ig and ITIM domains |
| Lag3 | lymphocyte-activation gene 3 |
| Gzma | granzyme A |
| Wee1 | WEE 1 homolog 1 (*S. pombe*) |
| Il12rb2 | interleukin 12 receptor, beta 2 |
| Ccr5 | chemokine (C-C motif) receptor 5 |
| Eea1 | early endosome antigen 1 |
| Dtl | denticleless homolog (*Drosophila*) |

The invention claimed is:

1. A method for producing HIV resistant primary hematopoietic cells comprising at least the steps of:
   (i) providing a population of primary hematopoietic cells originating from a patient or a donor;
   (ii) introducing into said cells a nucleic acid encodinq a sequence specific reagent targeting at least one genomic sequence encoding the N-terminal hydrophilic external region of the CCR5 protein, wherein said specific reagent is a TALE-nuclease that binds a target sequence selected from SEQ ID NO:5 and SEQ ID NO:6;
   (iii) expressing said sequence specific reagent, so that the expression of functional CCR5 is reduced by more than 50% in the resulting population of primary cells.

2. The method of claim 1, wherein said expression of functional CCR5 is reduced by more than 60% in the resulting population of primary cells.

3. The method of claim 1, wherein said expression of functional CCR5 is reduced by more than 70% in the resulting population of primary cells.

4. The method of claim 1, wherein said reduced expression of functional CCR5 is reached without cleaving CCR2 gene.

5. The method of claim 1, wherein said population of primary cells comprise at least 50% CD34+ cells.

6. The method of claim 1, wherein said population of primary cells comprise at least 50% T-cells.

7. The method of claim 6, further comprising a targeted gene insertion into said genomic sequence encoding the N-terminal hydrophilic external region of the CCR5 protein.

8. The method of claim 7, wherein said targeted gene insertion comprises an exogenous sequence selected from one encoding a protein conferring resistance to a drug or useful as a selectable marker,
   encoding a protein which expression contributes to inhibiting CXCR4 pathway for broader HIV resistance, or
   encoding chimeric antigen receptor (CAR).

9. The method of claim 1, wherein said TALE-nuclease has monomer polypeptides comprising respectively at least the 10 first RVDs of the respective RVD sequences in the following order:

NI, NG, HD, NI, NI, NN, NG, NN, NG, HD, NI, NI, NN, NG, HD

HD, HD, NN, NI, NG, NN, NG, NI, NG, NI, NI, NG, NI, NI, NG.

10. The method of claim 1, wherein said TALE-nuclease monomers have respectively a polypeptide sequence sharing at least 95% identity with SEQ ID NO:8 and SEQ ID NO:9.

11. The method of claim 1, wherein said sequence specific reagent is expressed from mRNA transfected by electroporation.

12. The method of claim 1, wherein said population of primary hematopoietic cells in step i) are derived from iPS cells.

13. The method of claim 1, wherein said population of primary hematopoietic cells are further dedifferentiated into iPS cells.

14. A population of hematopoietic primary cells obtained by the method of claim 1.

15. The population of cells of claim 14, wherein at least 50% of the cells comprise bi-allelic mutations in a genomic sequence having at least 80% identity with SEQ ID NO:2 encoding the N-terminal hydrophilic external region of the CCR5 protein, without cleavage in the CCR2 gene.

16. A method for treatment of a patient who is HIV positive comprising administering the population of primary cells of claim 14 to the patient.

17. A method for treatment of a patient who is HIV positive comprising administering the population of primary cells of claim 15 to the patient.

18. A method for treatment of a cancer patient comprising administering a population of primary cells of claim 14 to the patient.

19. A TALE-nuclease monomer designed to cleave a genomic sequence encoding the N-terminal hydrophilic external region of the CCR5 protein, wherein said monomer binds a target sequence of SEQ ID NO:5 or SEQ ID NO:6.

20. The TALE-nuclease monomer of claim 19, wherein said TALE-nuclease has a N-terminal region from AvrBs3 of 152 amino acids.

21. The TALE-nuclease monomer of claim 20, wherein said monomer has a polypeptide sequence sharing at least 95% identity with SEQ ID NO:8 or SEQ ID NO:9.

22. A pair of the TALE-nuclease monomers of claim 19, each monomer thereof binding respectively the polynucleotide target sequences SEQ ID NO:5 and SEQ ID NO:6.

23. The pair of the TALE-nuclease monomers of claim 22, wherein said dimeric TALE-nuclease polypeptides comprise respectively at least the ten first RVDs of the respective RVD sequences in the following order:

NI, NG, HD, NI, NI, NN, NG, NN, NG, HD, NI, NI, NN, NG, HD

HD, HD, NN, NI, NG, NN, NG, NI, NG, NI, NI, NG, NI, NI, NG.

24. The pair of the TALE-nuclease monomers of claim 23, wherein said TALE-nuclease monomers have respectively a polypeptide sequence sharing at least 95% identity with NO:8 and SEQ ID NO:9.

* * * * *